(12) United States Patent
Baym et al.

(10) Patent No.: US 10,213,225 B2
(45) Date of Patent: Feb. 26, 2019

(54) ROBOTIC DEBRIDEMENT APPARATUSES, AND RELATED SYSTEMS AND METHODS

(71) Applicant: Elwha LLC, Bellevue, WA (US)

(72) Inventors: Michael H. Baym, Cambridge, MA (US); Mahalaxmi Gita Bangera, Renton, WA (US); Hon Wah Chin, Palo Alto, CA (US); Roderick A. Hyde, Redmond, WA (US); Jordin T. Kare, San Jose, CA (US); Nathan P. Myhrvold, Bellevue, WA (US); Elizabeth A. Sweeney, Seattle, WA (US)

(73) Assignee: ELWHA LLC, Bellevue, WA (US)

( * ) Notice: Subject to any disclaimer, the term of this patent is extended or adjusted under 35 U.S.C. 154(b) by 209 days.

(21) Appl. No.: 15/197,360

(22) Filed: Jun. 29, 2016

(65) Prior Publication Data

US 2018/0000501 A1    Jan. 4, 2018

(51) Int. Cl.
*A61B 17/3205*  (2006.01)
*A61B 34/32*  (2016.01)
(Continued)

(52) U.S. Cl.
CPC .. *A61B 17/3205* (2013.01); *A61B 17/320068* (2013.01); *A61B 34/32* (2016.02); *A61B 18/00* (2013.01); *A61B 2017/00022* (2013.01); *A61B 2017/00084* (2013.01); *A61B 2017/00402* (2013.01); *A61B 2017/00747* (2013.01); *A61B 2017/320008* (2013.01); *A61B 2018/00452* (2013.01); *A61B 2018/00601* (2013.01); *A61B 2018/00636* (2013.01)

(58) Field of Classification Search
None
See application file for complete search history.

(56) References Cited

U.S. PATENT DOCUMENTS 5,447,505 A * 9/1995 Valentine ............... A61L 15/24
602/48
6,240,312 B1    5/2001 Alfano et al.
(Continued)

OTHER PUBLICATIONS

Unknown, "These 3D-Printed Microfish Were Created to Sniff Out and Remove Toxins". http://www.eedesignit.com/author/editorial/. Aug. 26, 2015.
(Continued)

*Primary Examiner* — Brian T Gedeon
(74) *Attorney, Agent, or Firm* — Dorsey & Whitney LLP

(57) ABSTRACT

Robotic debridement apparatuses, related systems, and methods of using the same are disclosed herein. The robotic debridement apparatuses are configured to facilitate debridement of tissue from a body region. For example, the robotic debridement apparatuses can include one or more of at least one debriding tool configured to debride tissue, at least one debris disposal device configured to capture substances in the body region. The systems disclosed herein can include a plurality of robotic debridement apparatuses. The systems disclosed herein can include a dressing associated with the plurality of robotic debridement apparatuses. The dressing can be associated with the robotic debridement apparatuses in a manner that facilitates operations of the robotic debridement apparatuses.

56 Claims, 32 Drawing Sheets

(51) Int. Cl.
*A61B 17/32* (2006.01)
*A61B 18/20* (2006.01)
*A61B 18/00* (2006.01)
*A61B 17/00* (2006.01)

(56) References Cited

U.S. PATENT DOCUMENTS

| | | | | |
|---|---|---|---|---|
| 6,824,508 B2* | 11/2004 | Kim | ............... | A61B 1/00156 348/82 |
| 7,931,611 B2 | 4/2011 | Novak et al. | | |
| 7,998,060 B2* | 8/2011 | Ferren | ............... | A61B 1/00156 600/114 |
| 8,066,632 B2* | 11/2011 | Dario | ............... | A61B 1/00156 600/118 |
| 9,861,296 B2* | 1/2018 | Gazdzinski | ............... | A61B 5/073 |
| 2002/0173700 A1* | 11/2002 | Kim | ............... | A61B 1/00156 600/114 |
| 2004/0050394 A1* | 3/2004 | Jin | ............... | A61B 1/00158 128/899 |
| 2006/0089533 A1* | 4/2006 | Ziegler | ............... | A61B 1/00156 600/114 |
| 2006/0100567 A1* | 5/2006 | Marchitto | ............... | A61B 17/54 604/19 |
| 2010/0010458 A1 | 1/2010 | Sherman | | |
| 2010/0113874 A1 | 5/2010 | Quirini et al. | | |
| 2012/0035540 A1* | 2/2012 | Ferren | ............... | A61B 1/041 604/95.01 |

OTHER PUBLICATIONS

Enoch, Stuart, "Wound Bed Preparation: The Science Behind the Removal of Barriers to Healing", Health Management Publications, Inc., Wounds. 2003;15(7). 1-30. http://www.medscape.com/viewarticle/459733_6.

Firebaugh, S.L., et al., "Soccer at the Microscale: Small Robots with Big Impact", Robot Soccer, Vladan Papi (Ed.), ISBM: 978-953-307-036-0, InTech. 2010, 285-311. http://www.intechopen.com/books/robot-soccer/soccer-at-the-microscale-small-robots-with-big-impact.

Halverson, Nic, "Maggot-Like Robot Eats Brain Tumors", DNews. Robotics. http://news.discovery.com/tech/robotics. Sep. 10, 2013.

Kim, Yeongjin, et al., "Minimally Invasive Neurosurgical Intracranial Robot (MINIR-I and MINIR-II)", Robotics Automation & Medical Systems Laboratory. 1-6. http://rams.umd.edu/minir/. Sep. 23, 2015.

Liu, Weiting, et al., "A Biometric Sensor for a Crawling Minirobot", Robotics and Autonomous Systems 54 (2006). 513-528 www.elsevier.com/locate/robot. Jun. 15, 2006.

* cited by examiner

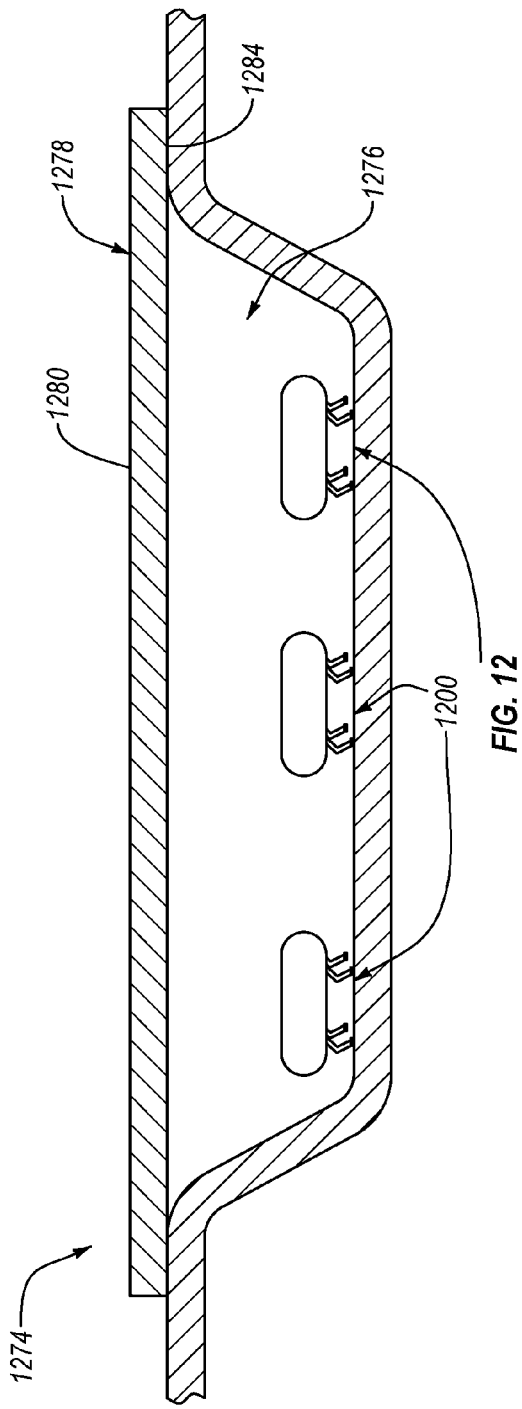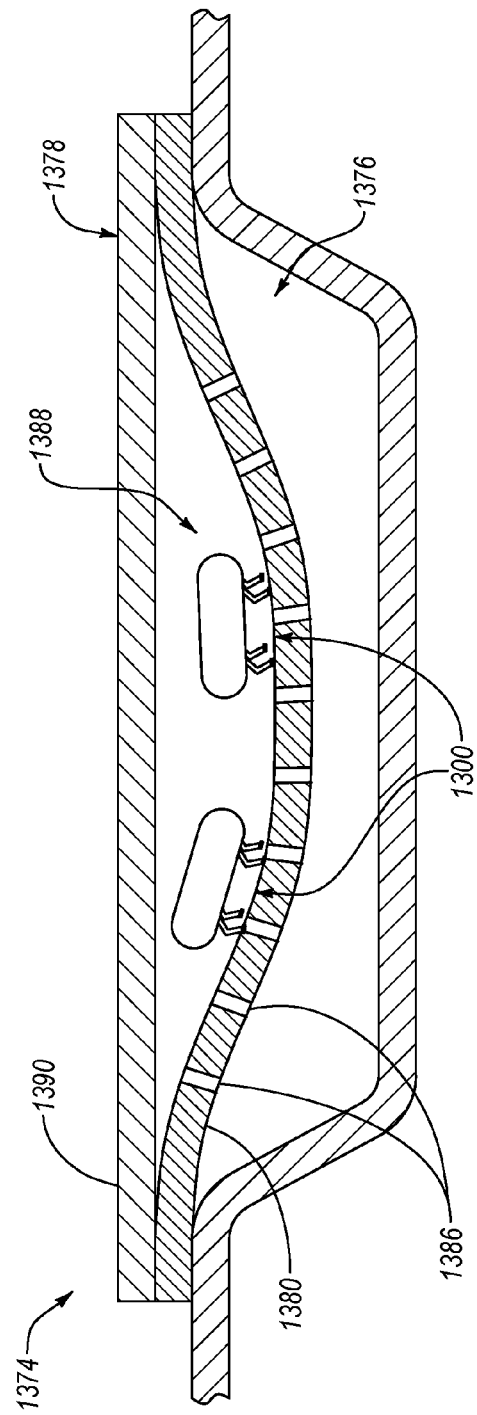

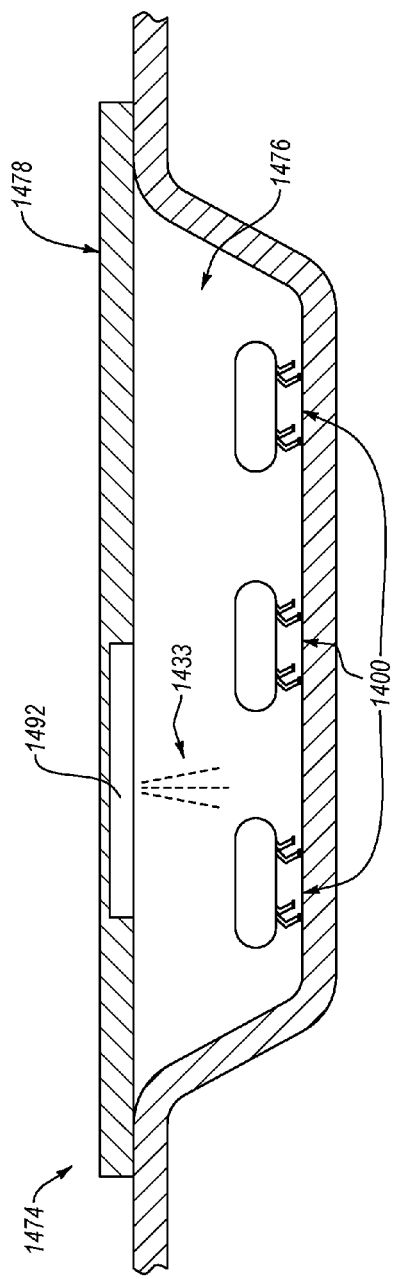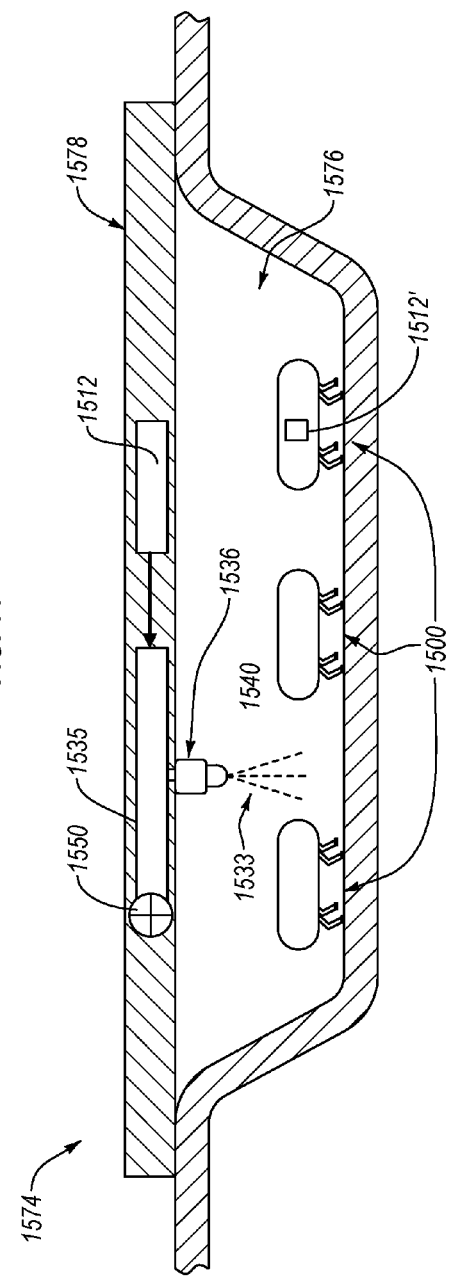

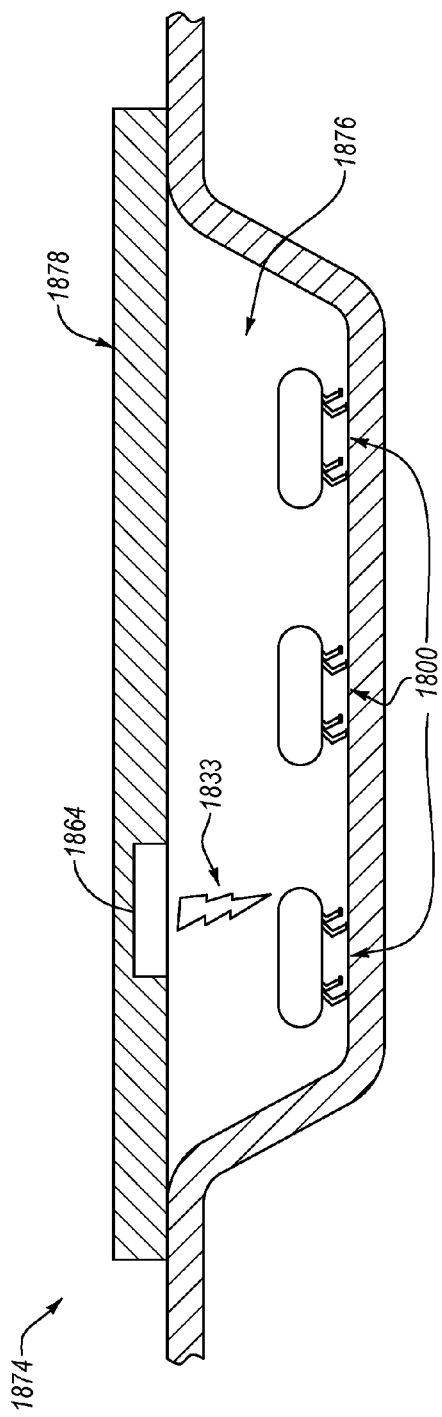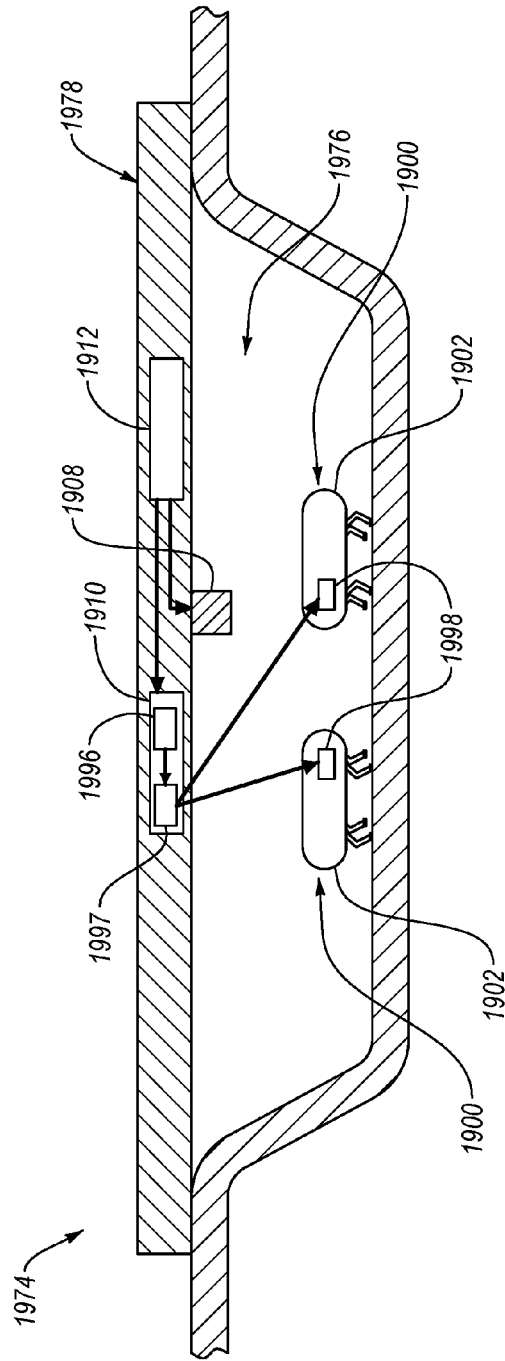

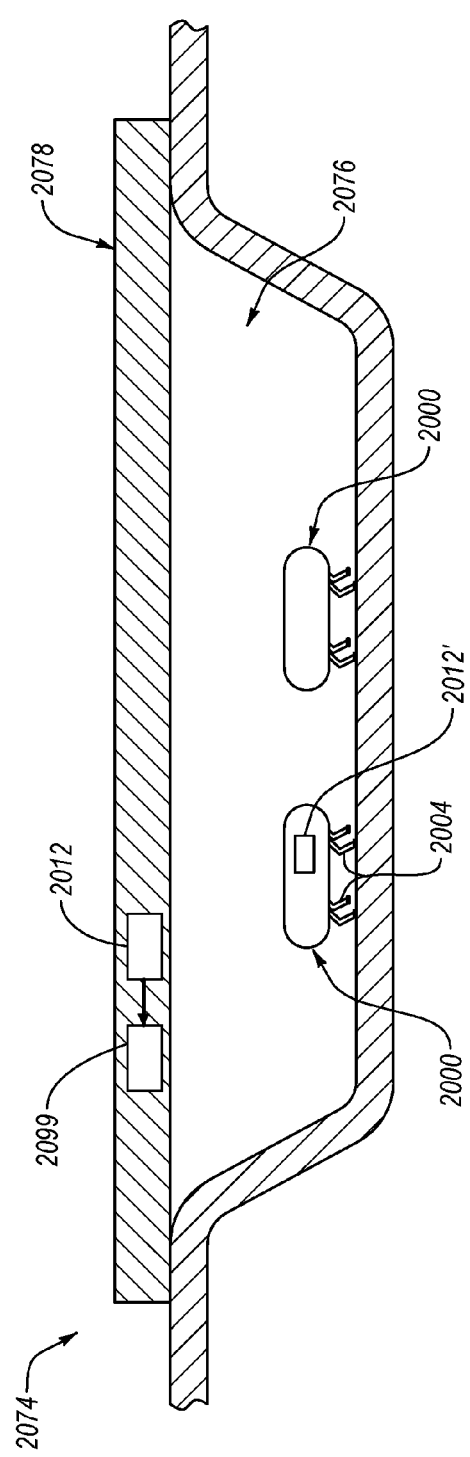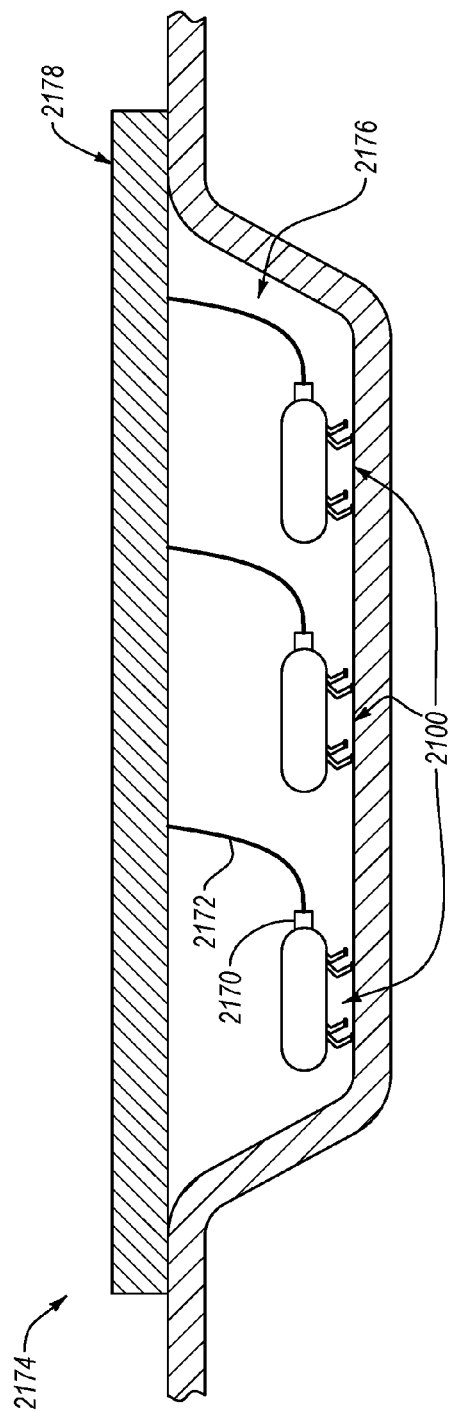

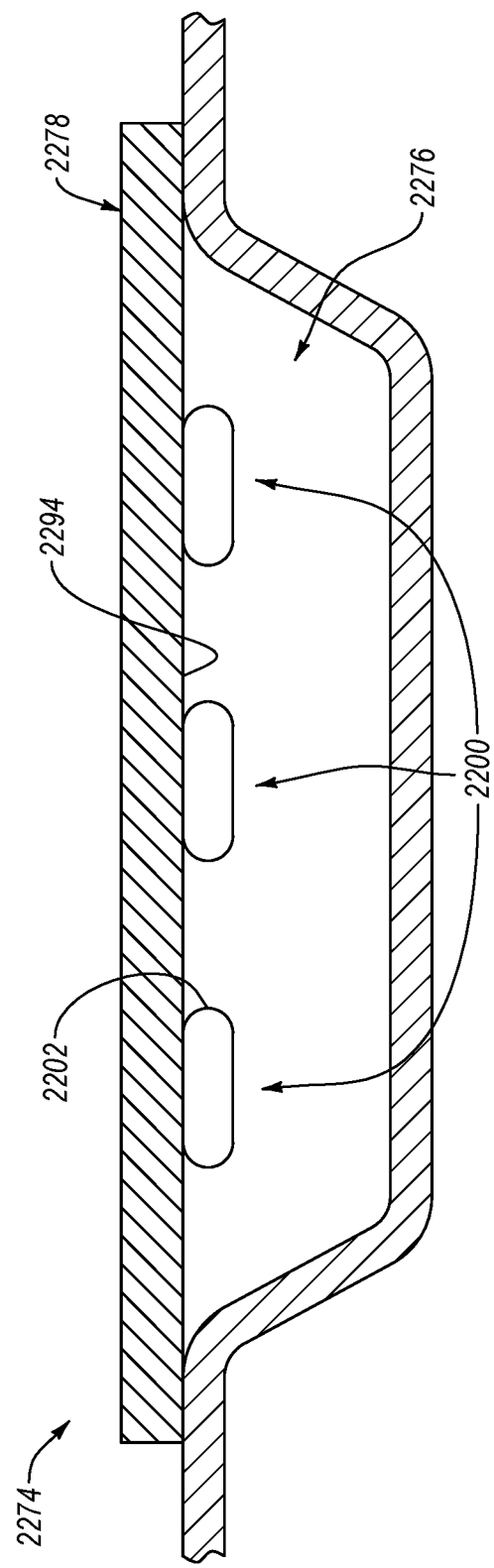

ROBOTIC DEBRIDEMENT APPARATUSES, AND RELATED SYSTEMS AND METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Embodiments disclosed herein relate to robotic debridement apparatuses, systems using one or more of the robotic debridement apparatuses, and methods of using the same. The robotic debridement apparatuses disclosed herein are configured to facilitate debridement of tissue (e.g., target tissue) from a body region. For example, the robotic debridement apparatuses can include one or more of at least one debriding tool configured to debride tissue (e.g., target tissue), at least one debris disposal device configured to capture at least one substance from the body region, or at least one therapeutic device configured to provide a therapeutic effect to the body region. In an embodiment, robotic debridement systems disclosed herein can include a plurality of robotic debridement apparatuses. In an embodiment, robotic debridement systems disclosed herein can include a dressing associated with a plurality of robotic debridement apparatuses. The dressing can be associated with the robotic debridement apparatuses in a manner that facilitates operation of the robotic debridement apparatuses or facilitates debridement of tissue from the body region.

In an embodiment, a robotic debridement apparatus is disclosed. In an embodiment, the robotic debridement apparatus includes a housing. In an embodiment, the robotic debridement apparatus further includes at least one locomotive mechanism positioned in or on the housing. In an embodiment, the at least one locomotive mechanism is configured to generate a self-propelling locomotive force. In an embodiment, the robotic debridement apparatus also includes at least one debriding tool associated with the housing.

In an embodiment, a robotic debridement apparatus is disclosed. In an embodiment, the robotic debridement apparatus includes a housing. In an embodiment, the robotic debridement apparatus further includes at least one locomotive mechanism positioned in or on the housing. In an embodiment, the at least one locomotive mechanism is configured to generate a self-propelling locomotive force. In an embodiment, the robotic debridement apparatus additionally includes at least one debriding tool associated with the housing. In an embodiment, the robotic debridement apparatus also includes one or more sensors positioned in or on the housing.

In an embodiment, a robotic debridement system is disclosed. In an embodiment, the robotic debridement system includes a plurality of robotic debridement apparatuses. In an embodiment, at least one of the plurality of robotic debridement apparatuses includes a housing and at least one locomotive mechanism positioned in or on the housing. In an embodiment, the at least one locomotive mechanism is configured to generate a self-propelling locomotive force. In an embodiment, the at least one of the plurality of robotic debridement apparatuses further includes at least one debriding tool associated with the housing.

In an embodiment, a method is disclosed. In an embodiment, the method includes contacting a body region of a subject with at least one robotic debridement apparatus. In an embodiment, the at least one of the plurality of robotic debridement apparatuses includes a housing and at least one locomotive mechanism positioned in or on the housing. In an embodiment, the at least one locomotive mechanism is configured to generate a self-propelling locomotive force. In an embodiment, the at least one robotic debridement apparatus further includes at least one debriding tool associated with the housing. In an embodiment, the method further includes, via the at least one debriding tool, debriding at least one target tissue from the body region.

In an embodiment, a robotic debridement system is disclosed. In an embodiment, the robotic debridement system includes a plurality of robotic debridement apparatuses. In an embodiment, at least one of the plurality of robotic debridement apparatuses includes a housing and at least one of at least one debriding tool associated with the housing. In an embodiment, the robotic debridement system further includes a dressing associated with the at least one of the plurality of robotic debridement apparatuses. In an embodiment, the dressing includes at least one layer that at least partially encloses the at least one of the plurality of robotic debridement apparatuses.

In an embodiment, a robotic debridement system is disclosed. In an embodiment, the robotic debridement system includes a plurality of robotic debridement apparatuses. In an embodiment, at least one of the plurality of robotic debridement apparatuses includes a housing and at least one of at least one debriding tool associated with the housing. In an embodiment, the robotic debridement system further includes a dressing associated with the at least one of the plurality of robotic debridement apparatuses. In an embodiment, the dressing includes at least one layer that at least partially encloses the at least one of the plurality of robotic debridement apparatuses. In an embodiment, the robotic debridement system also includes one or more sensors positioned in or on at least one of the housing of the at least one of the plurality of robotic debridement apparatuses or the dressing.

In an embodiment, a method is disclosed. In an embodiment, the method includes positioning a plurality of robotic debridement apparatuses at or near a body region. In an embodiment, the body region includes at least one target tissue (e.g., that is desired to be modified by the robotic debridement apparatuses). In an embodiment, at least one of the plurality of robotic debridement apparatuses includes a housing and at least one debriding tool associated with the housing. In an embodiment, the method further includes reversibly attaching a dressing associated with the plurality of robotic debridement apparatuses to the body region. In an embodiment, the method additionally includes, via the at least one debriding tool, debriding the at least one target tissue present within the body region.

In an embodiment, a robotic debridement apparatus is disclosed. In an embodiment, the robotic debridement apparatus includes a housing and at least one locomotive mechanism positioned in or on the housing. In an embodiment, the at least one locomotive mechanism is configured to generate a self-propelling locomotive force. In an embodiment, the robotic debridement apparatus also includes at least one debris disposal device positioned in or on the housing. In an embodiment, the debris disposal device is configured to capture at least one substance from a body region.

In an embodiment, a robotic debridement apparatus is disclosed. In an embodiment, the robotic debridement apparatus includes a housing and at least one locomotive mechanism positioned in or on the housing. In an embodiment, the at least one locomotive mechanism is configured to generate a self-propelling locomotive force. In an embodiment, the robotic debridement apparatus also includes at least one debris disposal device positioned in or on the housing. In an embodiment, the debris disposal device is configured to capture at least one substance from a body region. In an embodiment, the robotic debridement apparatus further includes one or more sensors positioned in or on the housing.

In an embodiment, a robotic debridement system is disclosed. In an embodiment, the robotic debridement system includes a plurality of robotic debridement apparatuses. At least one of the plurality of robotic debridement apparatuses includes a housing and at least one locomotive mechanism positioned in or on the housing. In an embodiment, the at least one locomotive mechanism is configured to generate a self-propelling locomotive force. In an embodiment, the at least one of the plurality of robotic debridement apparatuses further includes at least one debris disposal device positioned in or on the housing. In an embodiment, the debris disposal device is configured to capture at least one substance from a body region.

In an embodiment, a method is disclosed. In an embodiment, the method includes contacting a body region of the subject with at least one robotic debridement apparatus. In an embodiment, the at least one robotic debridement apparatus including a housing and at least one locomotive mechanism positioned in or on the housing. In an embodiment, the at least one locomotive mechanism configured to generate a self-propelling locomotive force. In an embodiment, the at least one robotic debridement apparatus also including at least one debris disposal device positioned in or on the housing. In an embodiment, the method also includes capturing with the at least one debris disposal device at least one substance from the body region.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 12 is a schematic view of a system that includes a dressing and at least one robotic debridement apparatus positioned in a body region, according to an embodiment.

FIG. 13 is a schematic view of a system that includes a dressing and at least one robotic debridement apparatus positioned in a body region, according to an embodiment.

FIGS. 14-22 are schematic illustrations of different systems that include a dressing having different associations with a plurality of robotic debridement apparatuses, according to different embodiments.

DETAILED DESCRIPTION

Figure 1:
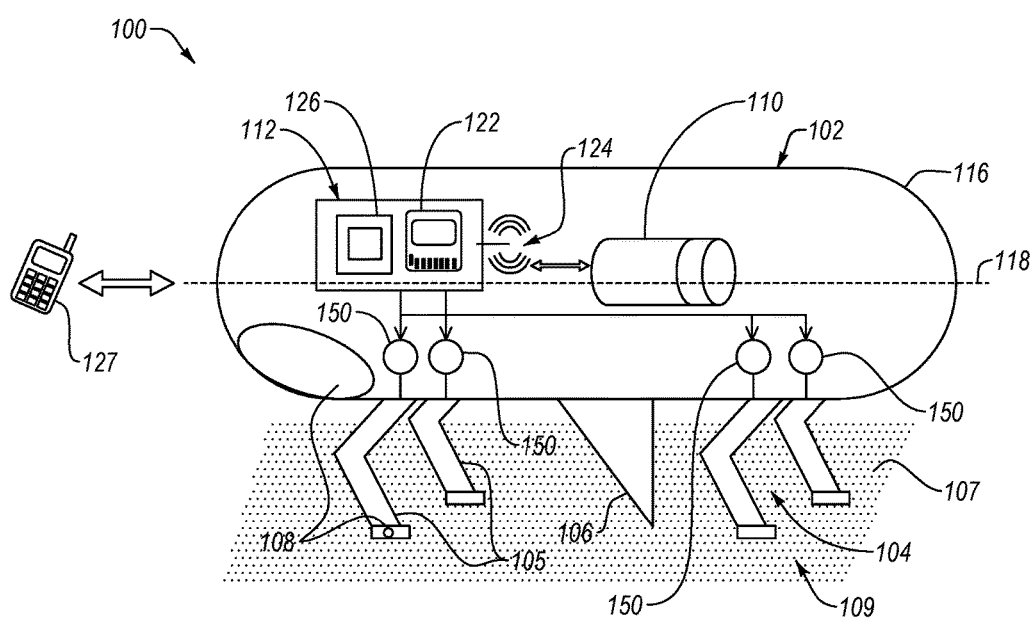
FIG. 1 is a schematic illustration of a robotic debridement apparatus, according to an embodiment.

Embodiments disclosed herein relate to robotic debridement apparatuses, systems using one or more of the robotic debridement apparatuses, and methods of using the same. The robotic debridement apparatuses disclosed herein are configured to facilitate debridement of tissue (e.g., at least one target tissue) from a body region. For example, the robotic debridement apparatuses can include one or more of at least one debriding tool configured to debride tissue (e.g., at least one target tissue) or at least one debris disposal device configured to capture at least one substance from the body region. For example, the robotic debridement apparatuses can include at least one locomotive mechanism configured to generate a self-propelling locomotive force to allow travel within a body region. In an embodiment, the robotic debridement apparatuses can include at least one therapeutic delivery device configured to deliver at least one of a therapeutic agent or a therapeutic treatment to the body region. In an embodiment, robotic debridement systems disclosed herein can include a plurality of robotic debridement apparatuses. In an embodiment, robotic debridement systems disclosed herein can include a dressing associated with a plurality of robotic debridement apparatuses. The dressing can be associated with the robotic debridement apparatuses in a manner that facilitates operations of the robotic debridement apparatuses or facilitates debridement of tissue from the body region. In an embodiment, the robotic debridement apparatuses can include one or more sensors.

In an embodiment, the body region includes a wound region of a subject. For example, the robotic debridement apparatuses disclosed herein can be used to debride tissue from the wound region. The wound region can include a wound, such as a traumatic wound, a burn wound, a surgical wound, an ulcerative wound, a pressure ulcer, a diabetic ulcer, or any other suitable wound. The wound region can also include a portion of the subject that extends about the wound (e.g., viable tissue, such as a skin surface, that extends about the wound) or a region directly above or below the wound. The wound region can include both viable tissue (e.g., healthy, unaffected tissue and/or damaged but recoverable tissue) and nonviable tissue (e.g., dead, dying, or not recoverable tissue) therein. In an embodiment, the target tissue is established, at least in part, by the desired outcome for a particular wound and its ability to heal with such intervention. In an embodiment, the robotic debridement apparatuses are configured to discern between viable and nonviable tissue, and appropriately engage with at least one tissue thereof (e.g., debriding nonviable tissue or providing one or more agents to assist in healing viable tissue). In an embodiment, the body region can include at least a portion of a head, a face (e.g., an ear, a nose, or a mouth), a neck, a chest, a stomach, a back, a waist, a hip, a groin, a buttocks, a thigh, a knee, a calf, a shin, a foot (e.g., an ankle, a sole, toes), an upper limb (e.g., an arm), a forearm, an elbow, a wrist, a hand, fingers, etc.

In an embodiment, at least one of the robotic debridement apparatuses can be configured to debride at least one target tissue in the wound region. The target tissue can be a selected tissue or a portion of the selected tissue to be debrided. For example, the at least one target tissue in the wound region that can be debrided by the robotic debridement apparatuses disclosed herein can include at least one of necrotic tissue (e.g., eschar, dead cells, or cellular debris), ischemic tissue, slough (e.g., separated tissue, fibrin, and proteinaceous material), granulation tissue (e.g., hypergranulation tissue), fibrinous tissue, connective tissue, epithelial tissue, endothelial tissue, or another suitable tissue. For example, target tissue in a wound can be debrided to remove at least a portion of dead, devitalized, or contaminated tissue, as well as foreign material, from a wound, thereby reducing microbes, toxins, and other substances that inhibit healing.

In an embodiment, the robotic debridement apparatuses disclosed herein can be used in cosmetic procedures. For example, the robotic debridement apparatuses disclosed herein can be used to debride a target tissue. For example, a target tissue can be scar tissue, pigmented tissue, wrinkled tissue, infected tissue, damaged tissue, or any portion thereof. The robotic debridement apparatuses can be used in any suitable cosmetic procedure, such as cosmetic surgery, a cosmetic peel treatment (e.g., an acne peel), a dermabrasion treatment, or another suitable cosmetic procedure. As such, the body region can include a skin surface, a skin graft, a scar, a wound region, a skin depression, or another portion of the subject.

Thus, in certain instances, the target tissue consists solely of nonviable or dead tissue that is desired to be debrided, and in certain other instances the target tissue consists solely of viable tissue (healthy, unaffected and recoverable tissue) that is desired to be debrided (e.g., pigmented skin), and in certain instances the target tissue has both viable and nonviable tissue, and the apparatuses are directed to remove one or the other, or both.

In an embodiment, the robotic debridement apparatuses disclosed herein can be used in any application that debrides tissue from a body region, captures substances from the body region, or provides a therapeutic effect to the body region.

I. Robotic Debridement Apparatuses

FIG. 1 is a schematic illustration of a robotic debridement apparatus 100, according to an embodiment. The robotic debridement apparatus 100 is configured to facilitate debridement of tissue (e.g., target tissue) from a body region. The robotic debridement apparatus 100 includes a housing 102 that at least one of supports, encloses, or protects one or more components of the robotic debridement apparatus 100. For example, the robotic debridement apparatus 100 includes at least one locomotive mechanism 104 positioned in or on the housing 102. The at least one locomotive mechanism 104 is configured to provide a propelling force (e.g., self-propelling locomotive force) to the robotic debridement apparatus 100 to effect locomotion (e.g., movement, travel) of the robotic debridement apparatus 100. The robotic debridement apparatus 100 includes a device positioned in or on the housing 102 that is configured to facilitate debridement of tissue from a body region. For example, in the illustrated embodiment, the robotic debridement apparatus 100 includes at least one debriding tool 106 configured to debride the tissue from the body region. For example, the debriding tool 106 can be configured to debride at least one target tissue of the body region. The at least one debriding tool 106 can include any of the debriding tools 306a-o shown in FIGS. 3A-3O. Additionally or alternatively, the robotic debridement apparatus 100 can include at least one debris disposal device (e.g., any of the debris disposal devices 452a-j of FIGS. 4A-4J) configured to capture at least one substrate from the body region. In embodiments, the robotic debridement apparatus 100 can further include at least one therapeutic device (e.g., any of the therapeutic devices 562a-b of FIGS. 5A-5B) configured to provide a therapeutic effect to the body region. In some embodiments, the robotic debridement apparatus 100 can include at least one of one or more sensors 108, at least one power source 110, or at least one controller 112 positioned in or on the housing 102, any of which are optional in some embodiments.

In an embodiment, any component or electronic of the robotic debridement apparatus 100 can be manufactured using an additive manufacturing process. Non-limiting examples of additive manufacturing processes include liquid-based processes (e.g., stereolithography, jetted photopolymer, and ink jet printing), powder-based processes (e.g., selective laser sintering, direct metal laser sintering, and three-dimensional printing), and solid-based processes (e.g., laminated object manufacturing or fused deposition modeling).

A. Housings

As discussed above, the housing 102 of the robotic debridement apparatus 100 is configured to have one or more components of the robotic debridement apparatus 100 positioned therein or thereon. For example, the housing 102 can be configured to at least one of support, protect, or shelter the one or more components of the robotic debridement apparatus 100. The one or more components of the robotic debridement apparatus 100 can be mounted to, partially enclosed by, incorporated into, or positioned within the housing 102. The one or more components of the robotic debridement apparatus 100 can include at least one of the locomotive mechanism 104, the debriding tool 106, the debris disposal device, the therapeutic device, the sensors 108, the power source 110, the controller 112, any other device disclosed herein, or any other suitable device.

The housing 102 can include at least one outer surface 116. For example, the housing 102 can include at least one of a plate-like structure, a framed structure, a two-dimensional structure, or a three-dimensional structure (e.g., a three-dimensional structure at least partially enclosing a space). For example, the robotic debridement apparatus 100 can include one or more components that would be adversely affected (e.g., damaged) if exposed to the body region. As such, the housing 102 can include a three-dimensional structure or another suitable structure that encloses and substantially isolates the one or more components from the body region. In an embodiment, the housing includes a water-tight structure. In an embodiment, the housing 102 can include two or more portions that are configured to move relative to each other. For example the two or more portions can be operably coupled to the locomotive mechanism 104 and connected together using one or more of a joint, a bearing, etc. For example the two or more portions can be operably coupled to the debriding tool 106.

In an embodiment, the housing 102 exhibits a longitudinal axis 118. The housing 102 can exhibit a maximum length that is measured along the longitudinal axis 118. The maximum length of the housing 102 can be about 1 μm to about 10 cm, such as about 1 μm to about 2 cm, 1 μm to about 500 μm, about 100 μm to about 1 mm, about 500 μm to about 2 mm, about 1 mm to about 2 cm, about 5 mm to about 5 cm, or about 1 cm to about 10 cm. The length of the housing 102 can be selected based on one or more of the type of locomotive mechanism 104 positioned in or on the housing, the size of the body region, the number of robotic debridement apparatuses positioned on the body region, the type of debriding tool 106 positioned in or on the housing 102, the type of debris disposal device positioned in or on the housing 102, the type of therapeutic device positioned in or on the housing 102, whether the robotic debridement apparatus is associated with a dressing, etc.

In an embodiment, the housing 102 exhibits a shape compatible with interfacing with a tissue. For example, the housing 102 can exhibit a capsular design. For example, the housing 102 can be generally cylindrical or spherical. For example, the housing 102 can be generally rectangular or another suitable polyhedron. In an embodiment, the housing 102 can include a plurality of segments (e.g., first and second segments 211a, 213a of FIG. 2A). For example, the segments can be coupled smoothly or can be coupled by a bellows or a joint. For example, the segments can be coupled in a telescoping configuration. In an embodiment, the housing 102 can include at least one three-dimensional printed micropillar structure.

In an embodiment, at least a portion of the housing 102 (e.g., the outer surface 116 of the housing 102) can be at least partially formed from or coated with one or more biocompatible materials. For example, at least a portion of the housing 102 can be formed from a biocompatible material such as stainless steel, titanium or a titanium alloy, ceramic, polymethylmethacrylate (PMMA), poly(tetrafluoroethylene) (PTFE), etc. For example, at least a portion of the housing 102 can be formed with a nanotextured surface. In an embodiment, at least a portion of the housing 102 (e.g., the outer surface 116 of the housing 102) can be coated with one or more biocompatible materials and/or bioactive coating. For example, at least a portion of the housing 102 can be coated with biocompatible materials including a polymer, biopolymer, or silicon. For example, at least a portion of the housing 102 can be coated with a biocompatible material chosen for its lubricity properties, friction properties, hydrophobicity/hydrophilicity properties, or moisture-resistant properties (e.g., vinylpyrrolidone-butylmethacrylate compounds, zylalene polymers, etc.). In an embodiment, at least the outer surface 116 of the housing 102 can be at least partially formed from or coated with a material that facilitates the debridement of tissue (e.g., at least one target tissue). For example, the outer surface 116 of the housing 102 can include copper, silver, or another material which exhibits antimicrobial properties. For example, the outer surface 116 of the housing 102 can include a bioactive coating including a polymer comprising a debriding agent or therapeutic agent, as described herein. For example, the outer surface 116 of the housing 102 can include or be coated with an abrasive or chemical compound, as described herein. For example, the outer surface 116 of the housing 102 can include or be coated with a gel, hydrogel, colloid, or hydrocolloid (e.g., a gel or fluid comprising an abrasive or chemical compound).

In an embodiment, the housing 102 can be a freestanding housing. For example, a freestanding housing includes a housing that is not actively supported by another structure (except for devices positioned in or on the housing 102, e.g., the locomotive mechanism 104), while the robotic debridement apparatus 100 is operating within the body region. As such, the entire robotic debridement apparatus 100 can be free to operate in at least two degrees of freedom (e.g., at least three, at least four, at least five, or six degrees of freedom) during operation. In particular, the freestanding housing can move in two or more of forwards/backwards, left/right, or up/down during operation. It is noted that the another structure would be considered to actively support the housing 102 during operation when the another structure continuously supports at least 20% of the weight of the housing 102, restricts movement of the robotic debridement apparatus 100 to a significantly small portion of the body region, or the housing 102 is directly coupled (e.g., attached) to another device that does not travel within the body region or restricts the ability of the robotic debridement apparatus's 100 to travel in at least two of forward/backward, left/right, or up/down. For example, the housing 102 can be freestanding if indirectly connected to another structure via at least one tether having slack therein during operation of the robotic debridement apparatus 100. In an embodiment, the housing 102 is not freestanding (e.g., housing 2202 of FIG. 22).

In an embodiment, at least a portion of the robotic debridement apparatus 100 can be disposable or reusable. When at least a portion of the robotic debridement apparatus 100 is reusable, at least one of the reusable portions of the robotic debridement apparatus 100 can be configured to be cleaned between uses (e.g., configured to be sterilized, disinfected, etc.). In an embodiment, the housing 102 can be reusable. In such an embodiment, the housing 102 can be configured to protect at least one other reusable portion of the robotic debridement apparatus 100 that can be damaged during the cleaning process (e.g., the locomotive mechanism 104 or the controller 112). In such an embodiment, the housing 102 can be configured to have the other reusable portion of the robotic debridement apparatus 100 removed therefrom during the cleaning process (e.g., the housing 102 opens, the other reusable portion is reversibly coupled to the housing 102, etc.).

B. Locomotive Mechanisms

As discussed above, the at least one locomotive mechanism 104 is configured to move the robotic debridement apparatus 100 within the body region. For example, the locomotive mechanism 104 can be configured to induce a self-propelling locomotive force. The self-propelling locomotive force can induce a rolling motion, a crawling motion, a walking motion (e.g., with leg-like protrusions), an inchworm-like motion, an earthworm-like motion or another suitable motion. In an embodiment, the locomotive mechanism 104 can be configured to move the robotic debridement apparatus 100 responsive to direction from the controller 112. In an embodiment, the locomotive mechanism 104 can be configured to move the robotic debridement apparatus 100 in a generally linear path, a random path, etc. In an embodiment, the locomotive mechanism 104 can controllably move the robotic debridement apparatus 100 responsive to direction from the controller 112. For example, the locomotive mechanism 104 can controllably move the robotic debridement apparatus 100 along a selected path responsive to the direction from the controller 112.

In an embodiment, any of the locomotive mechanisms disclosed herein can include one or more actuators (e.g., actuators 150) configured to cause the locomotive mechanisms to move. For example, the actuators can include squiggle motors, inchworm actuators, piezoelectric materials (e.g., piezoelectric inchworm motor, piezoelectric bending actuator, piezoelectric unimorph, piezoelectric bimorph, piezoelectric motor, piezoelectric transducer), motors (e.g., DC motors, brushless motors), electromagnetic actuators, electrostatic actuators, pumps, fluid compressors, bending actuators, unimorph actuators, bimorph actuators, microactuators (e.g., micromotors), screws, or two-way linear actuators. In addition, the actuators 150 can be formed from shape memory alloys or ionic polymer metal components. In an embodiment, actuators include microelectromechanical systems or another suitable actuator. In an embodiment, the actuators can include any suitable actuator. The actuators disclosed herein can be used in any of the locomotive mechanisms, robotic debridement apparatuses, or system embodiments disclosed herein.

Referring to FIG. 1, the locomotive mechanism 104 includes at least one impelling mechanism 105 at least partially extending from the housing 102c. The impelling mechanism 105 is configured to engage a surface 107 of the body region 109 and provide locomotion to the robotic debridement apparatus 100. For example, the impelling mechanism 105 can include one or more appendages, legs, or wheels, with or without adhesive aspects (e.g., adhesive microvilli, three-dimensional printed micropillar structures). The locomotive mechanism 104 can include one or more actuators 150 that are configured to drive the impelling mechanism 105.

In an embodiment, the impelling mechanism 105 includes jointed appendages or legs that can be actuated to propel the robotic debridement apparatus 100 forward in a walking or crawling motion. For example, the impelling mechanism 105 can include a slot-follower mechanism driven via a lead screw to provide a propulsive force to a jointed leg. In an embodiment, multiple jointed legs (e.g., of superelastic, shape memory, polymer, or other material) can be motivated to interact with the body region 109 under control of the actuators 150. For example, appendages or legs can be formed from a shape memory alloy or ionic polymer metal component that is driven by the application of a stimulus (e.g., current, thermal energy, etc.).

In an embodiment, the impelling mechanism 105 configured to provide movement in a particular direction. For example, the impelling mechanism 105 can be configured so that only a portion of a plurality of appendages (e.g., one or more legs) is actuated, while other portions of the plurality of appendages remain stationary. As such, the impelling mechanism 105 can induce movement (e.g., locomotion) that drives a change in direction (e.g., left, right, forward, backward, etc.), and allows the robotic debridement apparatus 100 to be controllably steered.

In an embodiment, the locomotive mechanism 104 includes one or more arrays of impelling mechanisms (not shown). For example the locomotive mechanism 104 can include an array of impelling mechanisms aligned along an x-axis and a second array of impelling mechanisms aligned along a y-axis. For example, the locomotive mechanism 104 can include actuators 150 and accelerometers (not shown) that allow the robotic debridement apparatus 100 (e.g., a sphere) to roll in any direction under direction of the controller 112.

FIGS. 2A-2G are schematic illustrations of robotic debridement apparatuses including different locomotive mechanisms, according to different embodiments. Except as otherwise described herein, the robotic debridement apparatuses shown in FIGS. 2A-2G and their materials, components, or elements can be similar to or the same as the robotic debridement apparatus 100 (FIG. 1) and its respective materials, components, or elements. For example, the robotic debridement apparatuses shown in FIGS. 2A-2G can include at least one of a housing, at least one locomotive mechanism, at least one tissue debriding tool (e.g., any of tissue debriding tools 306a-o of FIGS. 3A-3O), at least one debris disposal device (e.g., any of the debris disposal devices 452a-j of FIGS. 4A-4J), at least one therapeutic device (e.g., any of the therapeutic devices 562a-b of FIGS. 5A-5B), one or more sensors, a controller, or a power source. Any of the locomotive mechanisms illustrated in FIGS. 1, 2A-2G can be used in any of the robotic debridement apparatus embodiments disclosed herein.

Figure 2A:
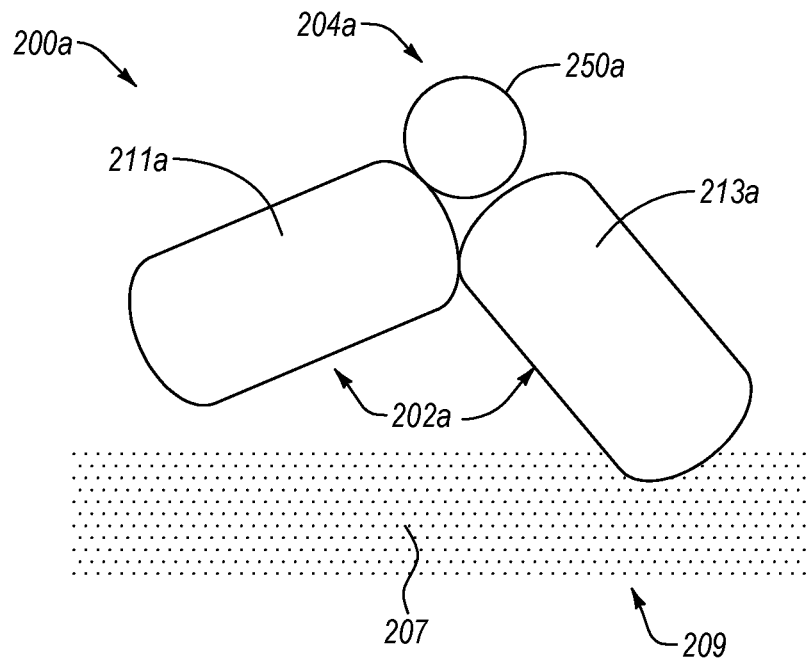
FIGS. 2A-2G are schematic illustrations of robotic debridement apparatuses including different locomotive mechanisms, according to different embodiments.

Referring to FIG. 2A, the robotic debridement apparatus 200a includes at least one locomotive mechanism 204a having at least one inchworm-like motive mechanism (e.g., a stick and slip mechanism). For example, the robotic debridement apparatus 200a can include a housing 202a that is formed from a plurality of segments. For example, the housing 202a can be formed from at least a first segment 211a and a second segment 213a. The first and second segments 211a, 213a can be jointed together such that the first and second segments 211a, 213a are moveable relative to each other. The locomotive mechanism 204a can include one or more actuators 250a that are operably coupled to the first and second segment 211a, 213a and configured to move the first and second segments 211a, 213a relative to each other. As such, the one or more actuators 250a can drive each of the first and second segments 211a, 213a in an inchworm-like manner. For example, the actuators 250a can cause the first and second segments 211a, 213a to intermittently engage and disengage from a surface 207 of the body region 209 thereby traversing a distance.

Figure 2B:
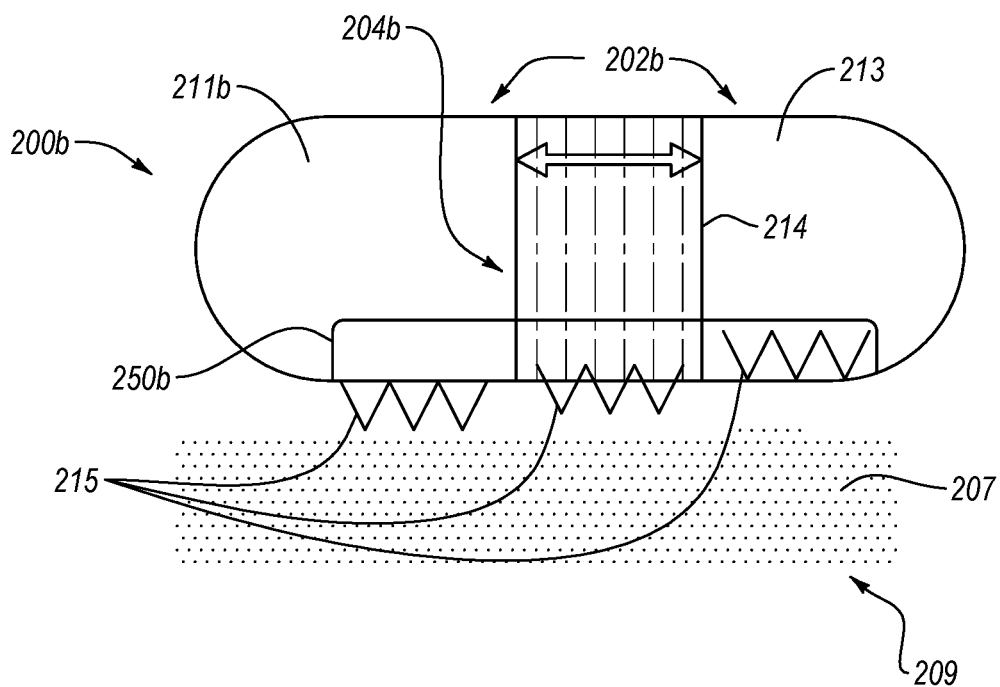

Referring to FIG. 2B, a robotic debridement apparatus 200b includes at least one locomotive mechanism 204b having at least one earthworm-like motive mechanism (e.g., stick and slip mechanism). In an embodiment, the robotic debridement apparatus 200b can include a housing 202b that includes a plurality of segments (e.g., first and second segments 211b, 213b). The locomotive mechanism 204b can also include at least one bellows 214 coupled to and extending between two of the plurality of segments. The bellows 214 can be a pneumatic bellows or another suitable bellows. The bellows 214 can be configured to expand (e.g., move the first and second segments 211b, 213b away from each other) and contract (e.g., move the first and second segments 211b, 213b closer together).

The locomotive mechanism 204b can also include at least one engaging element 215 (e.g., retractable elements) that reversibly engage and disengage from a surface 207 of the body region 209. For example, the engaging elements 215 can include protrusions, three-dimensional printed micropillar structures, etc. The locomotive mechanism 204b can also include one or more actuators 250b. At least one of the actuators 250b can be coupled to the engaging element 215 and configured to controllably extend or retract the at least one engaging element 215 from housing 202b. As such, the engaging element 215 can cause the robotic debridement apparatus 200b to displace along a surface of the body region, thereby traversing a distance.

Figure 2C:
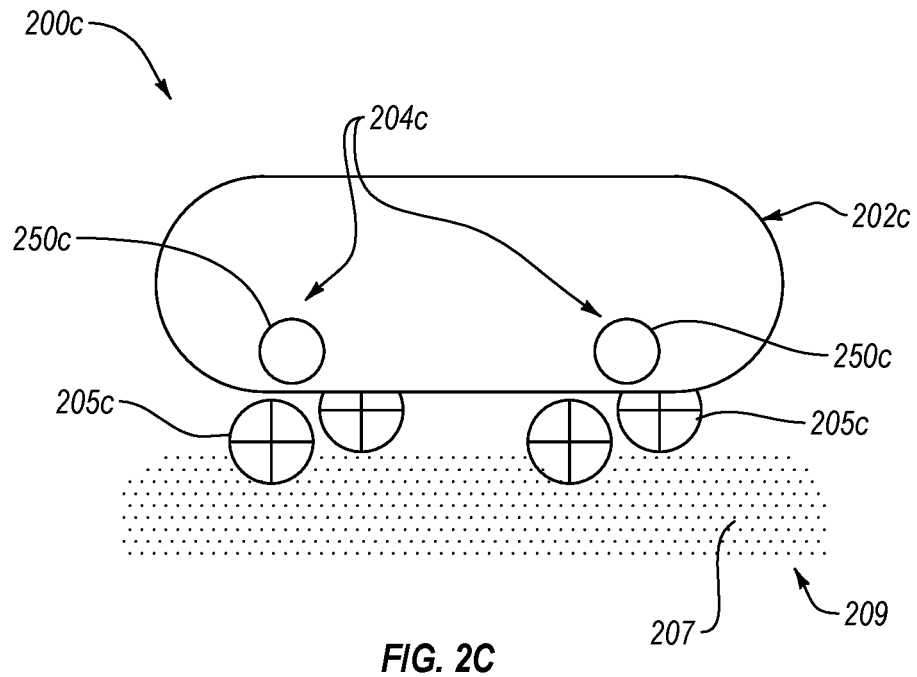

Referring to FIG. 2C, a robotic debridement apparatus 200c includes at least one locomotive mechanism 204c having at least one impelling mechanism 205c. The impelling mechanism 205c at least partially extends from the housing 202c and is configured to engage a surface 207 of the body region 209 to provide locomotion to the robotic debridement apparatus 200c. The impelling mechanism 205c can include one or more wheeled appendages, such as 1, 2, 3, 4, 5, 6, or more than six wheeled appendages. The locomotive mechanism 204c can also include one or more actuators 250c. At least one of the actuators 250c can be coupled to at least one of the wheeled appendages of the impelling mechanism 205c. The one or more actuators 250c can be configured to drive the wheeled appendages to provide locomotion to the robotic debridement apparatus 200c.

Figure 2D:
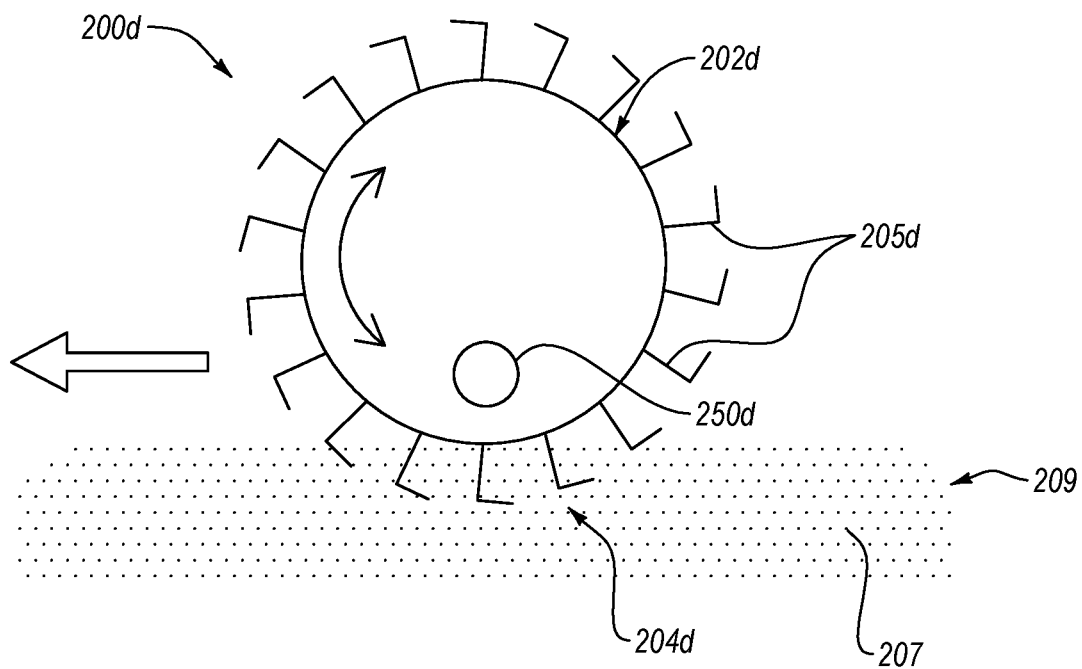

Referring to FIG. 2D, a robotic debridement apparatus 200d includes at least one locomotive mechanism 204d having at least one impelling mechanism 205d. The impelling mechanism 205d at least partially extends from the housing 202d and is configured to engage a surface 207 of the body region 209 to provide locomotion to the robotic debridement apparatus 200d. For example, the impelling mechanism 205d can include a plurality of appendages (e.g., legs, protrusions, hooks, three-dimensional printed micropillar structures, or other surface-engaging elements) configured to engage the surface 207 and propel the robotic debridement apparatus 200d forward. In an embodiment, the housing 202d can be cylindrical or spherical in shape and can roll along the surface 207 of the body region 209. For example, the locomotive mechanism 204d can include one or more actuators 250d configured to roll the robotic debridement apparatus 200d along the surface 207. In an embodiment, the appendages can act to engage the body region 209 driven by rotational forces to provide locomotion.

Figure 2E:
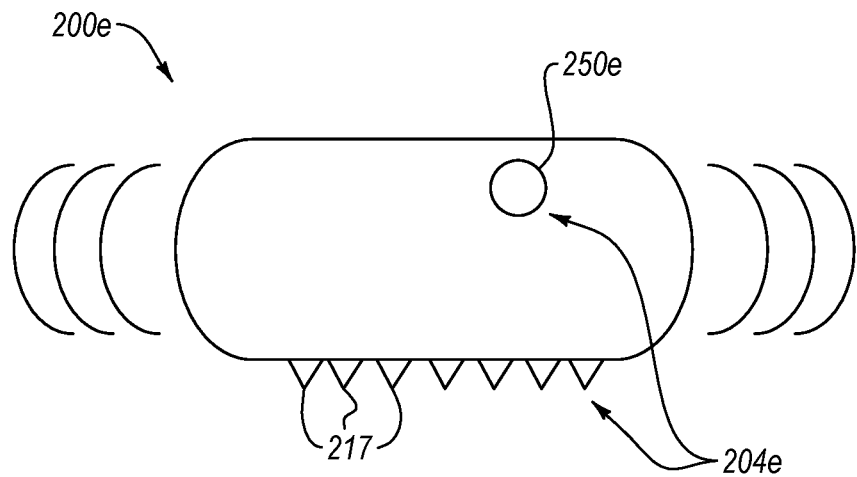

Referring to FIG. 2E, a robotic debridement apparatus 200e can include a locomotive mechanism 204e. The locomotive mechanism 204e can include a vibratory mechanism. For example, the vibratory mechanism can include one or more actuators 250e configured to vibrate the robotic debridement apparatus 200e. In an embodiment, the actuators 250e can be configured to induce directional movement. The direction that the robotic debridement apparatus 200e travels (e.g., moves) can be controlled by the excitation frequencies of the actuators 250e.

In an example, the actuators 250e can include at least one piezoelectric material. The piezoelectric material can form part of a piezoelectric bending actuator, a piezoelectric unimorph, a piezoelectric bimorph, or a piezoelectric microactuator. The piezoelectric material can induce movement in the robotic debridement apparatus 200e when the piezoelectric material is activated by an electrical signal, thereby inducing movement in one or more components of the locomotive mechanism 204e (e.g., legs, appendages, etc.) or in the entire robotic debridement apparatus 200e. In another example, the actuators 250e include a unimorph actuator or a bimorph actuator. In another example, the actuators 250e can include two-way linear actuators using springs made from a shape memory alloy. In another example, the actuators 250e can include a micromotor. In another example, the actuators 250e can include any other suitable actuator disclosed herein In embodiments, the locomotive mechanisms 204e disclosed herein can include friction enhancements 217 on the housing 202e or on another component of the robotic debridement apparatus 200e. The friction enhancements 217 can include at least one of one or more surface-engaging protrusions, microprotrusions, setae, microvilli, or adhesive microvilli. In an embodiment, the friction enhancements 217 can include at least one three-dimensional printed micropillar structure. In an embodiment, at least a portion of the friction enhancements 217 can include micro-patterning formed on the surface of the housing 202e or another component of the robotic debridement apparatus 200e. The friction enhancements 217 can improve the efficiency of the movement of the robotic debridement apparatus 200e when the robotic debridement apparatus is moved by the vibratory mechanism. It is noted that the friction enhancements 217 can also improve the efficiency of movement of any of the robotic debridement apparatuses disclosed herein.

Figure 2F:
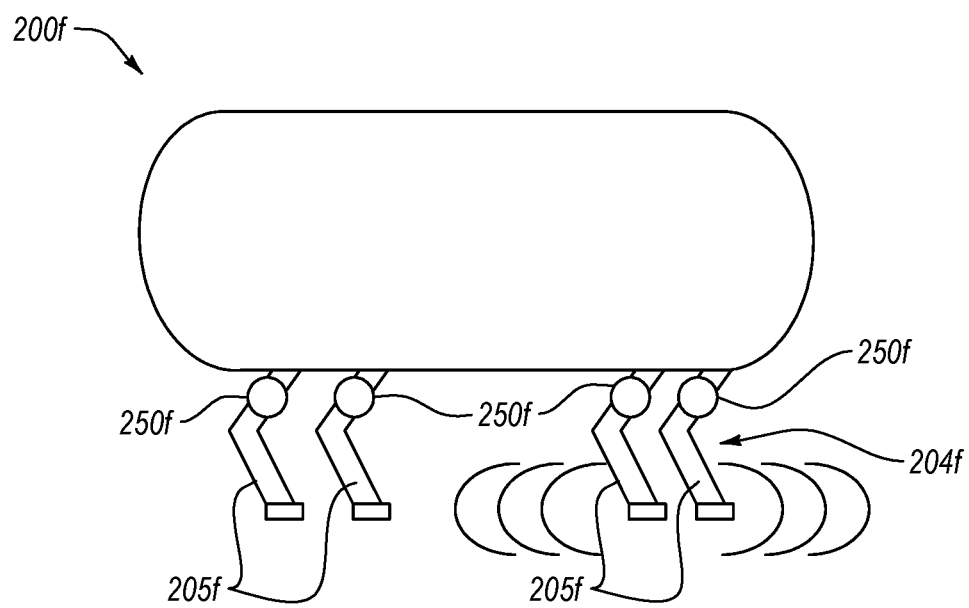

Referring to FIG. 2F, a robotic debridement apparatus 200f can include a locomotive mechanism 204f including an impelling mechanism 205f. The impelling mechanism 205f can be similar to any of the impelling mechanisms disclosed herein. The locomotive mechanism 204f can also include one or more actuators 250f that are configured to vibrate at least a portion of the robotic debridement apparatus 200f. For example, the actuators 250f can be configured to vibrate at least a portion of the impelling mechanism 205f. The vibrations from the actuators 250f can provide locomotion to the robotic debridement apparatus 200f.

Figure 2G:
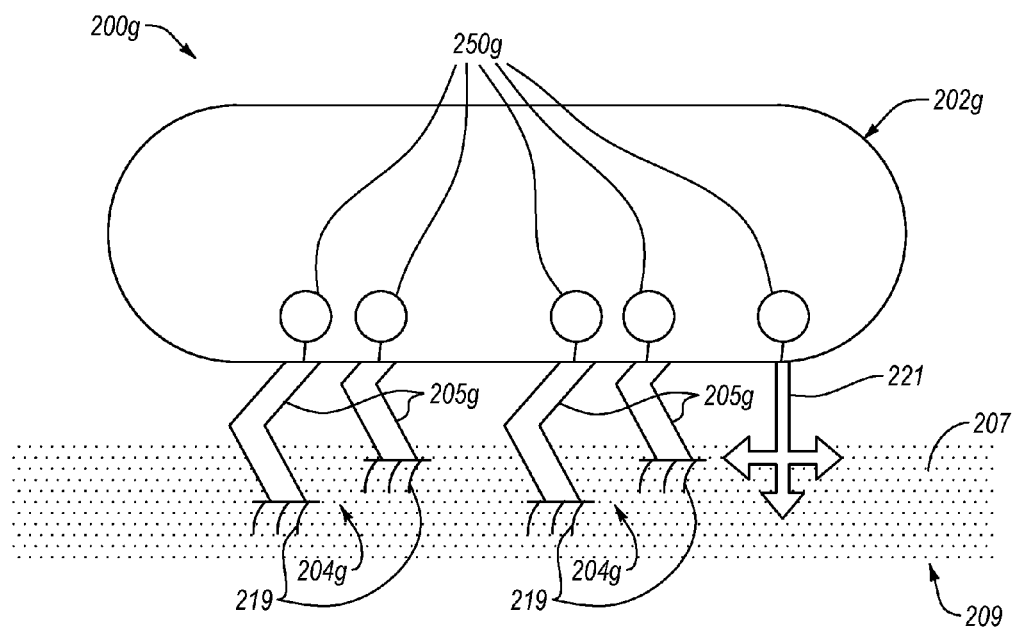

Referring to FIG. 2G, the robotic debridement apparatus 200g can be configured to touch, grasp, grip, or otherwise engage tissue on the body region 209. In an embodiment, the robotic debridement apparatus 200g includes at least one locomotive mechanism 204g having an impelling mechanism 205g. The impelling mechanisms 205g can be similar to any of the impelling mechanisms disclosed herein. The impelling mechanism 205g can include one or more grippers or graspers 219. The grippers or graspers 219 can be configured to controllably engage (e.g., touch, grasp, grip, hook, suction, etc.) and disengage a surface 207 of the body region 209. For example, the grippers or graspers 219 can include protrusions, three-dimensional printed micropillar structures, microvilli, etc. The grippers or graspers 219 can be operably coupled to one or more actuators 250g that are configured to cause the grippers or graspers 219 to controllably engage or disengage from the surface 207. In an embodiment, the grippers and graspers 219 can be used when the robotic debridement apparatus 200e is debriding tissue from the body region 209, disposing of at least one substance from the body region 209, or providing a therapeutic effect to the body region 209.

In an embodiment, the robotic debridement apparatus 200g can include at least one anchor 221 positioned in or on the housing 202g that is configured to controllably maintain the robotic debridement apparatus 200g in substantially the same location for a selected period of time. For example, the anchor 221 can include a harpoon or hook that engages the body region 209. For example, the anchor 221 can include a suction device that is operably coupled to and configured to be suctioned to the body region 209 or a dressing (e.g., dressing 1178 of FIGS. 11A-11B). The suction device can include a pump, compressor, etc. operably coupled to the body region 209 and configured to controllably provide a suction force that secures the robotic debridement apparatus 200g in substantially the same location. In an embodiment, the anchor 221 can be used when the robotic debridement apparatus 200g is debriding tissue from the body region 209, disposing of at least one substance from the body region 209, or providing a therapeutic effect to the body region 209.

It is understood that the locomotive mechanisms disclosed herein can include locomotive mechanisms other than the locomotive mechanisms shown in FIGS. 1-2G. For example, a locomotive mechanism (e.g., locomotive mechanism 2004 of FIG. 20) can include a magnet positioned in or on the housing 102. Another device (e.g., the dressing 2078 of FIG. 20) can include a magnetic field generator (e.g., magnetic field generator 2099 of FIG. 20) positioned therein or thereon configured to generate a magnetic field that exerts a force on the magnet of the locomotive mechanism 104 to effect movement of the robotic debridement apparatus 100. For example, the robotic debridement apparatus 100 can include a spherical housing (e.g., FIG. 2D) able to roll under the magnetic force generated by the magnetic field generator.

Referring back to FIG. 1, in an embodiment, the locomotive mechanism 104 can be reusable. For example, the locomotive mechanism 104 can be configured to be cleaned (e.g., sterilized, disinfected, etc.) between uses. In an embodiment, the locomotive mechanism 104 can be reversibly coupled to the housing 102, for example, to facilitate cleaning of the locomotive mechanism 104.

In an embodiment, the locomotive mechanism 104 can include a plurality of locomotive mechanisms. In an embodiment, at least some of the plurality of locomotive mechanisms can be the same. In an embodiment, at least some of the plurality of locomotive mechanisms can be different. For example, at least some of the locomotive mechanisms can be similar to the locomotive mechanism 104 (FIG. 1) and at least some of the locomotive mechanisms can be similar to the locomotive mechanism 204c (FIG. 2C)

In embodiments, the locomotive mechanism 104 can be omitted. For example, the locomotive mechanism 104 can be omitted in embodiments where the robotic debridement apparatus 100 is attached to a dressing (FIG. 22).

C. Sensors

Referring still to FIG. 1, the robotic debridement apparatus 100 includes one or more sensors 108 configured to detect one or more characteristics of the body region or a substance thereon. For example, the sensors 108 can be positioned on the outer surface 116 of the housing 102, or another portion of the housing 102 that enables the sensors 108 to detect (e.g., sense, quantify, etc.) one or more characteristics of the body region or substance. For example, the sensors 108 can be positioned on a surface-engaging element or the impelling mechanism 105.

In an embodiment, the sensors 108 can be configured to detect at least one target tissue or another tissue that is intended for treatment. For example, the sensors 108 can be configured to detect at least one of necrotic tissue, nonviable tissue, viable tissue, slough, fibrinous tissue, ischemic tissue, granulation tissue, connective tissue, epithelial tissue, endothelial tissue, or any other type of tissue. For example, the sensors 108 can detect inflammation, microbes, or toxins. In an embodiment, the sensors 108 can be configured to detect one or more indicators that can indicate healthy, viable tissue; tissue in a state of disease or disorder; or nonviable, dying or dead tissue. Indicators can include, for example and without limitation, peptides, proteins, lipids, saccharides, cell markers, inflammatory markers, microbes, toxins, or any other suitable indicator. In an embodiment, the sensors 108 can be configured to detect one or more fluids released into the body region by at least one robotic debridement apparatus positioned in the body region. For example, the sensors 108 can be configured to detect one or more debriding agents, one or more therapeutic agents, or one or more taggants.

In an embodiment, the sensors 108 can include at least one chemical sensor. For example, the chemical sensor can include an electrochemical sensor or cantilever chemical sensor. For example, the chemical sensor can include a pH sensor configured to detect differences in pH. For example, the pH sensor can be configured to detect different pH levels between at least two distinct regions of the body region or at least two types of tissue (e.g., necrotic tissue and viable tissue). In an embodiment, the chemical sensor can include a protein sensor. For example, the protein sensor can be configured to detect a heat shock protein, calreticulin, or other proteins present in necrotic tissue. In an embodiment, the chemical sensor can include a sensor configured to detect one or more chemicals released by viable tissue or by nonviable tissue. For example, the sensor can be configured to detect one or more chemical present in necrotic tissue, such as cytochrome c, galactosidase, high-mobility group protein B1 (HMGB1), glyceraldehyde 3-phosphate dehydrogenase, vimentin, lamin A, soluble galactose-binding lectin 7, or collagen. In an embodiment, the sensor 108 can be configured to detect one or more chemicals present in viable tissue, such as fibronectin 1, serine protease inhibitor 2b, transferrin, or hemoglobin.

In an embodiment, the chemical sensor can include a gas sensor. For example, the gas sensor can be configured to detect gases (e.g., volatile organic chemicals) released by unhealthy tissue, healthy tissue, or one or more taggants present in the body region. For example, the gas sensor can be an acoustic wave sensor, piezoelectric sensor, or electronic nose sensor. In an embodiment, the chemical sensor can include a peroxide sensor (e.g., hydrogen peroxide sensor), a nitric oxide sensor, or a nitrate sensor. In an embodiment, the sensors 108 can include at least one optical sensor. In an embodiment, the optical sensor can include a light sensor configured to detect different colors. For example, the light sensor can include a spectrophotometer and a light source. The light source can include a light-emitting diode, a white light source, or a light source configured to provide light in at least one of a variable or specific wavelength, such as infrared wavelength or ultraviolet wavelength. Such a light sensor can be used to distinguish nonviable tissue from viable tissue. For example, the light sensor can distinguish between at least two of necrotic tissue (e.g., typically dark or black), slough (e.g., typically white or yellow), fibrinous tissue (e.g., typically white or yellow), healthy granulation tissue (e.g., typically pink or red), unhealthy granulation tissue (e.g., typically dark red), or healthy new tissue (e.g., typically pink). For example, the light sensor can distinguish between intact tissue (e.g., intact skin) and a wound. In an embodiment, the light sensor can detect cellular autofluorescence. In an embodiment, the light sensor can detect one or more taggants. For example, the taggant can include a dye, a fluorescent tag, etc. For example, the taggant can include an agent with a binding moiety and a moiety having optical properties, such as a chromogen, fluorescent agent, luminescent agent, a quantum dot, or an agent with an alterable optical density.

In an embodiment, the sensors 108 include at least one radiological sensor. For example, the sensors 108 can include a CMOS imager with aptamer functionalization to detect the presence of radio-labeled target biomolecules. In an embodiment, the sensors 108 include at least one electrical sensor. For example, the sensor 108 can include a sensor able to detect an electrical charge. For example, the sensor 108 can include a transducer able to generate a signal in response to an electrical charge.

In an embodiment, the optical sensor can include a topographical sensor configured to detect the topography of at least a portion of the body region. For example, the topography of the body region can be used to determine vascularization, grooves, pores, rough sections of the body region, wet sections of the body region, shiny regions of the body region, etc. For instance, vascularization can indicate healthy tissue, rough sections of the body region can indicate hypergranulation tissue, and wet or shiny sections of the body region can indicate fibrinous tissue. In another example, the topography of the body region can be used to detect an indentation that the robotic debridement apparatus 100 forms in the body region (e.g., the robotic debridement apparatus 100 would make a larger indentation in the relatively soft inflamed tissue than in the relative hard healthy tissue). In an embodiment, the optical sensor can include an optical scattering sensor configured to distinguish between necrotic, sloughing, and healthy tissue. In an embodiment, the optical sensor can include a near-infrared spectroscopy sensor. For example, the near-infrared spectroscopy sensor can detect the oxygenation levels of the tissue, which can be used, for example, to distinguish different types of tissue. In an embodiment, the optical sensor can include an optical coherence tomography sensor, a diffuse reflectance spectroscopy sensor, or a fluorescence spectroscopy sensor.

In an embodiment, the sensor 108 can include at least one acoustic sensor. For example, the acoustic sensor can include an acoustic transducer, (e.g., an ultrasound transducer). For example, the acoustic sensor can detect tissue density and different tissue densities can indicate different types of tissue. For example, the acoustic sensor can detect tissues with higher water content (e.g., healthy, viable tissues) and distinguish them from tissues with little or no water content (e.g., dry necrotic tissue).

In an embodiment, the sensors 108 can include at least one thermal sensor (e.g., bimetal, thermistor, thermocouple, resistance thermometer, etc.). For example, different types of tissue can exhibit different temperatures (e.g., necrotic tissue vs. non-necrotic tissue, inflamed tissue vs. non-inflamed tissue).

In an embodiment, the sensors 108 can include at least one electrical conductivity sensor. For example, different types of tissue can exhibit different conductivities. In an embodiment, the sensors 108 can include at least one moisture sensor configured to detect moisture. For example, a dry necrotic wound can exhibit a low moisture content, healthy tissue can exhibit a higher moisture content than the dry necrotic wound, while fibrinous tissue can exhibit an even higher moisture content than the healthy tissue. For example, high levels of moisture can indicate slough or excess exudate. For example, a moisture sensor can distinguish between intact tissue (e.g., skin) having a low moisture contact and a wound having a higher moisture content.

In an embodiment, the sensors 108 can include at least one contact sensor configured to detect which portions of the robotic debridement apparatus 100 are contacting the body region. For example, soft, nonviable tissue might contact a larger portion of the robotic debridement apparatus 100 than the relatively harder healthy tissue. Other suitable contact sensors include force-displacement sensors that contact the body region, for example. The force-displacement sensors can measure tissue hardness, because relatively soft tissue requires a relatively lower force from the force-displacement sensor than relatively hard tissue in order to be indented to the same depth by the force-displacement sensor. Other suitable contact sensors include at least one force-displacement sensor that contacts the body region. The force-displacement sensor can measure tissue hardness because relatively soft necrotic tissue requires a relatively lower force from the force-displacement sensor than relatively hard healthy tissue to be indented to the same depth by the force-displacement sensor. In another example, the contact sensor can include a brush sensor (e.g., at least one three-dimensional printed micropillar structure) configured to sense a topography of a body region.

In an embodiment, the sensors 108 can include at least one location sensor configured to detect the position of the robotic debridement apparatus 100. For example, the at least one location sensor can include an electromagnetic sensor, a sound sensor, etc. The location sensor can be configured to determine a location thereof relative to one or more locations proximate to the robotic debridement apparatus 100, relative to one or more other robotic debridement apparatuses, relative to one or more taggants or physical markers added to the body region, one or more features of the body region, or one or more features of a dressing (e.g., dressing 1178 of FIGS. 11A-11B), etc. In an embodiment, the sensors 108 do not include a location sensor. In an embodiment, the sensor is a global positioning sensor.

In an embodiment, the sensors 108 can comprise a sensor array. For example, the sensors 108 can include a phased array. For example, the sensors 108 can include an array of optical sensors. For example, the sensors 108 can include an array of acoustic sensors. In an embodiment, the sensor array can be configured to determine one or more of a direction, a gradient, or a location.

In an embodiment, the sensors 108 can transmit one or more sensing signals. For example, the sensors 108 can transmit one or more sensing signals responsive to detecting the one or more characteristics of the body region. For example, the sensing signals can include data encoded therein indicating different types of tissue detected. For example, the sensing signals can include data encoded therein indicating the location of the different types of tissue relative to the robotic debridement apparatus 100, the presence and location of other robotic debridement apparatuses, the presence and location of different agents present in the body region, etc. In an embodiment, the sensors 108 can transmit the one or more sensing signals to one or more components of the robotic debridement apparatus 100 (e.g., the controller 112). In an embodiment, the sensors 108 can transmit the one or more sensing signals to a device distinct and separate from the robotic debridement apparatus 100 (e.g., the dressing 1178 of FIGS. 11A-11B, the external device 127, etc.). The device can use the transmitted signals to at least partially control the operation of the robotic debridement apparatus 100, display information related to the robotic debridement apparatus 100 (e.g., progress reports, errors, etc.), create electronic records, etc. In an embodiment, the sensors 108 can sense the characteristics or transmit the one or more sensing signals responsive to direction from the controller 112.

D. Controllers

As discussed above, the controller 112 of the robotic debridement apparatus 100 can be communicatively coupled to one or more components of the robotic debridement apparatus 100. For example, the controller 112 can be communicably coupled to at least one of the locomotive mechanism 104, the debriding tool 106, the debris disposal device (e.g., any of the debris disposal devices 452a-j of FIGS. 4A-4J), the therapeutic device (e.g., any of the therapeutic devices 562a-b of FIGS. 5A-5B), the sensors 108, the power source 110, etc. The controller 112 can include control electrical circuitry (e.g., memory 122, a transceiver 124, and a processor 126) configured to control all or at least one of the components that are communicably coupled to the controller 112. For example, the controller 112 can be configured to controllably activate the locomotive mechanism 104, thereby controllably relocating (e.g., moving) the robotic debridement apparatus 100. For example, the controller 112 can direct the locomotive mechanism 104 to controllably move the robotic debridement apparatus 100, for example, to travel to a selected portion of the body region (e.g., a portion of the body region having necrotic tissue) or in a specified manner (e.g., at a certain speed or in a certain pattern). In an embodiment, the controller 112 can be configured to controllably activate at least one of the debriding tool 106, the debris disposal device, or the therapeutic device, thereby controllably facilitating debridement of the body region.

In some embodiments, the controller 112 can be omitted from the robotic debridement apparatus 100. For example, the controller 112 can be located in a device distinct from and communicably coupled to the robotic debridement apparatus 100 (e.g., another robotic debridement apparatus, the dressing 1178 of FIGS. 11A-11B, etc.) or the controller 112 can be omitted entirely.

The controller 112 can be communicably coupled, either directly or indirectly, to one or more components of the robotic debridement apparatus 100. For example, the housing 102 can include wires or a wireless device (e.g., Bluetooth, Wi-Fi) that couples the controller 112 to the one or more components of the robotic debridement apparatus 100. Therefore, the controller 112 can be remote from at least one of the locomotive mechanism 104, the debriding tool 106, the debris disposal device, the therapeutic device, the sensors 108, or the power source 110. In an embodiment, the controller 112 can at least partially be positioned within or incorporated into at least one of the locomotive mechanism 104, the debriding tool 106, the debris disposal device, the therapeutic device, the sensors 108, or the power source 110.

The controller 112 can include the memory 122, or the memory 122 can be separate from and communicably coupled to the controller 112. The memory 122 can be configured to store one or more operational instructions therein. The memory 122 can include non-transitory memory, such as random access memory (RAM), read only memory (ROM), a hard drive, a disc, flash memory, other types of memory electrical circuitry, or other suitable memory. The operational instructions stored on the memory 122 can include a program configured to operate the robotic debridement apparatus 100, information about the robotic debridement apparatus 100 and the components thereof, information gathered by the robotic debridement apparatus 100 (e.g., from the sensors 108), or additional information.

In addition or alternative to the memory 122, the controller 112 can include a transceiver 124 configured to receive one or more operational instructions from or to a user or a program or transmit information therefrom. For example, the transceiver 124 can be communicably coupled to a device (e.g., computer, cellphone, etc.) that is spaced or remote from the transceiver 124. The transceiver 124 can then transmit the received operational instructions to at least one of a processor 126 or the memory 122 (e.g., the transceiver 124 is communicably coupled to at least one of the processor 126 or the memory 122). For example, the transceiver 124 can transmit information (e.g., sensing signals from the sensors 108 or operational instructions from the controller 112) to another robotic debridement apparatus or to a dressing.

In an embodiment, the transceiver 124 can transmit information to a central location (e.g., computer, cellphone) where information can be compiled, stored, or accessed. The central location may include a user interface that can display at least a portion of the information to a user (e.g., graph the healing of a wound, indicate that an infection was detected, etc.) and enable the user to communicate with the controller 112. In an embodiment, the transceiver 124 can transmit information to the user. The information transmitted to the user can include the sensing signals, the status of the robotic debridement apparatus 100, the amount or type of tissue to be debrided or already debrided, an assessment of "mapping" of the target tissue or body region of the subject, the status of a particular debridement program, an alert that something has gone wrong with the apparatus or with the program, a recommendation to change the program based on particular criteria (e.g., subject is in pain, tissue damage is greater or less than first thought, healing has occurred faster than anticipated, etc.), physiological data based on sensed signals, or other information related to the apparatus, the system, or the target tissue.

The processor 126 of the controller 112 can be configured to direct certain operations of the robotic debridement apparatus 100 according to the operational instructions. For example, the processor 126 can receive the operational instructions from the memory 122 or the transceiver 124. The operational instructions can include a program encoded therein that enables the controller 112, via the processor, to operate the robotic debridement apparatus 100 automatically (e.g., with little to no outside instructions).

In an embodiment, the controller 112 can be operably coupled to an external device 127 that is spaced from the housing 102. For example, the external device 127 can be wiredly or wirelessly coupled to the controller 112. In an embodiment, the external device 127 can include memory, at least one processor, a display, a user interface, or at least one input device (e.g., mouse, keyboard, touchscreen). For example, the external device 127 can include a computer, a laptop, a cellphone, a tablet, etc. For example, the external device 127 can include a body resident device. For example, the external device 127 might include a skin-resident, organ-resident, or conformable electronic (e.g., an epidermal electronic). For example, the external device 127 can include or utilize a body area network. The external device 127 can transmit one or more command signals to the controller 112. For example, the one or more command signals can include one or more user-directed commands encoded therein that at least partially supersede any program that is executed by the processor 126. As such, the user-directed commands can allow a user to remotely control at least one operation of the robotic debridement apparatus. In another example, the one or more command signals can include one or more new programs that are downloaded to and stored on the memory 122. The new programs can at least partially supersede or supplement any program previously or currently stored on the memory 122 or executed by the processor 126.

In an embodiment, the controller 112 can transmit one or more informational signals to the external device 127. The one or more information signals can include information related to the robotic debridement apparatus 100 encoded therein. For example, the one or more information signals can include at least one of one or more sensing signals detected by the sensors 108, the status of the robotic debridement apparatus 100 or one or more components thereof, etc., or other information as described herein, such as information related to the apparatus, the system, or the target tissue of the subject. The external device 127 can display at least a portion of information encoded in the information signals to the user (e.g., the subject, a healthcare worker, computer, or third party) using the display.

In an embodiment, the external device 127 includes at least one of a computing device or a network including electronic records. For example, the external device 127 can include information stored therein (e.g., an electronic medical record of the subject). In an embodiment, the one or more information signals can include information related to operation of the robotic debridement apparatus 100 in regards to the subject (e.g., the history of debriding the target tissue or sensed characteristics of the body region and tissue therein) that can be added to the electronic medical record.

In an embodiment, the external device 127 is omitted. In an embodiment, the controller 112 is omitted, and the external device 127 controls the operation of one or more components of the robotic debridement apparatus 100 (e.g., the robotic debridement apparatus 100 includes a transceiver that receives one or more operational instructions or one or more command signals from the external device 127).

E. Power Sources

The robotic debridement apparatus 100 can include at least one power source 110 coupled to and configured to supply electrical power to the one or more components of the robotic debridement apparatus 100. For example, the power source 110 can be coupled to at least one of the locomotive mechanism 104, the debriding tool 106, the debris disposal device (e.g., any of the debris disposal device 452a-j of FIGS. 4A-4J), the therapeutic device (e.g., any of the therapeutic devices 562a-b of FIGS. 5A-5B), the sensors 108, the controller 112, or another component of the robotic debridement apparatus 100. In an embodiment, the power source 110 can controllably supply electrical power to the one or more components responsive to, for example, direction from the controller 112.

In an embodiment, the power source 110 can include any device configured to store power (e.g., electrical power) therein. For example, the power source 110 can include at least one battery (e.g., a microbattery or thin-film battery) or at least one capacitor.

In an embodiment, the power source 110 can include a device that is rechargeable. In an embodiment, as will be discussed in more detail later, the power source 110 can include a power receiver (e.g., power receiver 1998 of FIG. 19) configured to receive power (e.g., wirelessly or wiredly) from an external power source. The received power can then be stored in the power source 110 or transmitted to one or more components of the robotic debridement apparatus 100. In an embodiment, the power source 110 can be at least partially replaceable. For example, the power source 110 can include a battery that is removable from the robotic debridement apparatus 100. In an embodiment, the power source 110 is neither rechargeable nor replaceable.

In an embodiment, the power source 110 can include a power-generating mechanism. For example, the power source 110 can include a piezoelectric power generator configured to generate electrical power by harvesting energy from the movements of the robotic debridement apparatus 100, the locomotive mechanism 104, or the body region. In an embodiment, the power source 110 can include a thermal electric power generator that is configured to generate electrical power from temperature gradients within the robotic debridement apparatus 100 or the body region. In an embodiment, the power source 110 can include one or more photovoltaic cells. In an embodiment, the power source 110 only includes a power-generating mechanism. In an embodiment, the power source 110 includes a power-generating mechanism and at least one other device (e.g., a battery, a capacitor, or a power receiving device).

As previously discussed, the one or more robotic debridement apparatuses disclosed herein include one or more of at least one debriding tool, at least one debris disposal device, or at least one therapeutic device. For example, the robotic debridement apparatuses disclosed herein can include one of, two or more of, or each of the at least one debriding tool, the at least one debris disposal device, or the at least one therapeutic device. Each of the debriding tool, the debris disposal device, and the therapeutic device is configured to facilitate debridement of tissue from the body region. In some embodiments, the robotic debridement apparatuses disclosed herein can also include at least one marking device configured to dispense one or more taggants on the body region of the subject (e.g., identify a marker indicating a specific tissue type, outlining a "map" of an area to be treated or an area already treated, etc.). In some embodiments, the robotic debridement apparatuses disclosed herein can also include at least one extraction device configured to facilitate disposal or removal of the robotic debridement apparatuses from the body region of the subject.

F. Debriding Tools

Figure 3A:
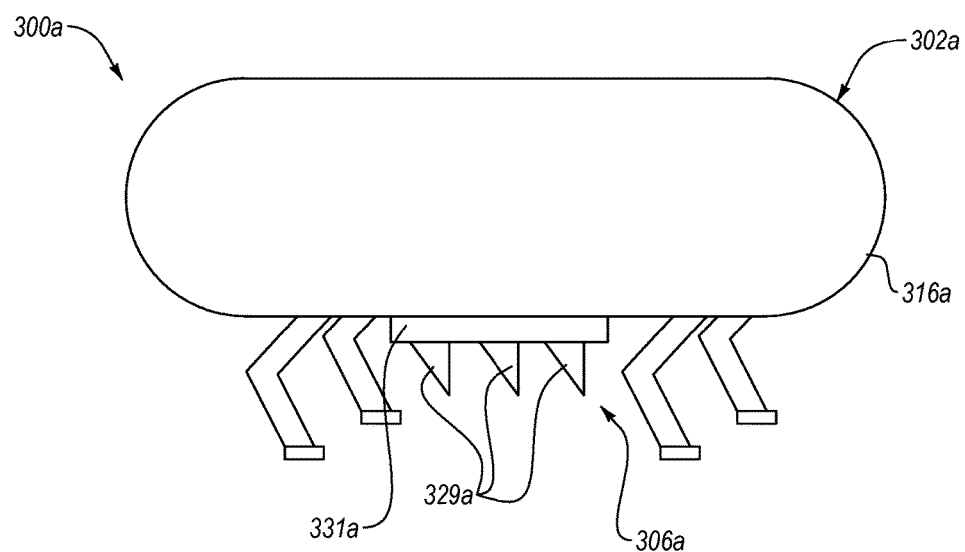
FIGS. 3A-3O are schematic illustrations of robotic debridement apparatuses including different debriding tools, according to different embodiments.
Figure 3B:
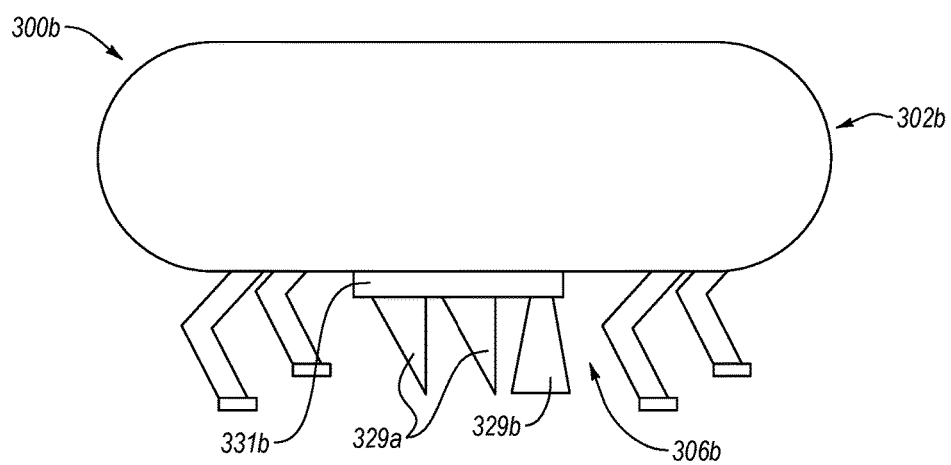
Figure 3C:
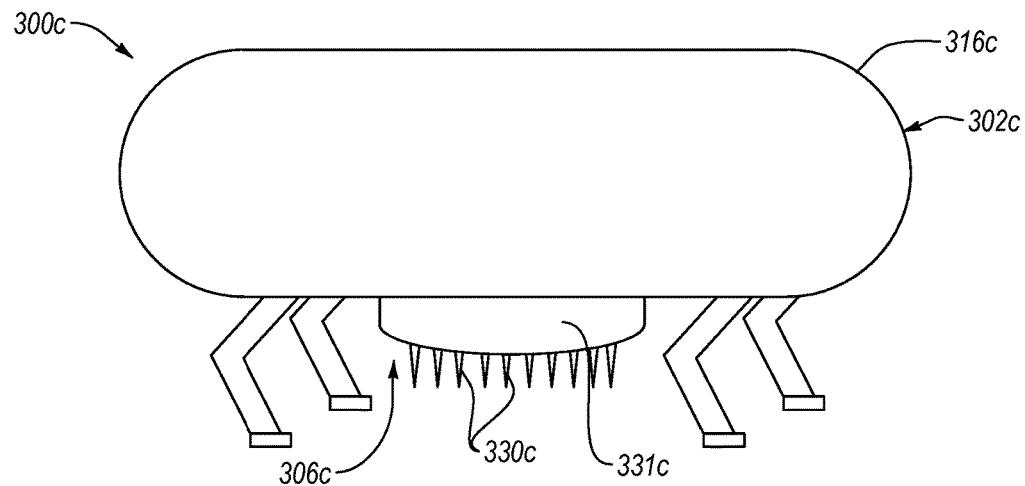
Figure 3D:
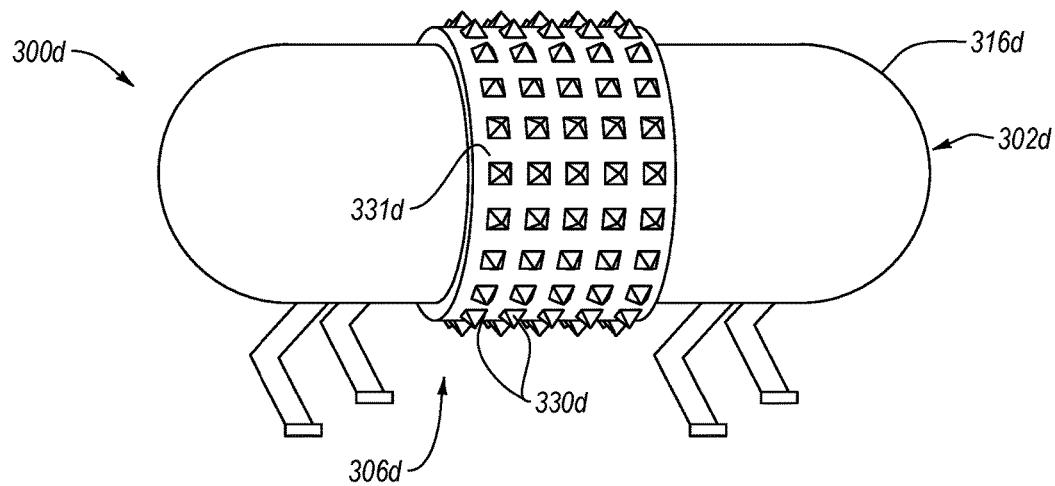
Figure 3E:
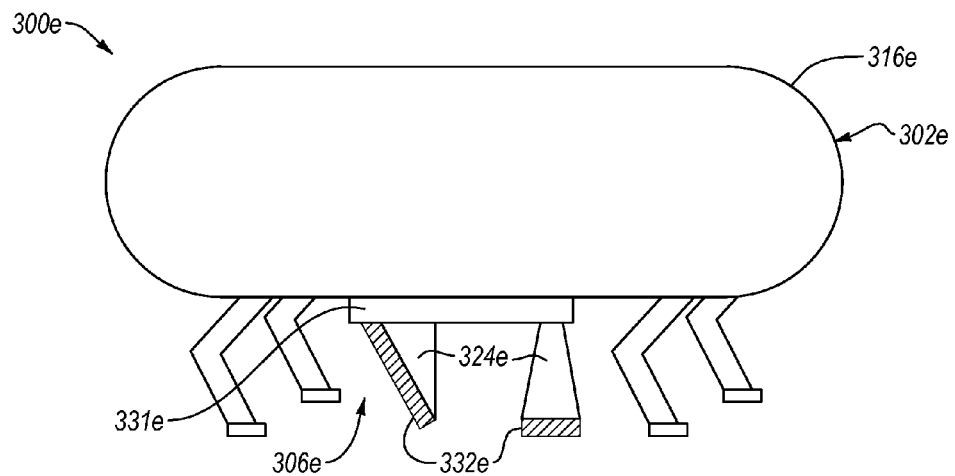
Figure 3F:
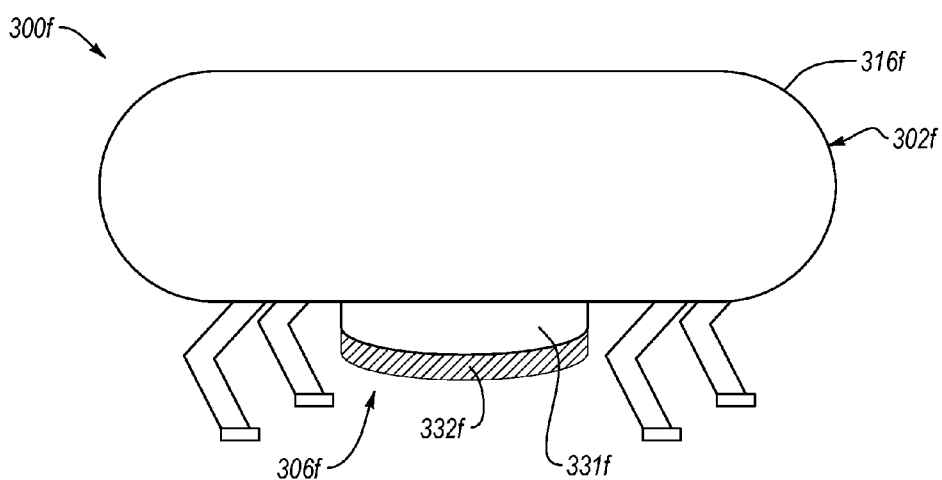
Figure 3G:
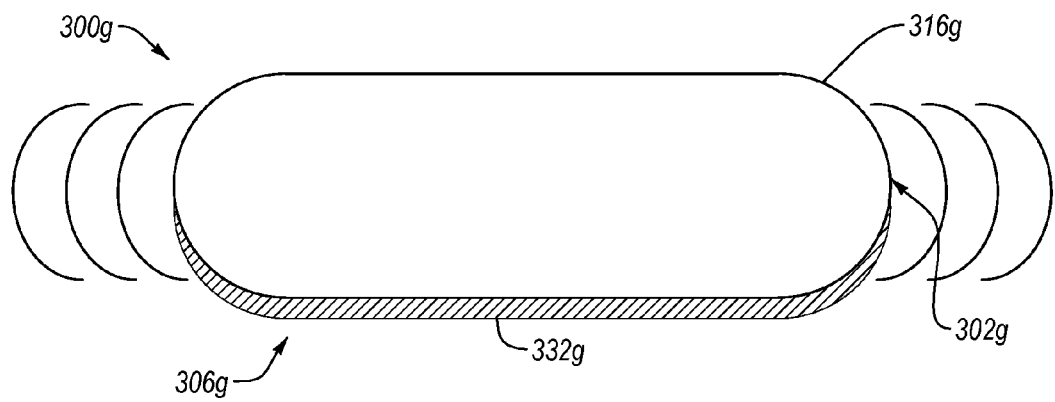
Figure 3H:
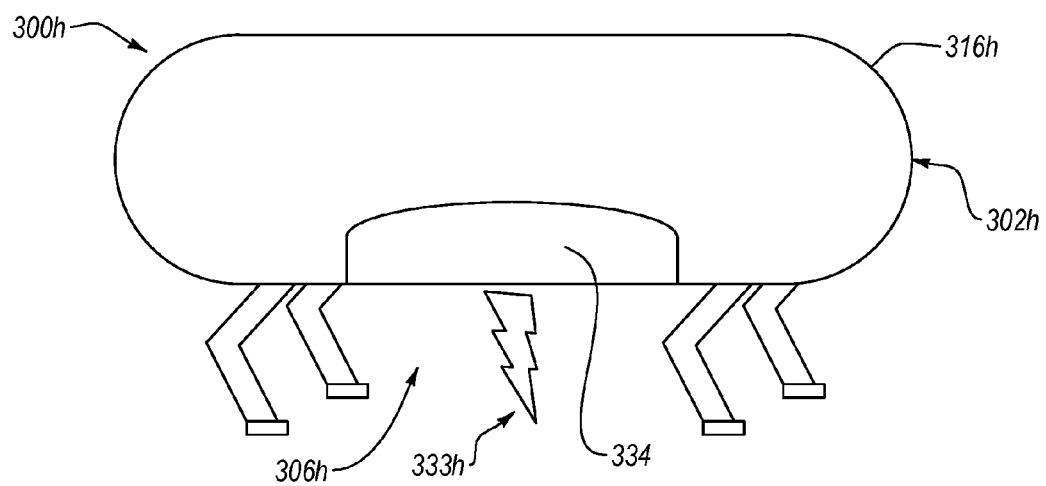
Figure 3I:
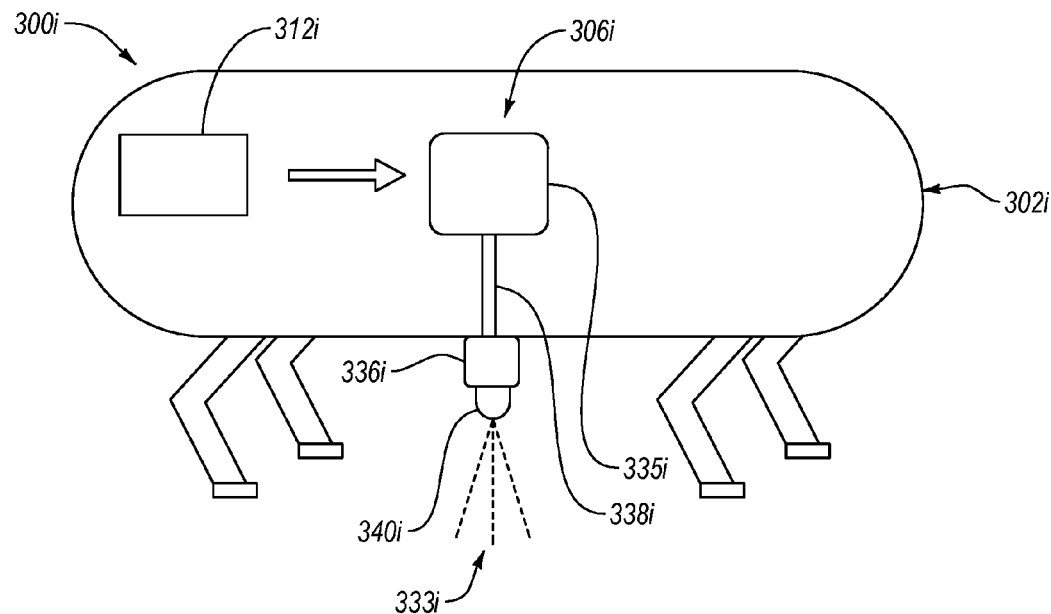
Figure 3J:
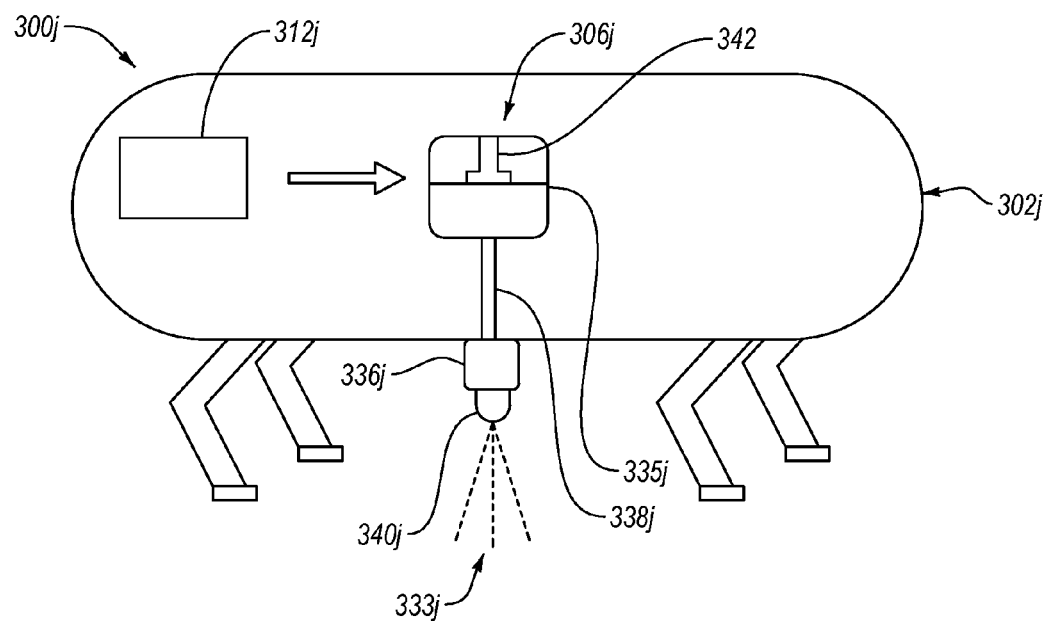
Figure 3K:
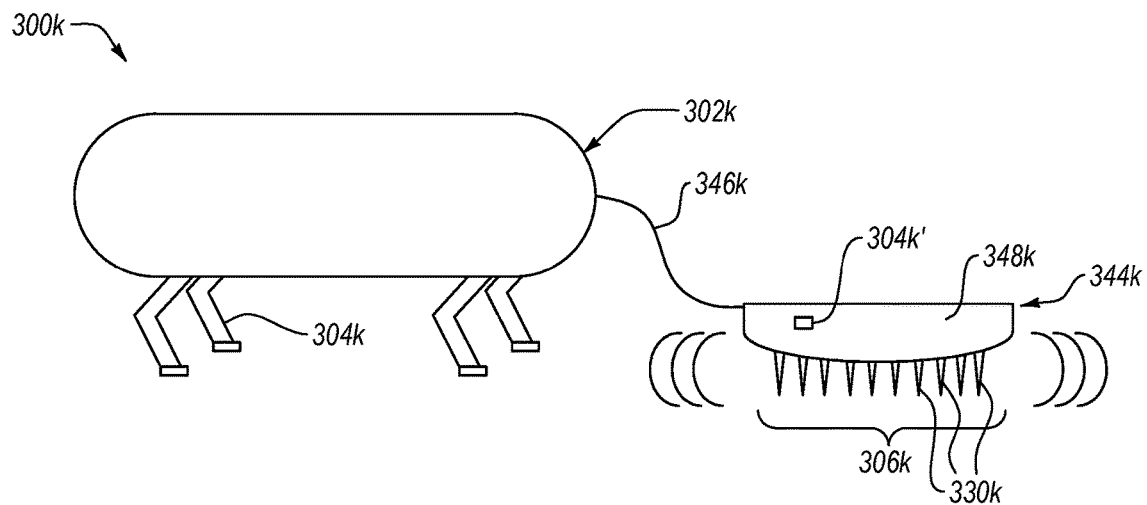
Figure 3L:
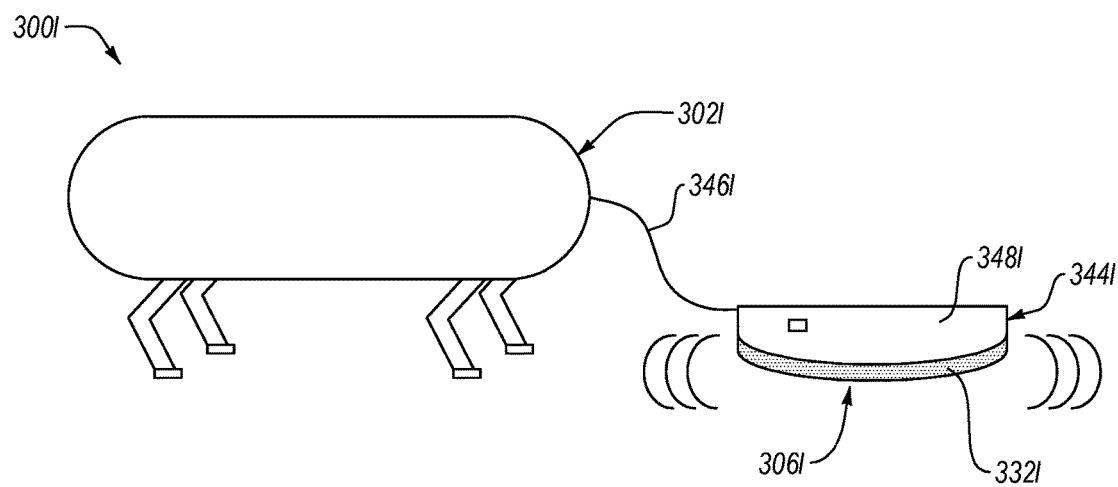
Figure 3M:
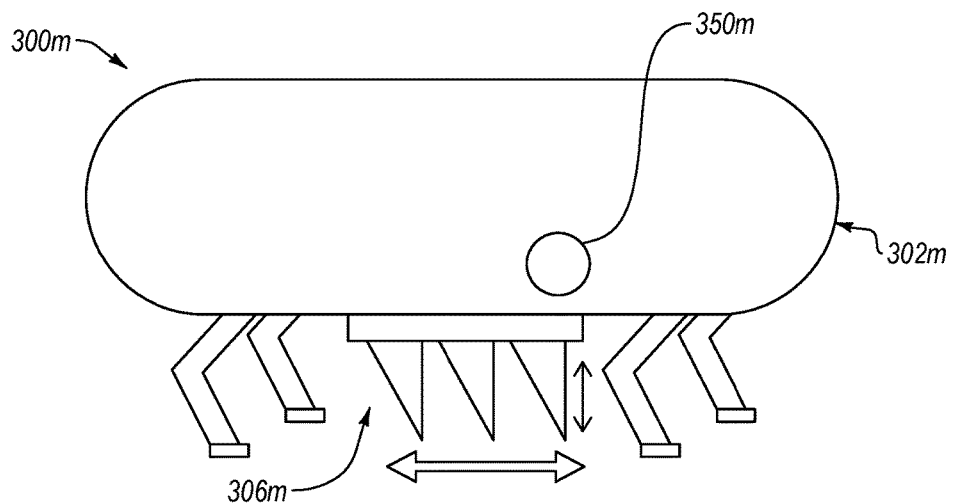
Figure 3N:
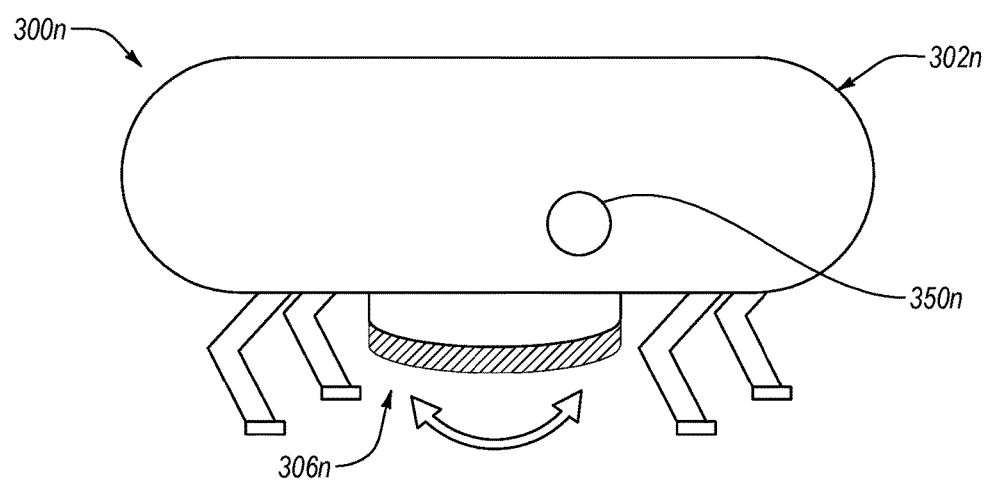
Figure 3O:
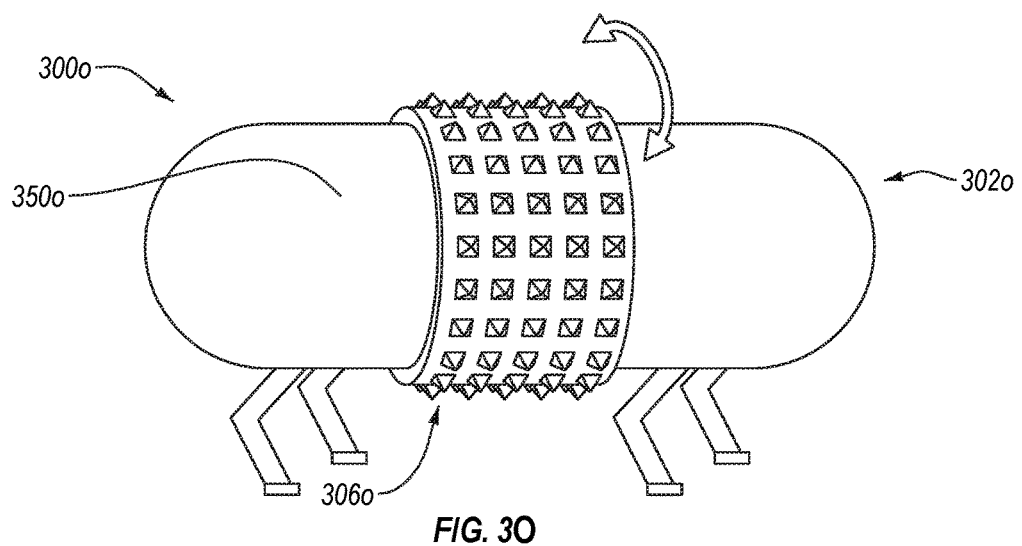

FIGS. 3A-3O are schematic illustrations of robotic debridement apparatuses including different debriding tools, according to different embodiments. The debriding tools disclosed herein are configured to debride tissue (e.g., at least one target tissue) from a body region of the subject. For example the debriding tools are configured to debride at least one of healthy tissue or unhealthy tissue, depending on a particular goal as determined by factors set forth herein. In particular, the debriding tools disclosed herein may be configured to preferentially (e.g., selectively) debride unhealthy tissue from the body region (e.g., minimally debrided and preserve viable tissue).

Except as otherwise described herein, the robotic debridement apparatuses shown in FIGS. 3A-3O and their materials, components, or elements can be similar to or the same as the robotic debridement apparatuses 100, 200*a-g* (FIGS. 1, 2A-2G) and its respective materials, components, or elements. For example, the robotic debridement apparatuses shown in FIGS. 3A-3O can include at least one of a housing, at least one locomotive mechanism, at least one debris disposal device, at least one therapeutic device, one or more sensors, a controller, or a power source. Any of the debriding tools illustrated in FIGS. 3A-3O can be used in any of the robotic debridement apparatuses embodiments disclosed herein.

The debriding tools illustrated herein or any portion thereof may be made of plastic, metal, alloys, ceramic, fiber, carbon, cobalt, silicon, glass, polymer, or any other suitable material. In addition, the debriding tools disclosed herein can have various shapes, sizes, and lengths. Selection of a particular type of configured of the debriding tools illustrated herein can be at least partially based on the type, size, and shape of the target tissue of the body region. The debriding tools disclosed herein and components thereof can be manufactured by standard techniques. For example, the debriding tools disclosed herein and portions thereof can be manufactured using photolithographic etching or micromachining, or can be manufactured in plastic via an injection molding process. The debriding tools disclosed herein and portions thereof can be manufactured by an additive manufacturing process. Examples of additive manufacturing processes include liquid-based processes, e.g., stereolithography, jetted photopolymer, and ink jet printing; powder-based processes, e.g., selective laser sintering, direct metal laser sintering, and three-dimensional printing; and solid-based processes, e.g., laminated object manufacturing, fused deposition modeling. In an embodiment, the debriding tools illustrated herein or any portion thereof may be consumable, replaceable, or disposable.

FIG. 3A illustrates an embodiment of a robotic debridement apparatus 300*a* that includes at least one debriding tool 306*a* associated (e.g., positioned) in or on a housing 302*a* of the robotic debridement apparatus 300*a*. For example, the debriding tool 306*a* can include at least one blade 329*a* extending from the housing 302*a*. In embodiments, the blade 329*a* can be a sharp cutting tool. For example, the blade 329*a* can be sharp, flat, smooth, rough, or serrated. For example, the blade 329*a* can include at least one edge or surface that is configured to cut tissue (e.g., cutting edge), scrape tissue, or abrade tissue (e.g., scraping edge). In an embodiment, the blade 329*a* can exhibit at least one of a negative rake angle, a positive rake angle, or a zero rake angle. The blade 329*a* can debride tissue as the housing 302*a* moves relative to the body region or as the blade 329*a* moves relative to the housing 302*a*. The depth the blade 329*a* debrides tissue from the body region can depend on one or more of a rake angle, a distance the blade 329*a* extends from the outer surface 316*a*, a force applied to the debriding tool 306*a*, etc. In an embodiment, the debriding tool 306*a* includes a plurality of blades 329*a* configured in a pattern (e.g., a random pattern, a linear pattern, an arrayed pattern, etc.). In an embodiment, the blades 329*a* move independently from each other. In an embodiment, the blades 329*a* move in unison.

In an embodiment, the blade 329*a* can include a cutting edge. For example, the blade 329*a* can include a surgical blade. The cutting edge can include a first surface and a second surface extending therefrom. The smallest angle between the first surface and the second surface is less than about 60°, such as less than about 30°, about 30° to about 34°, about 34° to about 44°, or about 44° to about 60°. The angle between the first surface and the second surface can depend on the hardness of a material at the cutting edge, the type of tissue to be debrided, etc.

In an embodiment, the debriding tool 306*a* can include at least one structure 331*a* that is substantially planar, lenticular, or rounded. The structure 331*a* can extend from at least a portion of the housing 302*a*. The blade 329*a* can extend from the structure 331*a*. In an embodiment, the structure 331*a* can be omitted and the blade 329*a* can extend outwardly from or attached to at least a portion of at least one outer surface 316*a* of a housing 302*a*.

FIG. 3B illustrates a robotic debridement apparatus 300*b* that is substantially similar to the robotic debridement apparatus 300*a* (FIG. 3A). For example, the robotic debridement apparatus 300*b* can include at least one debriding tool 306*b* associated (e.g., positioned) in or on a housing 302*a* of the robotic debridement apparatus 300*a*

The debriding tool 306*b* can include at least one blade 329*b*. The blade 329*b* can include one or more scraping tools having a scraping edge or surface. For example, the blade 329*b* can be a flat blade that includes a scraping edge or surface designed to scrape necrotic tissue away from a wound site, while not affecting viable tissue. For example, the scraping edge or surface may be a sharp edge or a serrated edge. For example, the scraping edge or surface can form a curette, such as a scoop, hook, gouge, or similar device. For example, the scraping edge or surface may be a dull edge. For instance, the scraping edge can include a first surface and a second surface extending therefrom. The angle between the first surface and the second surface can be greater than about 60°, such as about 90°. In an embodiment, the scraping edge can include a chamfer or a rounded edge.

In an embodiment, the debriding tool 306*b* can include only the at least one blade 329*b*. In an embodiment, the debriding tool 306*b* can include at least one blade 329*a* (e.g., sharp cutting tool) and at least one blade 329*b* (e.g., scraping tool). In an embodiment, the debriding tool 306*b* can include a structure 331*b* extending from the housing 302*b* and at least one of the blades 329*a*, 329*b* can extend from the structure 331*b*. In an embodiment, at least one of the blades 329*a*, 329*b* can extend from the housing 302*b*.

FIG. 3C illustrates a robotic debridement apparatus 300*c* that includes at least one debriding tool 306*c* associated (e.g., positioned) in or on a housing 302*c* of the robotic debridement apparatus 300*c*. The debriding tool 306*c* can include one or more protrusions 330*c*. In an embodiment, protrusions 330*c* can be of any configuration sufficient to abrade the desired or target tissue. For example, the protrusions 330*c* can include finger-like protrusions, hair-like protrusions, or bristles. For example, each protrusion 330*c* can have at least one scraping edge. For example, each of the protrusions 330*c* can be formed of a material with sufficient stiffness to abrade the target tissue. In an embodiment, the protrusions 330*c* can include microprotrusions.

In an embodiment, the protrusions 330*c* can include a plurality of protrusions 330*c*. For example, at least some of the plurality of protrusions 330*c* can be substantially similar.

In another example, at least some of the plurality of protrusions 330c can be different from each other. For instance, at least one of the plurality of protrusions 330c can be formed from at least one first material and at least one of the plurality of protrusions 330c can be formed from at least one second material that is different than the at least one first material. The different protrusions 330c can be randomly mixed together or arranged in one or more patterns or arrangements (e.g., the plurality of protrusions 330c are arranged in an array).

In an embodiment, the debriding tool 306c can include a structure 331c that is substantially planar, lenticular, or rounded. The structure 331c can include at least some of the protrusions 330c extending therefrom. For example, the structure 331c can include at least one of the protrusions 330c arranged thereon or therein, either randomly or in one or more patterns or arrangements. For example, the protrusions 330c can be attached to, embedded in, or integral to the structure 331c. In an embodiment, the structure 331c can be omitted and the protrusions 330c can extend outwardly from or be attached to at least a portion of at least one outer surface 316c of a housing 302c.

In an embodiment, the debriding tool 306c can debride tissue as the housing 302c moves relative to the body region. In an embodiment, the debriding tool 306c can debride tissue as the debriding tool 306c (e.g., the structure 331c or the protrusions 330c) move relative to the housing 302c. In an embodiment, the protrusions 330c can vibrate, oscillate or otherwise move, individually or as an array, relative to the structure 331c, structure 331c, or housing 302c.

FIG. 3D illustrates a robotic debridement apparatus 300d that includes at least one debriding tool 306d. In an embodiment, the debriding tool 306d can include at least one structure 331d that substantially encloses (e.g., encircles) at least a portion of the housing 302d. In an embodiment, the structure 331d can be rotatably mounted around and rotatable around the housing 302d. The debriding tool 306d can include a plurality of protrusions 330d extending from and attached to at least a portion of the structure 331d. In an embodiment, the structure 331d can be omitted and the protrusions 330d can extend outwardly from or attached to at least a portion of at least one outer surface 316d of a housing 302d such that the protrusions 330d substantially encircles at least a portion of the housing 302d.

FIG. 3E illustrates an embodiment of a robotic debridement apparatus 300e that includes at least one debriding tool 306e. The debriding tool 306e can be similar to the debriding tool 306b (FIG. 3B). For example, the debriding tool 306e can include at least one structure 331e and at least one blade 329e. The debriding tool 306e can also at least one abrasive material 332e that positioned on (e.g., coats) at least a portion of the debriding tool 324e (e.g., at least partially coats the blade or the structure 331e). In an embodiment, the abrasive material 332e can additionally or alternatively be positioned on at least a portion of at least one outer surface 316e of the housing 302e. The abrasive material 332e can debride tissue as the robotic debridement apparatus 300e moves (e.g., vibrates) relative to the body region or as the debriding tool 306e moves relative to the housing 302e, as described herein.

In an embodiment, the abrasive material 332e can include one or more materials having a hardness greater than at least one tissue to be debrided. For example, the abrasive material 332e can include a material that is harder than at least one nonviable tissue but is softer than at least one healthy tissue. As such, the abrasive material 332e preferentially debrides the nonviable tissue versus viable tissue. In an embodiment, the abrasive material 332e can include a material that is harder than at least one nonviable tissue and at least one viable tissue. In an embodiment, the abrasive material 332e can include a material that is softer than at least one nonviable tissue or at least one viable tissue. In an embodiment, the abrasive material 332e can include at least one of silicon carbide, silicon nitride, silicon dioxide, metal, diamond, ceramic, glass, nylon, a mineral compound, a synthetic compound (e.g., polyethylene or polypropylene), a natural or organic compound (e.g., grain, seed, nut, nutshell, mollusk shell, etc.), a crystal (e.g., aluminum oxide, magnesium oxide, sodium chloride, and sodium bicarbonate), and the like. In an embodiment, the abrasive material 332e can include a biocompatible material, such as silicon nitride or titanium. In an embodiment, the abrasive material 332e can include a grit size of about 8 to about 1200, such as about 8 to about 34, about 30 to about 60, about 70 to about 180, or about 320 to about 1200. In an embodiment, the abrasive material 332e can include a microabrasive or a nanoabrasive.

FIG. 3F illustrates an embodiment of a robotic debridement apparatus 300f that includes at least one debriding tool 306f. In an embodiment, the at least one debriding tool 306f can include at least one structure 331f that is similar to the structure 331c (FIG. 3C). The debriding tool 306f can include at least one abrasive material 332f that at least partially coats the structure 331f. In an embodiment, the at least one abrasive material 332f can coat at least a portion of the outer surface 316f of the housing 302f.

FIG. 3G illustrates an embodiment of a robotic debridement apparatus 300g that includes at least one debriding tool 306g. The debriding tool 306g can include at least one abrasive material 332g that is positioned on (e.g., coats) at least a portion of an outer surface 316g of the housing 302g of the robotic debridement apparatus 300g. The abrasive material 332g can debride tissue from a body region when the robotic debridement apparatus 300g moves relative to the body region. For example, the robotic debridement apparatus 300g can be similar to the robotic debridement apparatus 200e (FIG. 2E) and the abrasive material 332g can debrided tissue as the robotic debridement apparatus 300g vibrates.

FIG. 3H illustrates an embodiment of a robotic debridement apparatus 300h that includes at least one debriding tool 306h having at least one energy-emitting device 334. The energy-emitting device 334 can be associated (e.g., positioned) in or on a housing 302h of the robotic debridement apparatus 300h in a manner that allows the energy-emitting device 334 to emit energy 333h (e.g., electromagnetic energy, acoustic energy, electrical energy, thermal energy, etc.) into the body region. For example, a portion of the energy-emitting device 334 that emits energy 333h can at least partially extend from at least one outer surface 316h of the housing 302h. In an embodiment, the energy-emitting device 334 can controllably emit the energy 333h responsive to direction from a controller (e.g., controller 112 of FIG. 1).

In an embodiment, the energy-emitting device 334 can be configured to emit acoustic energy. For example, the energy-emitting device 334 can include an ultrasound device configured to emit ultrasonic energy at a frequency that affects target tissue to be debrided. For example, the ultrasound device can emit low frequency ultrasound that dislodges nonviable tissue. For example, the ultrasound device can emit ultrasonic energy that kills infecting microbes. For example, the ultrasound device can emit ultrasonic energy at a wavelength that stimulates healing. The ultrasonic energy can exhibit a frequency of about 20 kHz to about 10 GHz, such as about 20 kHz to about 60 kHz. The energy-emitting device 334 can directly contact the tissue or be spaced from the tissue (e.g., about 1 µm to about 5 µm) when the energy-emitting device 334 emits the acoustic energy 333.

In an embodiment, the energy-emitting device 334 can be configured to emit electromagnetic energy. For example, the energy-emitting device 334 can include a light-emitting device such as a laser, a light emitting diode, etc. In an embodiment, the energy-emitting device 334 can emit electromagnetic energy at a wavelength that is absorbed by a selected tissue to be debrided. Absorbing the electromagnetic energy can heat the selected tissue, thereby destroying the selected tissue. In an embodiment, the energy-emitting device 334 can emit electromagnetic energy at a wavelength and intensity able to cut the selected tissue from the body region. In an embodiment, the energy-emitting device 334 can emit electromagnetic energy at a wavelength that can ablate tissue.

In an embodiment, the robotic debridement apparatus 300h includes the debriding tool 306h and at least one additional debriding tool (not shown). The at least one debriding tool 360h can include any of the debriding tools disclosed herein. The debriding tool 306h can be configured to act in concert with the at least one additional debriding tool. For example, the debriding tool 306h can include an ultrasound device configured to act in concert with any of the debriding tools disclosed herein, such as a blade, a scraping device, a protrusion, or an abrasive device to debride the tissue. For example, the ultrasound device can be configured to motivate the debriding tool, such as inducing a vibration or acoustic response in the debriding tool. For example, the ultrasound device can be configured to act in concert with device configured to dispense one or more debriding agents (debriding agents 333i of FIG. 3I).

FIG. 3I illustrates an embodiment of a robotic debridement apparatus 300i that includes at least one debriding tool 306i associated (e.g., positioned) in or on a housing 302i of the robotic debridement apparatus 300i. In the illustrated embodiment, the debriding tool 306i includes a device configured to dispense one or more debriding agents 333i into or onto a body region of the subject. For example, the one or more debriding agents 333i can include a fluid (e.g., a liquid or a gas) suitably composed to debride tissue. For example, the one or more debriding agents 333i can include an abrasive (e.g., particles, crystals, or a powder) suitably composed to debride tissue. For example, the one or more debriding agents 333i can include a gel or colloid suitably composed to debride tissue.

The debriding tool 306i can include at least one debriding agent reservoir 335i positioned in or on the housing 302i configured to store the debriding agents 333i therein. The debriding agent reservoir 335i can be fluidly coupled to at least one debriding-dispense element 336i positioned in or on the housing 302i via a conduit 338i. In an embodiment, the debriding-dispense element 336i can be directly coupled to or integrally formed with the debriding agent reservoir 335i. The debriding-dispense element 336i can include a debriding-dispense aperture 340i through which the debriding agents 333i are dispensed at the body region. The at least one debriding-dispense aperture 340i can form part of a sprayer, a slit nozzle, etc. In an embodiment, the debriding tool 306i can be configured to controllably dispense the debriding agents 333i responsive to direction from a controller 312i.

The debriding agents 333i can include any physical, biological, or chemical agent composed to debride at least one target tissue from the body region. In an embodiment, the debriding agent 333i can include one or more fluids, such as a liquid, aerosol, or gas. For example the debriding agent 333i can include a liquid, aerosol, or gas comprising superoxidized water or a peroxide. In an embodiment, the debriding agent 333i can include one or more lytic agents. For example, the lytic agents can include elastase, collagenase, myeloperoxidase, acid hydrolase, lysosomal enzymes, phagocytic cells, combinations thereof, or any suitable lytic agent. In an embodiment, the debriding agents 333i can include one or more enzymatic agents. The enzyme agents can include at least one of bacterial collagenase, papain, urea, fibrinolysin, DNase, trypsin, streptokinase, streptodornase, subtilisin, matrix metalloproteinase, serine proteases, aspartyl proteinase, nuclease, or another enzyme. In an embodiment, the debriding agents 333i can include at least one nonspecific tissue-degrading agent or reactive chemical (e.g., alkaline agent, oxidizing agent, or nucleophilic agent). In an embodiment, the debriding agent 333i can include an abrasive, for example, but not limited to, a composition including particles, crystals, or a powder of any abrasive listed herein. In an embodiment, the debriding agent 333i can include a chemical abrasive such as trichloroacetic acid, glycolic acid, or an abrasive cleanser. In an embodiment, the debriding agent 333i can include a colloid, gel, or emulsion. In an embodiment, the debriding agent 333i can include a hydrocolloid or hydrogel. For example, the debriding agent 333i can include an agent used in wet-to-dry mechanical debridement of necrotic tissue, such as a hydrogel or liquid bandage that dries over time to be removed manually or by a debridement apparatus as described herein, thereby debriding the tissue. In an embodiment, the debriding agents 333i can include a combination of lytic agents, enzyme agents, hydrogel, or another suitable debriding agent. In an embodiment, the debriding agents 333i can include a washing agent or irrigation solution. For example, the debriding agent 333i can include at least one of one or more biocompatible fluids (e.g., saline, water, Ringer's solution, sodium hypochlorite), one or more antiseptics (e.g., superoxidized water, hydrogen peroxide, Povidone iodine), or one or more detergents, or one or more surfactants.

FIG. 3J illustrates an embodiment of a robotic debridement apparatus 300j that includes at least one debriding tool 306j associated (e.g., positioned) in or on a housing 302j of the robotic debridement apparatus 300j. In the illustrated embodiment, the debriding tool 306j is configured to dispense a pressurized fluid 333j into the body region with sufficient force to debride tissue (e.g., necrotic tissue, fibrinous tissue, ischemic tissue, granulation tissue, connective tissue, epithelial tissue, endothelial tissue, or another target tissue). For example, the pressurized fluid 333j can be any liquid, gas, aerosol, powder, colloid, or combination thereof as described herein, including but not limited to a debriding agent 333i (FIG. 3I). In an embodiment, the pressurized fluid 333j includes superoxidized water. In an embodiment, the pressurized fluid 333j includes saline. For example, the pressurized fluid 333j can be a high-pressure jet or other type of high-pressure stream(s) of fluid that has a pressure sufficient to separate at least one target tissue from other tissue. For example, the debriding tool 306j can be configured to controllably dispense fluids under pressure to irrigate the body region or to dislodge a target tissue.

The debriding tool 306j can include a fluid reservoir 335j positioned in or on the housing 302j. The fluid reservoir 335j can be configured to store one or more fluids therein. The fluid reservoir 335j can be fluidly coupled to a fluid-dispense element 336j positioned in or on the housing 302j via a conduit 338j. In an embodiment, the fluid-dispense element 336*j* can be directly coupled to or integrally formed with the fluid reservoir 335*j*. The fluid-dispense element 336*j* can dispense the pressurized fluids 333*j* into or onto the body region using at least one fluid-dispense aperture 340*j* configured to dispense the pressurized fluids 333*j*. The at least one fluid-dispense aperture 340*j* can include a sprayer, a slit nozzle, etc. In an embodiment, the debriding tool 306*j* can be configured to controllably dispense the debriding agents responsive to direction from a controller 312*j*.

The pressurized fluids 333*j* dispensed from the fluid-dispense element 336*j* can be pressurized in any suitable manner. For example, the debriding tool 306*j* can include a pressurizing device 342 (e.g., a pump, compressor, or actuator) positioned in or on the housing 302*j* that is fluidly coupled to at least one of the fluid reservoir 335*j*, the fluid-dispense element 336*j*, or the conduit 338*j*. The pressurizing device 342 can create a pressure gradient that causes the pressurized fluids 333*j* to be dispensed from the fluid-dispense element 336*j* with sufficient force to debride tissue. In an embodiment, the pressurizing device 342 can create a pulsatile pressurized force, with intermittent pressurized delivery of the pressurized fluids 333*j*. In an embodiment, the pressurized fluids 333*j* can be stored in the fluid reservoir 335*e* at a pressure that is greater than the pressure in the body region. The pressurized fluids 333*j* stored in the fluid reservoir 335*e* can include at least one of one or more biocompatible fluids (e.g., saline, water, Ringer's solution), one or more antiseptics (e.g., superoxidized water, hydrogen peroxide), one or more debriding agents (e.g., debriding agents 333*i* of FIG. 3I), or any of the agents disclosed herein.

FIG. 3K illustrates an embodiment of a robotic debridement apparatus 300*k* that includes at least one debriding tool 306*k* that is associated (e.g., coupled) to the robotic debridement apparatus 300*k*. For example, the debriding tool 306*k* includes at least one body 344*k* that is attached to the housing 302*k* by at least one tether 346*k* (e.g., at least one cable). As such, the only portion of the debriding tool 306*k* that is positioned in or on the housing 302*k* is the portion of the tether 346*k* that is attached to the housing 302*k*.

The body 344*k* can be configured to debride tissue when the body 344*k* moves (e.g., travels or vibrates) relative to the body region. For example, the body 344*k* can be configured to be dragged behind the housing 302*f* when a locomotive mechanism 304*k* relocates the housing 302*k*. In an embodiment, the body 344*k* can be configured to move independently of the housing 302*k*. For example, the body 344*k* can include at least one locomotive mechanism 304*k'* positioned therein or thereon that moves the body 344*k*. The locomotive mechanism 304*k'* positioned in or on the body 344*k* can be similar to or the same as any of the locomotive mechanisms disclosed herein (e.g., vibratory mechanism in FIG. 3L). In an embodiment, the at least one locomotive mechanism 304*k'* can be controllably activated, thereby controllably moving the body 344*k* responsive to direction from a controller (e.g., controller 112 of FIG. 1).

The body 344*k* can include at least one debriding tool 306*k* (e.g., any of the debriding tools disclosed herein). For example, in the illustrated embodiment, the body 344*k* includes a plurality of protrusions 330*k* (e.g., array of protrusions) positioned on an outer surface 348*k* of the body 344*k*.

FIG. 3L illustrates an embodiment of a robotic debridement apparatus 300*l* that is similar to the robotic debridement apparatus 300*k* (FIG. 3K). For example, the robotic debridement apparatus 300*l* can include at least one body 344*l* that is coupled to a housing 302*l* using a tether 346*l*. The body 344*l* can include at least one debriding tool 306*l*. The debriding tool 306*l* can include at least one abrasive material 332*l* coating at least a portion of an outer surface 348*l* of the body 344*l*.

In an embodiment, the body 344*l* can include any of the debriding tools disclosed herein. In an embodiment, the housing 302*l* can also include at least a second debriding tool positioned in or on the housing 302*l* (not shown).

FIG. 3M illustrates a robotic debridement apparatus 300*m* that includes a debriding tool 306*m* (e.g., any of the debriding tools disclosed herein). For example, the debriding tool 306*m* can be similar to the debriding tool 306*a* (FIG. 3A). In an embodiment, at least a portion of the debriding tool 306*m* can be movable relative to the housing 302*m*. For example, the debriding tool 306*m* can be configured to at least one of be displaced relative to the housing 302*m* (e.g., one or more of forward/backward, left/right, or up/down), rotate (e.g., spin relative to or rotate around a portion of the housing 302*m*), oscillate, tilt, vibrate, or move linearly relative to an axis (e.g., along the longitudinal axis of the housing 302*m*). As such, the debriding tool 306*m* can at least one of shave, scrape, abrade, shred, or otherwise physically debride tissue from the body region.

In an embodiment, the robotic debridement apparatus 300*m* can include one or more actuators 350*m* positioned in or on the housing 302*m*. The actuators 350*m* can be operably coupled to at least a portion of the movable debriding tool 306*m* such that activating the actuators 350*m* moves at least a portion of the debriding tool 306*m* relative to the housing 302*m*. The actuators 350*m* can include any of the actuators disclosed herein or any other suitable actuator. For example, the actuators 350*m* can include a vibratory mechanism (e.g., piezoelectric material) or a motor. For example, the actuators 350*m* can include an actuator including at least one three-dimensional printed micropillar structure, such as a vibrating motor or a brush motor. In an embodiment, the actuators 350*m* can be controllably actuated responsive to direction from a controller (e.g., controller 112 of FIG. 1).

FIG. 3N illustrates a robotic debridement apparatus 300*n* that includes at least one debriding tool 306*n* (e.g., any of the debriding tools disclosed herein). For example, the debriding tool 306*n* can be similar to the debriding tool 306*f* (FIG. 3F). In an embodiment, at least a portion of the debriding tool 306*n* can be movable relative to the housing 302*n*. For example, at least a portion of the debriding tool 306*n* can be configured to be displaced relative to the housing 302*n* in any of the manners disclosed herein, such as rotation as illustrated. In an embodiment, at least a portion of the debriding tool 306*n* can be coupled to one or more actuators 350*n* configured to move at least a portion of the debriding tool 306*n* relative to the housing 302*n*.

FIG. 3O illustrates a robotic debridement apparatus 300*o* that includes at least one debriding tool 306*o* (e.g., any of the debriding tools disclosed herein). For example, the debriding tool 306*o* can be similar to the debriding tool 306*d* (FIG. 3D). In an embodiment, at least a portion of the debriding tool 306*o* can be movable relative to the housing 302*o*. For example, at least a portion of the debriding tool 306*o* can be configured to be displaced relative to the housing 302*o* in any of the manners disclosed herein. In an embodiment, at least a portion of the debriding tool 306*o* can be coupled to one or more actuators 350*o* configured to move at least a portion of the debriding tool 306*o* relative to the housing 302*o*.

G. Debris Disposal Devices

FIGS. 4A-4J are schematic illustrations of robotic debridement apparatuses including different debriding tools, according to different embodiments. Except as otherwise described herein, the robotic debridement apparatuses shown in FIGS. 3A-3E and their materials, components, or elements can be similar to or the same as the robotic debridement apparatuses 100, 200a-g, 300a-o (FIGS. 1-3O) and their respective materials, components, or elements. For example, the robotic debridement apparatuses shown in FIGS. 4A-4J can include at least one of a housing, at least one locomotive mechanism, at least one debriding tool, at least one therapeutic device, one or more sensors, a controller, or a power source. Any of the debris disposal devices illustrated in FIGS. 4A-4J can be used in any of the robotic debridement apparatuses embodiments disclosed herein.

The debris disposal devices disclosed herein are configured to capture (e.g., acquire, sequester, secure, dispose of, remove, absorb, adsorb, or adhere thereto) at least one substance from the wound. The at least one substance can include debrided tissue (e.g., at least one target tissue). The debrided tissue can include tissue that is debrided using at least one robotic debridement apparatus including at least one debriding tool, a debriding tool used by a user (e.g., a physician, a nurse, other healthcare provider, the subject, a computer, or a third party, etc.), at least one debriding agent, maggots, or any other debriding tool. The debrided tissue can include nonviable tissue or viable tissue, depending on the goal and as determined by one or more factors described herein. In an embodiment, the robotic debridement apparatus selectively debrides nonviable tissue, by the debriding tools disclosed herein, and preserves as much healthy, viable tissue as possible. The substances can also include at least one foreign material or foreign matter. The foreign material or foreign matter can include debris present in the wound, one or more agents dispensed from at least one robotic debridement apparatus, one or more agents dispensed from a dressing, a fluid used to clean or irrigate the body region, a portion of at least one robotic debridement apparatus that has worn away, or another material introduced into the body region during the debridement process. The substance can also include one or more fluids. The fluid can include serous fluid, fibrinous fluid, serosanguineous fluid, sanguinous fluid, seropurulent fluid, purulent fluid, haemopurulent fluid, haemorrhagic fluid, blood, exudate, certain tissue, degraded tissue, or another fluid present within the body region. The substance can include at least one infectious material (e.g., bacteria, bacterial matter, fungus, fungal matter, yeast, yeast matter, virus, viral matter, infected cell or matter therefrom, etc.).

Figure 4A:
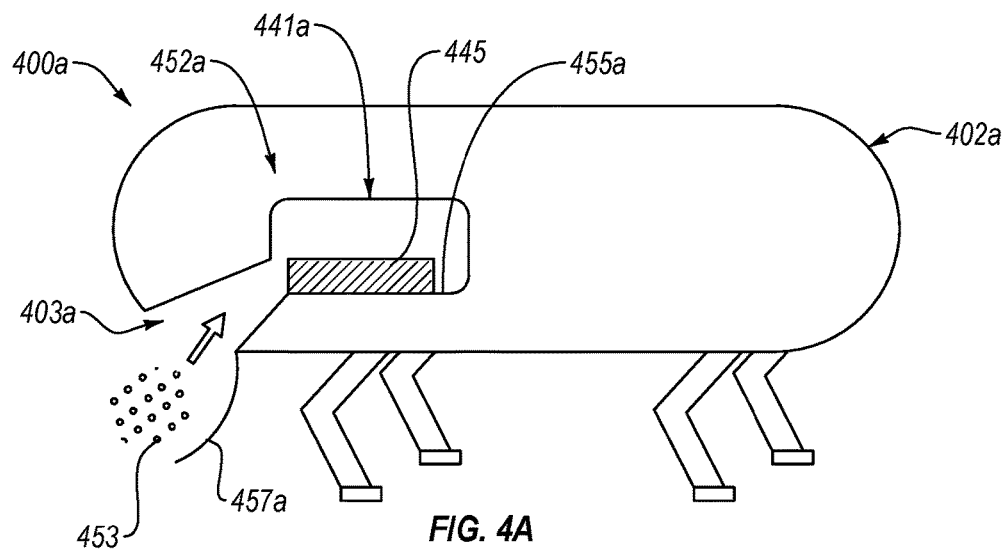
FIGS. 4A-4J are schematic illustrations of robotic debridement apparatuses including different debris disposal devices, according to different embodiments.

FIG. 4A illustrates an embodiment of a robotic debridement apparatus 400a that includes at least one debris disposal device 452a configured to remove at least one substance 453 from the body region. For example, the debris reservoir 441a can be configured to capture a fluid or solid that has rebounded from the body region (e.g., a splash or an aerosol).

In an embodiment, the debris disposal device 452a includes a debris reservoir 441a positioned in or on the housing 402a. The debris reservoir 441a can be configured to directly access the body region through an opening 403a defined by the housing 402a. The debris reservoir 441a can include an internal surface 455a. The debris reservoir 441a can include at least one capture material 445 that is positioned on (e.g., coats) at least a portion of the internal surface 455a. The capture material 445 can be configured to have the substance 453 attached thereto when the substance 453 enters the debris reservoir 441a, thereby preventing the substance 453 from exiting the debris reservoir 441a. For example, the capture material 445 can include an adhesive, an adsorbent, or an absorbent. Examples of adhesives, adsorbents, and absorbents are disclosed elsewhere herein.

In an embodiment, the debris disposal device 452a and its debris reservoir 441a are configured to capture the substance 453 as the robotic debridement apparatus 400a travels across a surface. For example, debris disposal device 452a can include a substance motivator 457a (e.g., scoop) at or near the opening 403 that is configured to gather (e.g., scoop up) the substance 453 into the debris reservoir 441a. In an embodiment, the substance motivator 457a can be coupled to an actuator (not shown) that is configured to move the substance motivator 457a relative to the housing 402a. For example, the actuator can be configured to move the substance motivator 457a between a closed and open position.

Figure 4B:
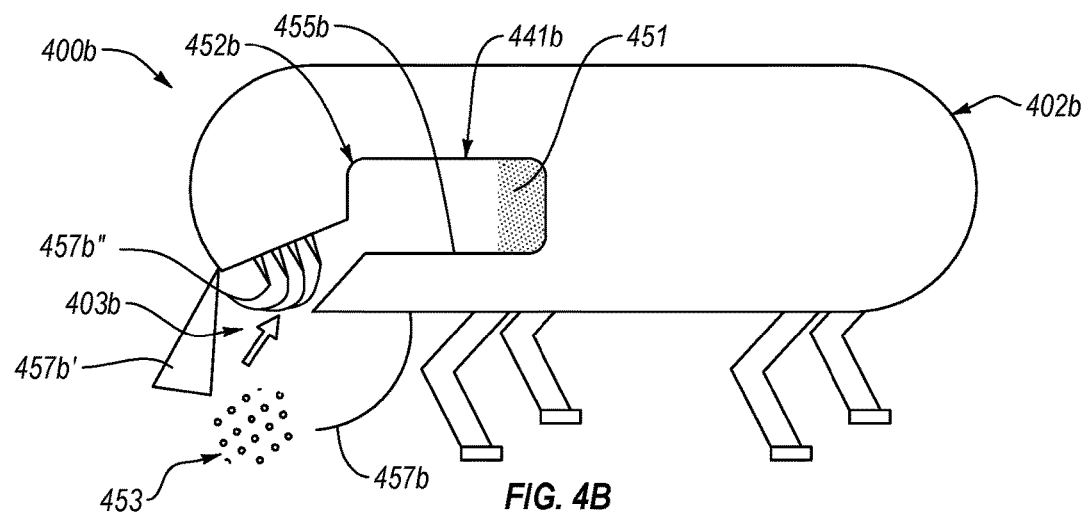

FIG. 4B illustrates an embodiment of a robotic debridement apparatus 400b that includes at least one debris disposal device 452b configured to remove at least one substance 453 from the body region. In an embodiment, the debris disposal device 452b can include a debris reservoir 441b positioned in or on the housing 402b. The debris reservoir 441b can be at least partially defined by an internal surface 455b and include an opening 403b at least partially defined by the housing 402b.

In an embodiment, the debris reservoir 441b can include at least one degrading agent 451 therein. The degrading agent 451 can be formulated to degrade or destroy at least one substance 453 captured from the body region. For example, the degrading agent 451 can include at least one of a liquid, gas, solid, powder, gel, colloid, other compound, or combinations thereof. For example, the degrading agent 451 can include a hydrogel coating at least a portion of the internal surface 455b of the debris reservoir 441b. For example, the degrading agent 451 can include a liquid (not shown) stored in the debris reservoir 441b. In an embodiment, the degrading agent 451 includes a lytic, an autolytic, a proteolytic, an enzymatic agent, or any of the debriding agents described herein. In an embodiment, the degrading agent 451 includes a nonspecific degrading agent, such as an acid, an alkaline, or an oxidase. In an embodiment, the degrading agent 451 includes an antimicrobial. In an embodiment, the debris reservoir 441b or degrading agent 451 includes a mechanistic aspect configured to aid in degrading the substance 453. For example, the debris reservoir 441b can include a vibrating mechanism, a grinding mechanism, or the like.

In an embodiment, the debris disposal device 452b includes at least one substance motivator for moving the substance into the debris reservoir. For example, the substance motivator can include at least one of a first substance motivator 457b, a second substance motivator 457b', or a third substance motivator 457b". In an embodiment, the first substance motivator 457b can be substantially similar to the substance motivator 457a (FIG. 4A). In an embodiment, the second substance motivator 457b' can include a device (e.g., a shaped blade or a brush) that steers or pushes the substance 453 into the opening 403b. The second substance motivator 457b' can be positioned at or near the opening 403b. In an embodiment, the third substance motivator 457b" can include a device (e.g., bristles) that steers or moves the substance 453 through the opening 403 and into the debris reservoir 441b. For example, the third substance motivator 457b" can be positioned at, near, or in the opening 403b. In an embodiment, at least one of the first, second, or third substance motivators 457b, 457b', 457b" can include at least one three-dimensional printed micropillar structure.

In an embodiment, the debris disposal device 452b can include one or more actuators (not shown) that are operably coupled to at least one of the first, second, or third substance motivators 457b, 457b', 457b". The actuators can be configured to move at least one of the first, second, or third substance motivators 457b, 457b', 457b" to facilitate steering the substance 453 to and through the opening 403. For example, at least one of the first, second, or third substance motivators 457b, 457b', 457b" can be moved under control of the controller (e.g., controller 112 of FIG. 1). In an embodiment, at least one of the first, second, or third substance motivators 457b, 457b', 457b" is not operably coupled to the actuators and instead passively steers the substance 453 to or through the opening 403b (e.g., at least one the first, second, or third substance motivators 457b, 457b', 457b" is substantially in communication with the locomotive mechanism and moves with the self-propelling force).

Figure 4C:
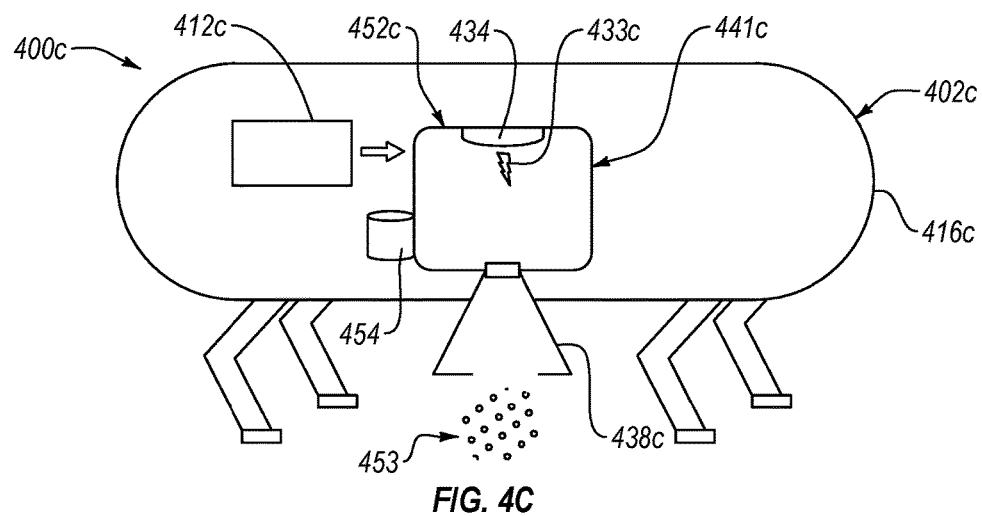

FIG. 4C illustrates an embodiment of a robotic debridement apparatus 400c that includes at least one debris disposal device 452c configured to remove at least one substance 453 from the body region. In an embodiment, the debris disposal device 452c includes a suction device 454 positioned in or on a housing 402c of the robotic debridement apparatus 400c. The suction device 454 can be configured to remove or capture the substance 453 from the body region. For example, the suction device 454 can include a pump, a compressor, a device having a lower pressure than the body region (e.g., the debris reservoir 441c can initially exhibit a lower pressure than the body region). In an embodiment, the suction device 454 can controllably remove the substance 453 from the body region responsive to direction from a controller 412c.

In an embodiment, the suction device 454 can be coupled (e.g., fluidly coupled) to a debris reservoir 441c positioned in or on the housing 402c. The suction device 454 or the reservoir 441c can be coupled (e.g., fluidly coupled) to the body region via at least one conduit 438c positioned in or on the housing 402c. For example, the conduit 438c can extend from the reservoir 441c to at least one outer surface 416c of the housing 402c or can further extend outwardly from the outer surface 416c of the housing 402c into the body region. The debris reservoir 441c can be configured to store the substance 453 from the body region that is captured therefrom by the suction device 454.

In an embodiment the debris reservoir 441c includes an energy-emitting device 434 configured to deliver energy 433c to the substances 453 held in the debris reservoir 441c. The energy 433c can be configured to degrade or destroy a tissue, cell, or microbe that is a component of the substance 453. For example, the energy-emitting device 434 can be configured to emit at least one of acoustic energy, thermal energy, electrical energy, or electromagnetic energy. For instance, the energy-emitting device 434 can be configured to emit an ultraviolet light, infrared light, or other light. For instance, the energy-emitting device 434 can be configured to emit ultrasound energy or microwave energy.

Figure 4D:
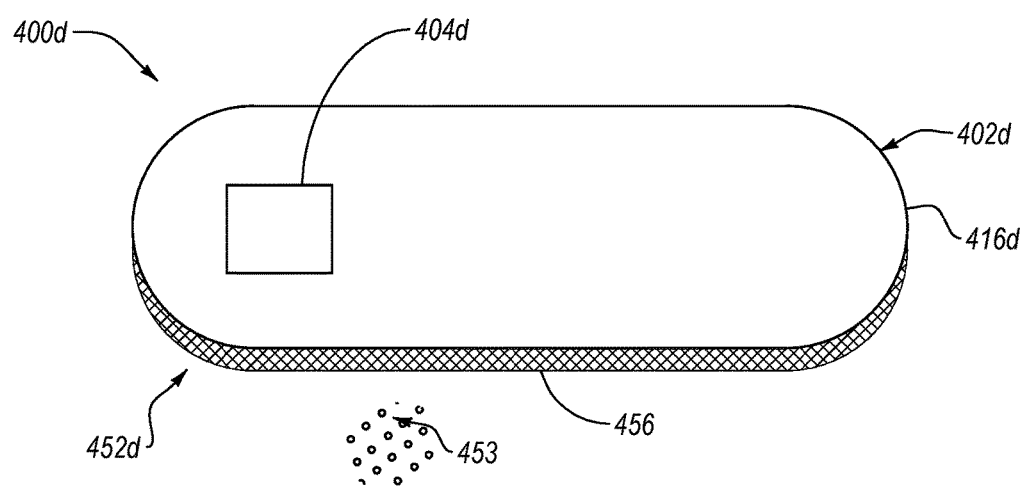

FIG. 4D illustrates an embodiment of a robotic debridement apparatus 400d that includes at least one debris disposal device 452d having at least one adhesive material 456 configured and composed such that at least one substance 453 from the body region attaches thereto. For example, the robotic debridement apparatus 400d includes a housing 402d having at least one outer surface 416d. In an embodiment, the adhesive material 456 can be positioned in or on a housing 402d of the robotic debridement apparatus 400d such that the adhesive material 456 is exposed to the body region. For example, the adhesive material 456 can be positioned on (e.g., coat) at least a portion of the outer surface 416d.

In an embodiment, the adhesive material 456 can include any suitable adhesive. For example, the adhesive material 456 can include at least one of a drying adhesive, a pressure-sensitive adhesive, a contact adhesive, a hot melt adhesive (e.g., the robotic debridement apparatus 400d includes a heating element that heats the adhesive material 456), a reactive hot melt adhesive, a multi-part adhesive, a one-part adhesive, a natural adhesive, a synthetic adhesive, or another suitable adhesive. In an embodiment, the adhesive material 456 can include at least one of a glue, a cement, a mucilage, a liquid, a film, pellets, a gel, or a paste. In an embodiment, the adhesive material 456 can include at least one of silicon, an amine, or an acrylate polymer.

In an embodiment, the adhesive material 456 can include an adhesive that is directly applied to the robotic debridement apparatus 400d (e.g., directly applied to the outer surface 416d). In an embodiment, the adhesive material 456 can include an adhesive that is applied to a substrate (e.g., a flexible, semi-rigid, or rigid substrate) and the substrate is attached to a portion of the robotic debridement apparatus 400d.

In an embodiment, the adhesive material 456 is configured to not substantially restrict movement of the robotic debridement apparatus 400d within the body region. For example, the adhesive material 456 can include an adhesive that does not attach to or does not substantially attach to tissue in the body region. In an embodiment, the adhesive material 456 can include an adhesive that forms a weak attachment to the body region that is easily broken by the locomotive force generated by at least one locomotive mechanism 404d of the robotic debridement apparatus 400d. In an embodiment, the adhesive material 456 is positioned on a portion of the robotic debridement apparatus 400d that does not normally contact a fixed surface of the body region. For example, the adhesive may be positioned in or on the housing 402d in such a manner as to capture the substance 453 as the substance 453 is dislodged from the body region (e.g., by a blade or fluid spray).

Figure 4E:
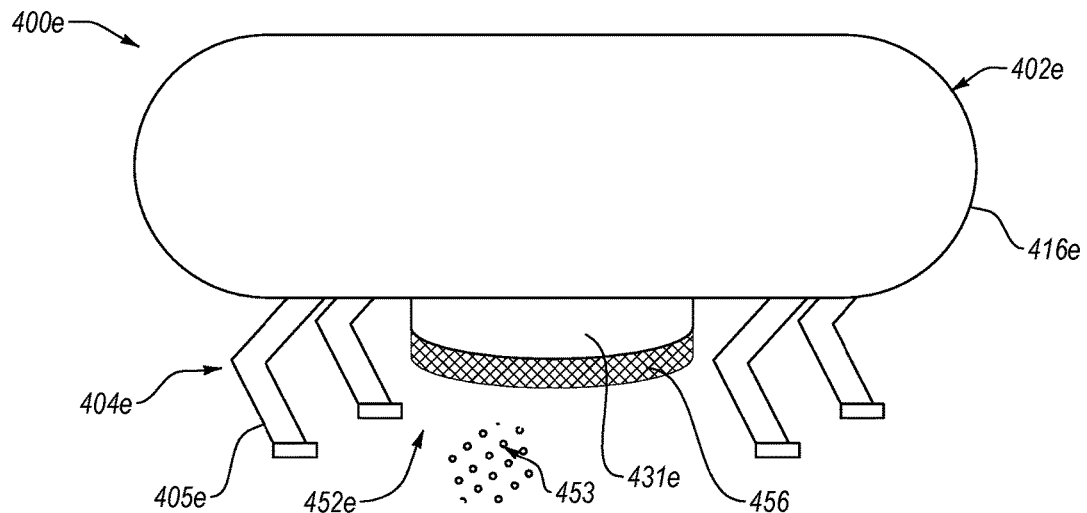

FIG. 4E illustrates an embodiment of a robotic debridement apparatus 400e that includes at least one debris disposal device 452e having at least one adhesive material 456 configured and composed such that at least one substance 453 from the body region attaches thereto. The robotic debridement apparatus 400e can include at least one structure 431e extending from the housing 402e or an outer surface 416e of the housing 402e. In an embodiment, the structure 431e can be a three-dimensional structure having a substantially planar surface, lenticular surface, or rounded surface at least partially coated with the adhesive material 456. The adhesive material 456 can be positioned on (e.g., coat) at least a portion of the structure 431e. In an embodiment, the adhesive material 456 can be positioned on (e.g., coat) at least a portion of the locomotive mechanism 404e (e.g., at least one of the impelling mechanism 405e).

Figure 4F:
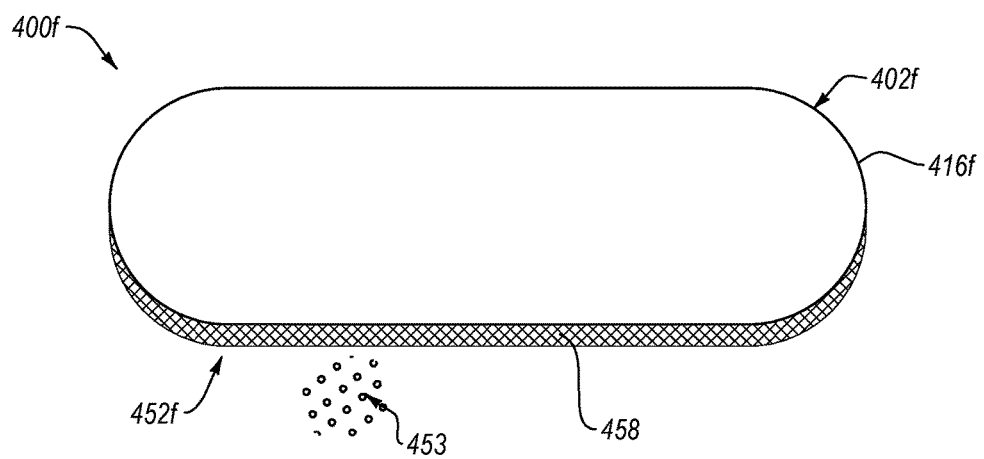

FIG. 4F illustrates an embodiment of a robotic debridement apparatus 400f that includes at least one debris disposal device 452f having at least one absorbent material 458 configured and composed to capture and/or sequester at least one substance 453 from the body region. The absorbent material 458 is positioned in or on a housing 402f of the robotic debridement apparatus 400f such that the absorbent materials 458 is exposed to the at least one substance 453f of the body region. For example, the absorbent material 458 can be at least partially positioned on (e.g., coat) at least one outer surface 416f of the housing 402f, or within the housing 402f (e.g., within debris reservoir 441a-c of FIGS. 4A-4C). In an embodiment, the absorbent material 458 is positioned in a portion of the robotic debridement apparatus 400f that does not normally contact a fixed surface of the body region. For example, the absorbent may be positioned in the housing 402f in such a manner as to capture the substance 453 as it is dislodged from the body region (e.g., by a blade or fluid spray).

In an embodiment, the absorbent material 458 can include a wicking material, such as a porous material, a woven fabric, etc. In an embodiment, the absorbent material 458 can include a material configured to attach (e.g., bond), absorb, or adsorb at least one substance 453 thereto. For example, the absorbent material 458 can include a material that is an adsorbent. For example, the absorbent material 458 can include at least one of one or more gel compounds, one or more oxygen-containing compounds (e.g., silica gel, zeolite), one or more carbon-based compounds (e.g., activated carbon, graphite), one or more porous polymer-based compounds, activated alumina, calcium sulfate, calcium oxide, clay, or another suitable material. In an embodiment, the absorbent material 458 can include a hygroscopic material (e.g., quartz).

In an embodiment, the debris disposal device 452f can include a suction device (e.g., the suction device 454 of FIG. 4C) coupled to the absorbent material 458. For example, the suction device can pull or draw the substance 453 into or through the absorbent material 458. As such, the suction device can increase a rate at which the absorbent material 458 absorbs or adsorbs the substance 453 and can increase the amount of the substance 453 absorbed or adsorbed by the absorbent material 458. In an embodiment, the suction device can controllably pull the at least one substance 453 into or through the absorbent material 358 responsive to direction from a controller (e.g., controller 112 of FIG. 1).

Figure 4G:
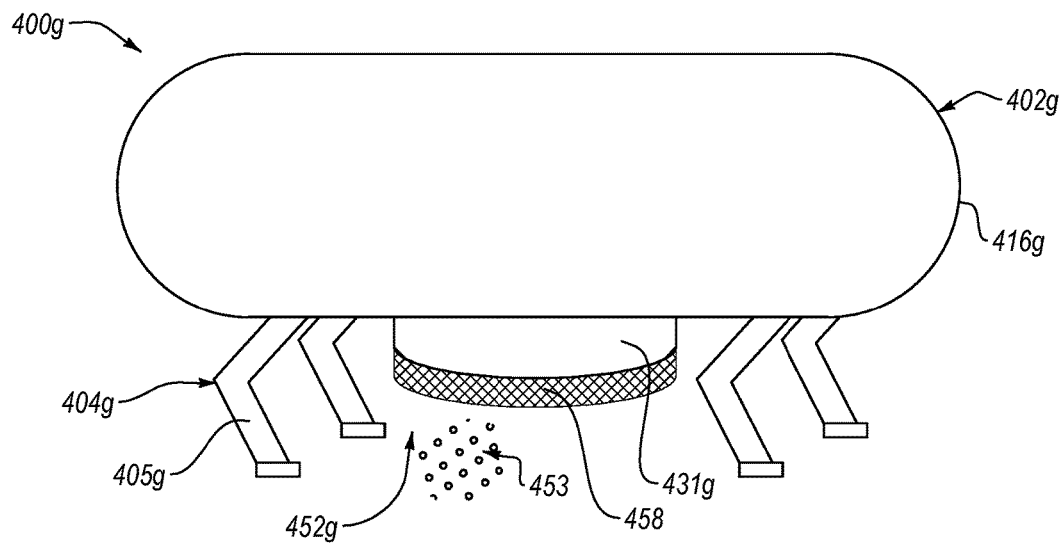

FIG. 4G illustrates an embodiment of a robotic debridement apparatus 400g that includes at least one debris disposal device 452g having at least one absorbent material 458 configured and composed such that at least one substance 453 from the body region attaches thereto. The robotic debridement apparatus 400g can include at least one structure 431g extending from the housing 402g or an outer surface 416g of the housing 402g. In an embodiment, the structure 431g can be a three-dimensional structure having a substantially planar surface, lenticular surface, or rounded surface at least partially coated with the absorbent material 458. The absorbent material 458 can be positioned on (e.g., coat) at least a portion of the structure 431g. In an embodiment, the absorbent material 458 can be positioned on (e.g., coat) at least a portion of the locomotive mechanism 404g (e.g., at least a portion of an impelling mechanism 405g).

Figure 4H:
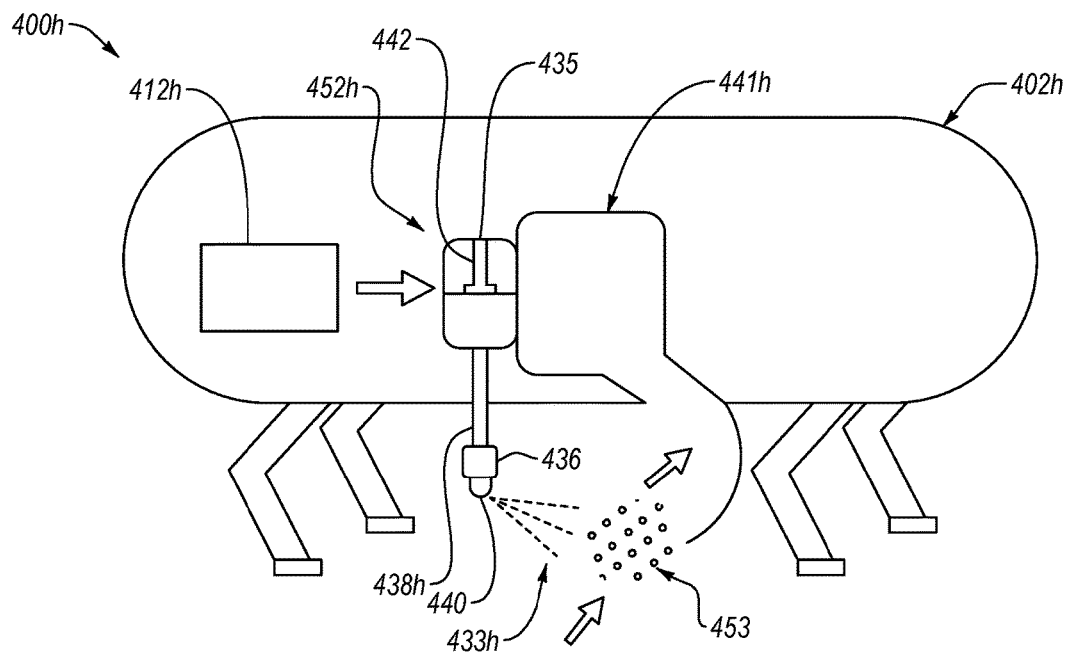

FIG. 4H illustrates an embodiment of a robotic debridement apparatus 400h that includes at least one debris disposal device 452h positioned in or on a housing 402h of the robotic debridement apparatus 400h. In the illustrated embodiment, the debris disposal device 452h can be configured to dispense a pressurized fluid 433h into or onto the body region at a pressure sufficient to move at least one substance 453 from a first location to a second location. For example, in the illustrated embodiment, the fluid-dispense element 436 is configured to dispense pressurized fluids 433h to move or direct the substance 453 into the debris reservoir 441h. For example, the fluid-dispense element 436 can be configured to dispense pressurized fluids 433h to move the substance 453 toward a substance motivator (e.g., first, second, or third substance motivators 457b. 457b', 457b" of FIG. 4B). For example, the pressurized fluid 433h can include air, water, saline, antiseptic, irrigation fluid, or other suitable fluid.

In an embodiment, the debris disposal device 452h can include at least one fluid reservoir 435 positioned in or on the housing 402h configured to store one or more fluids therein (e.g., the pressurize fluids 433h or the fluids that become the pressurized fluids 433h). The one or more fluids can include any of the fluids disclosed herein. The fluid reservoir 435 can be fluidly coupled to at least one fluid-dispense element 436 positioned in or on the housing 402h. In an embodiment, the fluid-dispense element 436 can be coupled to the fluid reservoir 435 via a conduit 438h, directly coupled to the fluid reservoir 435, or integrally formed with the fluid reservoir 435. The fluid-dispense element 436 can include a fluid-dispense aperture 440 configured to dispense the pressurized fluids 433h. The at least one dispense aperture 440 can form part of a sprayer, a slit nozzle, etc. The debris disposal device 452d can further include a pressurizing device 442 that is fluidly coupled to fluid reservoir 435 and the fluid-dispense element 436. The pressurizing device 442 can be substantially similar to the pressurizing device 342 (FIG. 3J). For example, the pressurizing device 442 can include a pump. In an embodiment, the fluid-dispense element 436 or the pressurizing device 442 can dispense the pressurized fluids 433h therefrom responsive to direction from a controller 412h.

Figure 4I:
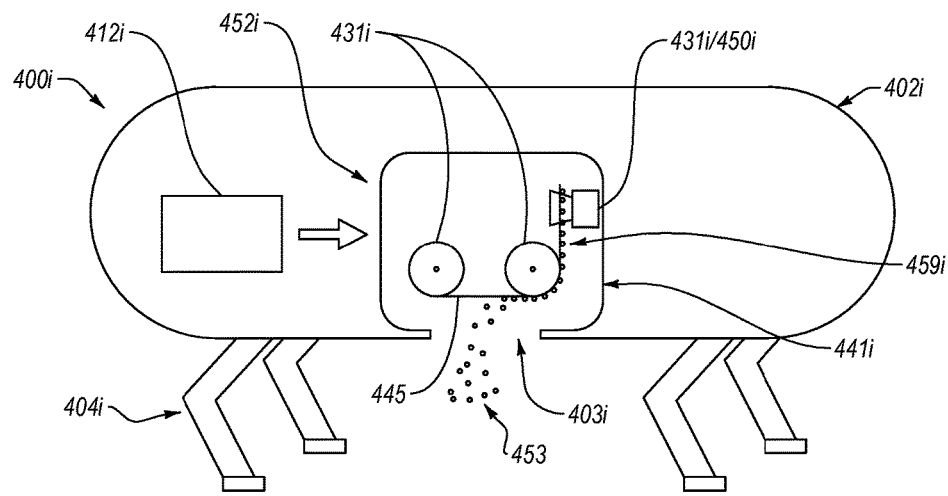

FIG. 4I illustrates an embodiment of a robotic debridement apparatus 400i that includes at least one debris disposal device 452i. The debris disposal device 452i includes at least one repositional substrate 459i having a capture material 445 positioned (e.g., coated) thereon. The repositional substrate 459i can be configured to capture or sequester at least one substance 453 from the body region to the repositional substrate 459i.

In an embodiment, the capture material 445 can include an adhesive material (e.g., adhesive material 456 of FIGS. 4D-4E) or absorbent material (e.g., absorbent material 458 of FIGS. 4F-4G). In an embodiment, the capture material 445 can include a binding element (e.g., a specific binding element such as an antibody, antibody fragment, a ligand, etc.).

In an embodiment, the repositionable substrate 459i can be a flexible, semi-rigid, or rigid substrate. The repositional substrate 459i can be attached to one or more structures 431i of the robotic debridement apparatus 400e in such a manner as to be storable and repositionable. In an embodiment, the repositionable substrate 459i is repositionable so that at least a portion of the repositionable substrate 459i is disposed in, above, or below an opening 403i defined by the housing 402i (e.g., exposed to the body region).

In an embodiment, the structures 431i are rotatable structures (e.g., rolling drums or pins). For example, the repositional substrate 459i can include a long, thin strip of paper, cloth, plastic, mesh, gel, or metal attached or mounted at one or more ends the rotatable structures. For example, the repositional substrate 459i can be held between a supply rotatable structure or a take-up rotatable structure. As such, the rotatable structures can advance the repositional substrate 459i to expose an unused portion of the repositional substrate 459i from the supply rotatable structure and collect a used portion of the repositional substrate 459i at the take-up rotatable structure. In an embodiment, at least the take-up rotatable structure can be position in a debris reservoir 441i disposed in or on the housing 402i.

In an embodiment, at least one of the structures 431i can be controllably rotated by one or more actuators 450i (e.g., motor or micromotor). The actuators 450*i* can rotate the at least one structure 431*i* responsive to direction from a controller 412*i*. The actuators 450*i* can be indirectly coupled to (e.g., via a belt), directly attached to, or incorporated into the at least one structure 431*i*. In an embodiment, at least one of the structures 431*i* can rotate passively. For example, the at least one structure 431*i* can be substantially in communication with the locomotive mechanism 404*i* and can advance with the self-propelling force.

In an embodiment, the repositionable substrate 459*i* is at least partially positioned within a debris reservoir 441*i*. For example, the repositionable substrate 459*i* can capture a substance 453 and deliver the substance 453 for storage in debris reservoir 441*i*. In an embodiment, the debris reservoir 441*i* can include energy-emitting device (not shown). For example, the energy-emitting device can deliver energy (e.g., electromagnetic energy) to the substance 453 captured by the repositional substrate 459*i* so as to degrade, destroy, or kill the substance 453. In an embodiment, the debris reservoir 441*i* can include a capture material (e.g., capture material 445 of FIG. 4A) or degrading agent (e.g., degrading agent 451 in FIG. 4B) disposed therein that is not attached to the repositional substrate 459*i*.

Figure 4J:
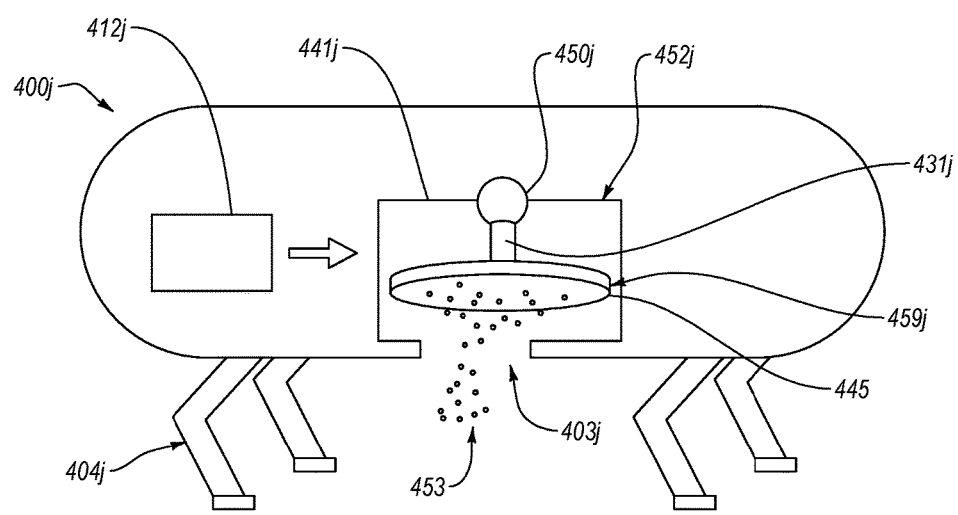

FIG. 4J illustrates an embodiment of a robotic debridement apparatus 400*j* that includes at least one debris disposal device 452*j*. The debris disposal device 452*i* includes at least one repositional substrate 459*j* that is at least partially positioned within a debris reservoir 441*j* and includes a capture material 445 configured to capture or sequester at least one substance 453. In an embodiment, the repositional substrate 459*j* can be a disc (e.g., substantially planar or curved disc). The debris disposal device 452*j* can also include at least one structure 431*i* having the repositional substrate 459*j* coupled thereto. In an embodiment, the structure 431*j* can be operably coupled to one or more actuators 450*j*. The actuators 450*j* can be configured to rotate, vibrate, or otherwise move the structure 431*j*, thereby moving the repositional substrate 459*j*. For example, the actuators 450*j* can move the repositional substrate 459*j* responsive to direction from the controller 412*j*. In an embodiment, the structure 431*i* can passively rotate the repositional substrate 459*j*. For example, the structure 431*j* can be substantially in communication with the locomotive mechanism 404*j* and can advance with the self-propelling force.

In an embodiment, a portion of the repositional substrate 459*j* is at least partially disposed in or above an opening 403*j* defined by the housing 402*j*. For example, rotating the repositional substrate 459*j* can cause an unexposed portion of the rotational substrate 459*j* to be exposed (e.g., positioned in or above the opening 403*j*) and an exposed portion of the rotational substrate 459*j* to be unexposed (e.g., positioned behind a portion of the housing 402*j*).

H. Therapeutic Devices

Figure 5A:
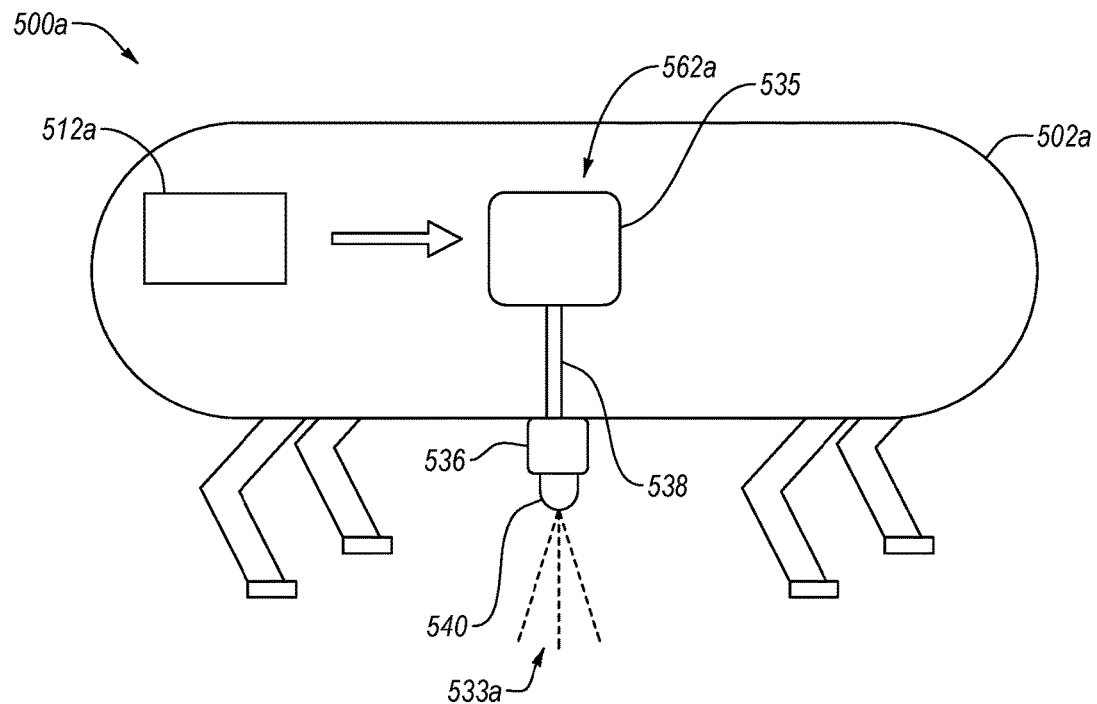
FIGS. 5A and 5B are schematic illustrations of robotic debridement apparatuses including different therapeutic devices, according to different embodiments.
Figure 5B:
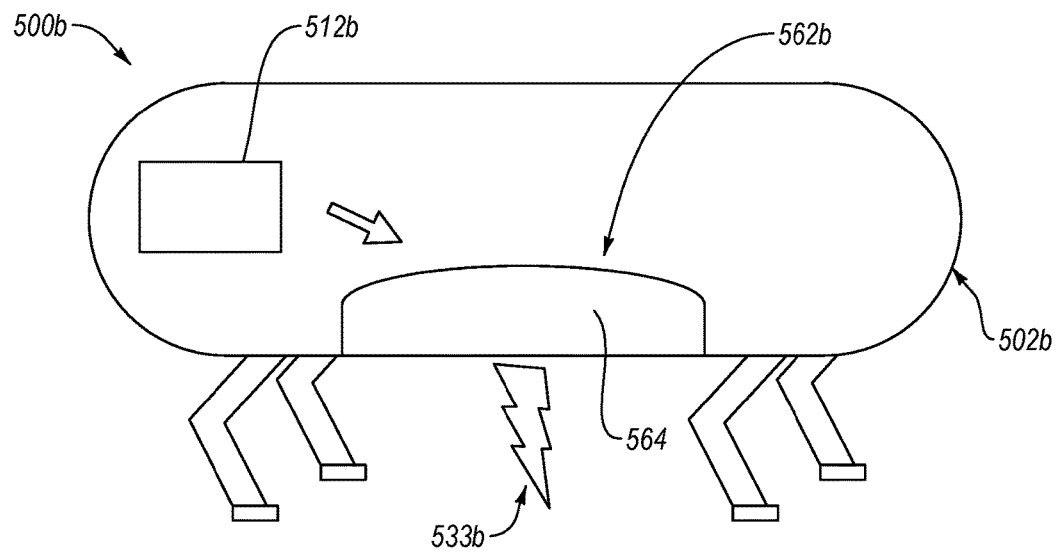

FIGS. 5A-5B are schematic illustrations of robotic debridement apparatuses including different therapeutic devices, according to different embodiments. Each of the different therapeutic devices shown in FIGS. 5A-5B are configured to provide a therapeutic effect to the body region. Except as otherwise described herein, the robotic debridement apparatuses shown in FIGS. 5A-5B and their materials, components, or elements can be similar to or the same as the robotic debridement apparatuses 100, 200*a-g*, 300*a-o*, 400*a-j* (FIGS. 1-4J) and their respective materials, components, or elements. For example, the robotic debridement apparatuses shown in FIGS. 5A-5B can include at least one of a housing, at least one locomotive mechanism, at least one debriding tool, at least one debris disposal device, one or more sensors, a controller, or a power source. Any of the therapeutic devices illustrated in FIGS. 5A-5B can be used in any of the robotic debridement apparatuses embodiments disclosed herein.

FIG. 5A illustrates an embodiment of a robotic debridement apparatus 500*a* that includes at least one therapeutic device 562*a*. In the illustrated embodiment, the therapeutic device 562*a* (e.g., a therapeutic agent-dispensing device) is configured to dispense one or more therapeutic agents 533*a* into or onto a body region. For example, the therapeutic device 562*a* can include at least one therapeutic agent reservoir 535 positioned in or on the housing 502*a*. The therapeutic agent reservoir 535 can be configured to store one or more therapeutic agents 533*a* therein. The therapeutic agent reservoir 535 can be fluidly coupled to at least one therapeutic-dispense element 536, for example, via conduit 538. In an embodiment, the therapeutic-dispense element 536 can be directly coupled to or integrally formed with the therapeutic agent reservoir 535. The therapeutic-dispense element 536 can be positioned in or on the housing 502*a* and include at least one therapeutic-dispense aperture 540 configured to dispense the therapeutic agents 533*a*. The at least one therapeutic-dispense aperture 540 can form part of a sprayer, a slit nozzle, etc. In an embodiment, the therapeutic device 562*a* is configured to dispense one or more therapeutic agents 533*a* in response to direction from a controller 512*a*.

In an embodiment, the therapeutic-dispense element 536 includes a brush-like structure in conjunction with or instead of a therapeutic-dispense aperture 540. The one or more therapeutic agents 533*a* can be dispersed throughout the brush-like structure. For example, the conduit 538 can disperse the therapeutic agents 533*a* throughout the brush-like structure. The brush-like structure is configured to paint the therapeutic agents 533*a* onto the body region as the brush-like structure moves relative to the body region (e.g., the brush-like structure moves relative to the housing 502*a* or the robotic debridement apparatus 500*a* moves relative to the body region). In an embodiment, the brush-like structure includes at least one three-dimensional printed micropillar structure.

The one or more therapeutic agents 533*a* are configured to provide a therapeutic effect to the body region. The therapeutic agents 533*a* can include a suitable gas, liquid, or solid that can provide a therapeutic effect to the body region. In an embodiment, the therapeutic agents 533*a* can include at least one of one or more medicaments, one or more anaesthetics, one or more antibiotics, one or more antimicrobials, one or more antiseptics (e.g., superoxidized water, oxidizing agents, hypochlorous acid, etc.), one or more healing agent, one or more coagulants, one or more anticoagulants, one or more anti-inflammatory agents, one or more hemostatic agent, one or more hormones (e.g., steroids, estrogens), one or more extracellular components (e.g., elastin or glycosaminoglycan), or one or more cells. Examples of antimicrobials include silver and silver compounds, iodine and iodine products, antimicrobial peptides (e.g., cathelicidins or defensins such as lucifensin), or chlorhexidine. In an embodiment, the therapeutic agents 533*a* can include an irrigation fluid. In an embodiment, the therapeutic agents 533*a* can include at least one of a natural healing agent or a synthetic healing agent. In an embodiment, the therapeutic agents 533*a* can include at least one of a protein, a lipid, an oil, a carbohydrate, an emulsion, a gel, or nanoparticles. In an embodiment, the therapeutic agents 533*a* can include at least one of one or more growth factors, one or more angiogenic factors, one or more cytokines (e.g., chemokines, interferons, interleukins, lymphokines, tumor necrosis factor. etc.), one or more vitamins, one or more minerals, one or more microbes, one or more pharmaceuticals, silicone, zinc, nitric oxide, synthetic dermis, or a liquid bandage. Examples of growth factors include at least one of interleukins, platelet derived growth factors, transforming growth factors, epidermal growth factors, fibroblast growth factors, vascular endothelial growth factors, insulin-like growth factors, or another suitable growth factors. Examples of vitamins and minerals that can be used as therapeutic agents 533a include at least one of vitamin A, vitamin C, vitamin D, magnesium, zinc, essential fatty acids, or other suitable vitamins or minerals. Examples of microbes that can be used as therapeutic agents 533a include one or more probiotics, other bacterium, live microorganism cultures, cells for cell grafts, etc. Examples of cells that can be used for cell grafts include stem cells (e.g., from embryonic, bone marrow, liver, spleen, lymph node, peripheral blood sources, or the like), lymphocytes, myelocytes, megakaryocytes, epithelial cells, dermal cells, engineered tissue, biological skin substitute (e.g., apligraf), or other suitable cells. In an embodiment, the therapeutic agents 533a can include one or more collagens, elastin, fibronectin, laminin, glycosaminoglycans, proteoglycans, hyaluronic acid, chondroitin sulfate, heparin sulfate, keratin sulfate, chitosan, gelatin, allantoin, urea, phenylacetic acid, phenylacetaldehyde, or calcium carbonate. In an embodiment, the therapeutic agents 533a can include one or more chemicals configured to increase blood flow to the body region. In an embodiment, the therapeutic agents 533a can include a combination of any of the therapeutics agents disclosed herein.

FIG. 5B illustrates an embodiment of a robotic debridement apparatus 500b that includes at least one therapeutic device 562b including at least one energy-emitting device 564 positioned in or on a housing 502b of the robotic debridement apparatus 500b. In an embodiment, the energy-emitting device 564 can be configured to emit energy 533b responsive to direction from a controller 512b.

The energy-emitting device 564 can be configured to emit energy 533b that is configured to at least one of disinfect or sterilize the body region (e.g., disinfect or sterilize the body region of at least one of one or more bacteria, one or more archaea, one or more protozoa, one or more algae, one or more fungi, one or more viruses, or one or more organisms), increase a rate of healing (e.g., increase blood flow), or otherwise provide a therapeutic effect to the body region. For example, the energy-emitting device 564 can be configured to emit or absorb energy 533b, such as electromagnetic energy, acoustic energy, electrical energy, thermal energy, or any other suitable energy.

In an embodiment, the energy-emitting device 564 includes an electromagnetic device. The electromagnetic device is configured to emit energy 533b as electromagnetic energy that irradiates at least a portion of the body region. For example, the emitted electromagnetic energy can exhibit a wavelength or wavelength range for disinfecting, sterilizing, healing (e.g., low-intensity laser irradiation (LILI) or phototherapy), promoting angiogenesis, or otherwise providing a therapeutic effect to the body region. For instance, exposure of wounds to the electromagnetic energy (e.g., in the blue spectrum or the red spectrum) can increase cell migration, viability, and proliferation. In an embodiment, the electromagnetic device can be configured to emit energy 533b (e.g., ultraviolet light) to disinfect or sterilize the body region.

In an embodiment, the electromagnetic device can include at least one of one or more fluorescent light bulbs, one or more incandescent light bulbs, one or more high-intensity discharge bulbs, one or more mercury-vapor light sources, one or more short wave ultraviolet lamps, one or more gas-discharge lamps, one or more LEDs, one or more lasers, or another type of electromagnetic source. In an embodiment, the energy-emitting device 564 can emit electromagnetic energy at a wavelength that stimulates healing of a tissue. For example, the electromagnetic device can be configured to emit electromagnetic energy having a wavelength of about 10 nm to about 800 nm, such as about 400 nm to about 800 nm, about 380 nm to about 450 nm, about 315 nm to about 400 nm, about 280 nm to about 315 nm, about 100 nm to about 280 nm, about 300 nm to about 400 nm, about 10 nm to about 100 nm or about 200 nm to about 300 nm. In an embodiment, the electromagnetic device can include at least one quantum dot.

In an embodiment, the therapeutic device 562b can further include one or more photocatalytic particles (not shown) positioned on the housing 502d. The photocatalytic particles can include any particle that exhibits biocidal activity when activated (e.g., irradiated) by the electromagnetic energy emitted from the electromagnetic device. For example, the photocatalytic particles can include zinc oxide particles or other suitable photocatalytic. In an embodiment, the photocatalytic particles can include nanoparticles or other particles exhibiting a relatively high surface area.

In an embodiment, the energy-emitting device 564 includes an acoustic energy source. The acoustic energy source is configured to emit energy 533b that is acoustic energy. For example, the energy-emitting device 564 is configured to emit sound waves (e.g., high intensity ultrasound) to promote wound healing. In an embodiment, the energy-emitting device 564 can include at least one ultrasound transducer.

In an embodiment, the energy-emitting device 564 includes an electrical energy source. The electrical energy source is configured to emit energy 533b that is electrical energy. For example, the electrical energy source can be configured to emit electrical energy configured to disinfect the body region, sterilize the body region, increase blood flow to the body region, etc. In an embodiment, the electrical energy source can include at least two electrodes (not shown) that are exposed to and configured to disinfect or sterilize the body region (e.g., electrochemical disinfection). The at least two electrodes can be configured to have an electrical potential therebetween. For example, the electrical potential between the electrodes can cause an electrical current to pass between the electrodes, for example, through a fluid therebetween (e.g., one or more agents, exudate, etc.). The electric current can cause an electrochemical production of disinfecting or sterilization agents from the fluid.

In an embodiment, the energy-emitting device 564 includes a thermal energy source. The thermal energy source is configured to emit energy 533b that is thermal energy. For example, the thermal energy source can include an electrical resistive heater, an infrared heater, or another suitable thermal energy source.

In an embodiment, the thermal energy source can be configured to stimulate a portion of the body region. For example, the thermal energy source can directly stimulate (e.g., contact) a portion of the body region. For example, the thermal energy source can indirectly stimulate a portion of the body region by illuminating the body region or heating one or more fluids that are dispensed from the robotic debridement apparatus 500b (e.g., heat the fluids before, during, or after the fluids are dispensed from the robotic debridement apparatus 500b).

In an embodiment, the thermal energy source can heat a portion of the body region to a temperature sufficient to disinfect or sterilize the portion of the body region, such as at least about 70° C., at least about 80° C., at least about 90° C., at least about 100° C., at least about 120° C., or about 80° C. to about 95° C. In an embodiment, the thermal energy source can heat a portion of the body region to a temperature sufficient to facilitate healing (e.g., increase blood flow) of the portion of the body region, such as about ambient temperature to about 70° C.

In an embodiment, the energy-emitting device 564 can be replaced with or operate in tandem with an energy-absorbing device (not shown) For example, the energy-absorbing device can include a heat sink that is configured to reduce a temperature of a portion of the body region. For example, the heat sink can reduce the temperature of a portion of the body region below ambient temperature to reduce inflammation of and pain from the body region.

In an embodiment, the components, elements, or features of the robotic debridement apparatuses 100, 200a-g, 300a-o, 400a-j (FIGS. 1-4J) can be modified to form a therapeutic device that provides a therapeutic effect to the body region. For example, the locomotive mechanism 104 (FIG. 1) can be used to agitate the body region thereby increasing blood flow to the body region. In an embodiment, the energy-emitting device 334 (FIG. 3H) can be configured to transmit high-frequency ultrasonic energy or low-frequency ultrasonic energy to the body region which can cause a thermal effect that increases blood flow to the body region.

I. Marking Devices

Figure 6:
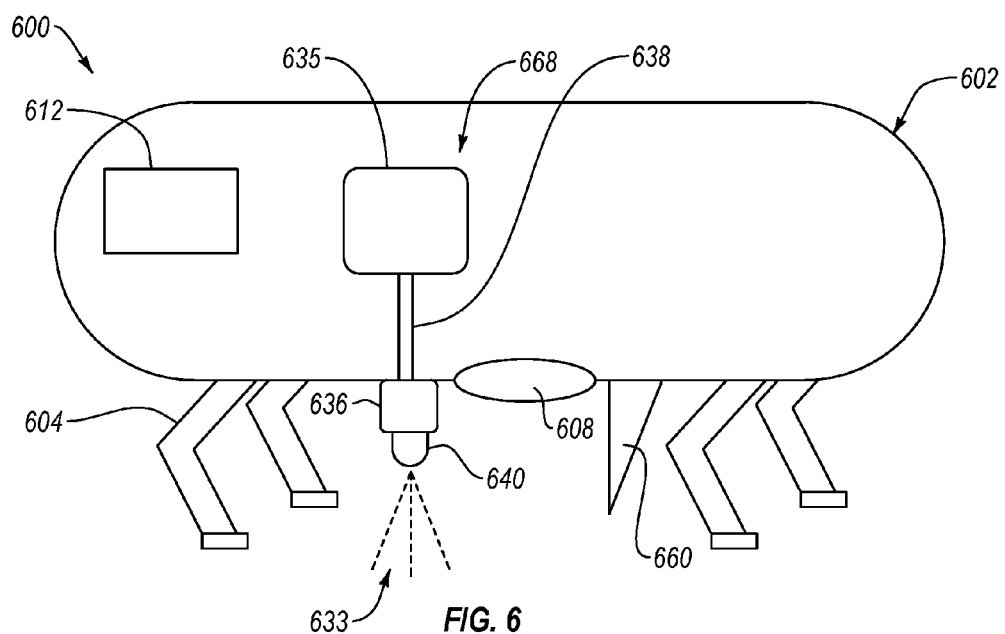
FIG. 6 is a schematic illustration of a robotic debridement apparatus that includes at least one marking device, according to an embodiment.

FIG. 6 is a schematic illustration of a robotic debridement apparatus 600 that includes at least one marking device 668, according to an embodiment. Except as otherwise described herein, the robotic debridement apparatus 600 shown in FIG. 6 and its materials, components, or elements can be similar to or the same as the robotic debridement apparatuses 100, 200a-g, 300a-o, 400a-j, 500a-b (FIGS. 1-5B) and their respective materials, components, or elements. For example, the robotic debridement apparatus 600 shown in FIG. 6 includes a housing 602, at least one locomotive mechanism 604, and at least one of at least one debriding tool (e.g., any of the debriding tools 306a-o of FIGS. 3A-3O) or at least one debris disposal device (e.g., any of the debris disposal devices 452a-j of FIGS. 4A-4J), and, optionally, at least one therapeutic device (e.g., any of the therapeutic devices 562a-b of FIGS. 5A-5B), one or more sensors 608, a controller 612, or a power source (not shown). The marking device 668 illustrated in FIG. 6 can be used in any of the robotic debridement apparatuses embodiments disclosed herein.

In the illustrated embodiment, the robotic debridement apparatus 600 includes at least one device 660 positioned in or on the housing 602. The device 660 can include at least one debriding tool or at least one debris disposal device.

The at least one marking device 668 is positioned in or on the housing 602. The marking device 668 is configured to dispense one or more taggants 633 into or onto the body region. In the illustrated embodiment, the marking device 668 includes at least one taggant reservoir 635 positioned in or on the housing 602 that is configured to store the taggants 633 therein. The taggant reservoir 635 is fluidly coupled to at least one taggant-dispense element 636 via, for example, a conduit 638. The taggant-dispense element 636 can be positioned in or on the housing 602. In particular, the taggant-dispense element 636 includes at least one taggant-dispense aperture 640 through which the taggants 633 are dispensed into or onto the body region. The at least one taggant-dispense aperture 640 can form part of a sprayer, a slit nozzle, etc. In an embodiment, the taggant-dispense element 636 is configured to dispense the taggants 633 responsive to direction from a controller.

In an embodiment, the taggant-dispense element 636 includes a brush-like structure in conjunction with or instead of a taggant-dispense aperture 540. The one or more taggants 633 can be dispersed throughout the brush-like structure. For example, the conduit 638 can disperse the taggants 633 throughout the brush-like structure. The brush-like structure is configured to paint the taggants 633 onto the body region as the brush-like structure moves relative to the body region (e.g., the brush-like structure moves relative to the housing 602 or the robotic debridement apparatus 600 moves relative to the body region). In an embodiment, the brush-like structure includes at least one three-dimensional printed micropillar structure.

The taggants 633 can include any chemical taggant, radiological taggant, or physical taggant that can be detected by any of the sensors disclosed herein. In an embodiment, the taggants 633 can be detected by an optical sensor. For example, the taggants 633 can include one or more chromogens, one or more dyes, one or more luminescent (e.g., chemiluminescent) materials, or one or more fluorogenic materials. In an embodiment, the taggants 633 can be more dense than the surrounding tissue. In an embodiment, the taggants 633 can be less dense than the surrounding tissue. Taggants 633 that are more or less dense than surrounding tissue can be detected by an acoustic sensor. In an embodiment, the taggants 633 can be detected by a chemical sensor. For example, the taggants 633 can include at least one chemical (e.g., at least one acid, at least one base) that changes the pH of the body region that can be detected by a pH meter. In an embodiment, the taggants 633 can include at least one protein that can be detected by a protein sensor. In an embodiment, the taggants 633 can include at least one gas that can be detected by a gas sensor. In an embodiment, the taggants 633 can change the electrical conductivity (e.g., a conductive taggant or an insulating taggant) of the body region, which can be detected by an electrical conductivity sensor. In an embodiment, the taggants 633 can change the moisture level of the body region, which can be detected by a moisture sensor. In an embodiment, the taggants 633 can include at least one biocompatible chemical or physical taggant. In an embodiment, the taggants 633 can include any suitable taggant or a combination of any of the taggants 633 disclosed herein.

In an embodiment, the taggants 633 include at least one component that specifically or nonspecifically directly reacts with a target (e.g., a tissue, a cell, or a debris material). For example, the taggants 633 can include a dye (e.g., a lipophilic dye, a nucleic acid dye, a Schiff reagent) that reacts with a type of tissue component (e.g. an intact cell membrane) or debris (e.g., a microbial component, such as a glycoprotein, or intracellular components indicative of cell death). For example, the taggants 633 can include a chromogen that is detectable by an optical sensor. For example, the taggants 633 can be a live cell stain (e.g., Bismarck brown or Vibrant stain). In an embodiment, the taggants 633 include at least one component that does not directly or indirectly react with tissue or debris. For example, the taggants 633 can include a nonstaining colorant used to indicate a path.

In an embodiment, the taggants 633 includes at least one component that recognizes and binds to a target. In an embodiment, the taggant 633 includes a conjugated compound having a recognition element and a reporting tag. For example, the taggant 633 can include a recognition element (e.g., an antibody, an aptamer, a lectin, a natural binding element, or a synthetic binding element) that is able to specifically recognize and bind a specific target molecule (e.g., a specific cell type, a specific microbe, a specific protein, a specific peptide, a specific oligosaccharide, a specific lipid, a specific nucleic acid sequence, etc.) or specific class (e.g., a protein, a lipid, a carbohydrate, a glycosaminoglycan, a nucleic acid, etc.). The recognition molecule can be conjugated to a tag (e.g., a chromogen, a fluorescent agent, a luminescent agent, a quantum dot, a radiolabel, a magnetic or paramagnetic tag, a volatile tag, a mass tag, a metallic tag, an electroactive tag, an energy transfer tag (e.g., FRET or CRET), a two-step tag (e.g., avidin-biotin tag), or any other tag) that is detectable by a sensor (e.g., sensors 608). In an example, the taggants 633 can include a recognition element that recognizes and binds to High Mobility Group Box 1 protein, which is released from necrotic cells. In an example, the taggants 633 can include a recognition element that recognizes and binds to a compound indicative of necrotic tissue, such as a heat shock protein, cytochrome c, vimentin, lamin A, soluble galactose-binding lectin 7, or calreticulin. In an example, the taggants 633 can include a recognition element that recognizes and binds to a compound (e.g., fibronectin or a growth factor) indicative of newly growing tissue (e.g., which should not be debrided, but which may benefit from a therapeutic agent). In an example, the taggants 633 can include a recognition element that recognizes and binds to an inflammatory marker indicative of a wound. In an example, the taggants 633 can include a recognition element that recognizes and binds to a microbe such as a type of bacteria. In an example, the taggants 633 can include a recognition element that recognizes and binds to another taggant. For example, the taggants 633 can include a recognition element (e.g., secondary antibody or avidin complex) that carries a tag and recognizes a previously dispensed taggant (e.g., a primary antibody or conjugated biotin molecule)

In an embodiment, one or more of the taggants 633 or sensors 608 can detect and quantify a target. For example, the target can be present in low quantities in healing tissue but be present at high quantities in necrotic tissue.

In an embodiment, the taggants 633 include a labeled substrate for an enzyme. For example, the taggants 633 can include a substrate having a label that is released upon cleavage by the target enzyme and is detectable by a sensor 608. For example, the taggants 633 could include a labeled substrate able to be cleaved by a galactosidase or by glyceraldehyde phosphate dehydrogenase, both of which are associated with necrotic tissue. For example, the taggants 633 can include an electron transfer molecule (e.g., FRET or CRET) that can be cleaved by the enzyme. For example, the taggants 633 could include a labeled substrate carrying an electroactive label.

In an embodiment, the marking device 668 can be configured to dispense the one or more taggants 633 (e.g., a chromogen) into or onto the body region to indicate that the robotic debridement apparatus 600 has performed or has not performed a task. As such, the taggants 633 can indicate information (e.g., a task was performed) when detected (e.g., by the sensors 608). For example, the marking device 668 can dispense the taggants 633 when the locomotive mechanism 604 is activated (e.g., as the robotic debridement apparatus 600 travels). For example, dispensing the taggant when the locomotive mechanism 604 is active can indicate the path that the robotic debridement apparatus 600 has traveled within the body region. In an embodiment, the marking device 668 can dispense the taggants 633 when the robotic debridement apparatus 600 uses at least one debriding tool to debride tissue. In an embodiment, the marking device 668 can dispense the taggants 633 when the robotic debridement apparatus 600 uses at least one debris disposal device to capture at least one substance from the body region. In an embodiment, the marking device 668 can dispense the taggants 633 when the robotic debridement apparatus 600 uses at least one therapeutic device to provide a therapeutic effect to the body region. In an embodiment, the marking device 668 can be configured to dispense the taggants 633 to indicate completion of a task performed by the robotic debridement apparatus 600 or that the robotic debridement apparatus 600 did not complete a task (e.g., when additional work is needed). For example, the marking device 668 can dispense the taggants 633 when the robotic debridement apparatus 600 finishes debriding tissue at a selected portion of the body region. In an embodiment, the marking device 668 can dispense a taggant when the robotic debridement apparatus 600 is unable to completely debride tissue from a selected portion of the body region. In an embodiment, the marking device 668 can be configured to dispense the taggants 633 responsive to direction from a controller.

In an embodiment, the marking device 668 can be configured to dispense the one or more taggants 633 (e.g., a chromogen) into or onto the body region to indicate a route taken by the robotic debridement apparatus 600. For example, the taggants 633 can be dispensed (e.g., under direction of a controller 612) when the locomotive mechanism 604 is activated. For example, the taggants 633 can be dispensed (e.g., under direction of a controller 612) when the device 660 (e.g., debriding tool) has been activated. For example, the taggants 633 can be dispensed to determine if a marker is present indicating an area that has been debrided. In an embodiment the marking device 668 and the sensors 608 or other sensors (e.g., on one or more other robotic debridement apparatuses) are configured to act in concert to map at least one of a route taken by the robotic debridement apparatus 600, an area of the body region that has been debrided by the robotic debridement apparatus 600, an area of the body region that is in need of being debrided by the robotic debridement apparatus 600, or some other information. In an embodiment, information regarding the mapping is stored in memory (e.g., memory 122 of FIG. 1). In an embodiment, information regarding the mapping is transmitted to an external device (e.g., external device 127 of FIG. 1).

In an embodiment, the marking device 668 can dispense the taggants 633 to detect and indicate information about the body region. For example, the marking device 668 can dispense one or more taggants 663 that recognize and bind to a specific target to detect the presence or absence of the target and thereby indicate the presence or absence of a type of tissue (e.g., necrotic tissue, debrided tissue, granulated tissue), a type of cell (e.g., a blood cell such as a neutrophil, lymphocyte, macrophage, or erythrocyte; a fibroblast; an epithelial cell, etc.), a type of microbe, or a type of debris (e.g., intracellular components indicating cell death and/or debridement, microbial components, etc.).

In an embodiment, each of the taggants 633 dispensed by the marking device 668 can indicate different information. For example, the marking device 668 can be configured to dispense at least one of a first, second, third, fourth, fifth, or sixth taggant. For example, the first taggant can be dispensed (e.g., under direction of a controller 612) when the locomotive mechanism 604 is activated, the second taggant can be dispensed when the debriding tool (e.g., device 660) is used, the third taggant can be dispensed when the debris disposal device (e.g., device 660) is used, the fourth taggant can be dispensed when the therapeutic device (not shown) is used, the fifth taggant can be dispensed when the robotic debridement apparatus 600 completes a certain task, and the sixth taggant can be dispensed when the robotic debridement apparatus 600 fails to complete a certain task.

In an embodiment, each of the taggants 633 dispensed by the marking device 668 can be dispensed to detect the presence, absence, or quantity of a specific target. For instance, each of the first, second, third, fourth, fifth, or sixth taggants can be dispensed to detect the presence, absence, or quantity a different specific targets. In an embodiment, the taggants 633 dispensed by the marking device 668 can be dispensed simultaneously, concurrently, or in a sequence (e.g., under direction of a controller 612). For example, the taggants 633 can be dispensed continuously, in a pulsed manner, or in a timed manner under direction of a controller 612. In an embodiment, each of the first, second, third, fourth, fifth, and sixth taggants can be different from each other. The first, second, third, fourth, fifth, and sixth taggants can be distinguished from each other by a single sensor 608 positioned in or on the housing 602, a plurality of sensors (not shown) positioned in or on the housing 602, or one or more sensors (not shown) spaced from the robotic debridement apparatus 600 (e.g., one or more sensors positioned in or on a housing of another robotic debridement apparatus).

In an embodiment, any of the taggants 633 can be detected by a single sensor 608 positioned in or on the housing 602, a plurality of sensors (not shown) positioned in or on the housing 602, or one or more sensors (not shown) spaced from the robotic debridement apparatus 600 (e.g., one or more sensors positioned in or on a housing of another robotic debridement apparatus or a dressing). In an embodiment, the marking device 668 and at least one sensor (e.g., one or more sensors 608 or one or more sensors positioned in or on a housing of another robotic debridement apparatus) are configured to function in concert.

Figure 11A:
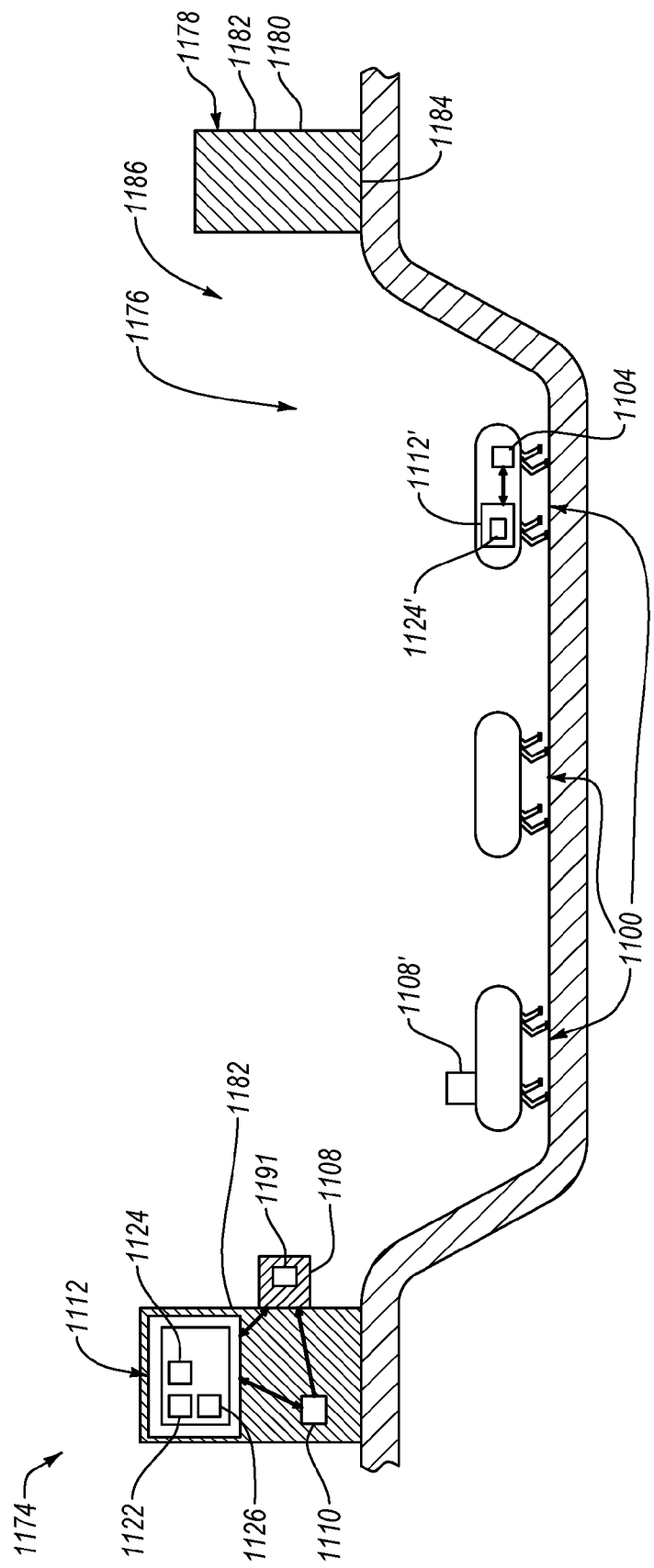
FIGS. 11A and 11B are schematic illustrations of a system that includes a dressing that is associated with a plurality of robotic debridement apparatuses, according to an embodiment.

In an embodiment, the marking device 668 can include or be coupled to a transceiver (not shown) configured to receive one or more signals from at least one device (e.g., controller 612, external device 127 of FIG. 1, or a different robotic debridement apparatus, or controller 1112 of FIG. 11A). The signals can include information regarding the operation of the marking device 668 encoded therein. For example, the signals can include directions regarding at least one of when the taggants 633 are to be dispensed, which taggants 633 are to be dispensed, in what order the taggants 633 are to be dispensed, where the taggants 633 are to be dispensed, etc. In an embodiment, the transceiver can be configured to transmit one or more signals to at least one device (e.g., controller 612, external device 127 of FIG. 1, a different robotic debridement apparatus, or controller 1112 of FIG. 11A). The signals can include information regarding the operation of the marking device 668 encoded therein. For example, the signals can include at least one of when the taggants 633 were dispensed, where the taggants 633 were dispensed, what taggants 633 were dispensed, etc. The signals can be used to determine what has been performed by the robotic debridement apparatus 600, what further needs to be performed, where to send other robotic debridement apparatuses, etc.

J. Extraction Devices

Figure 7:
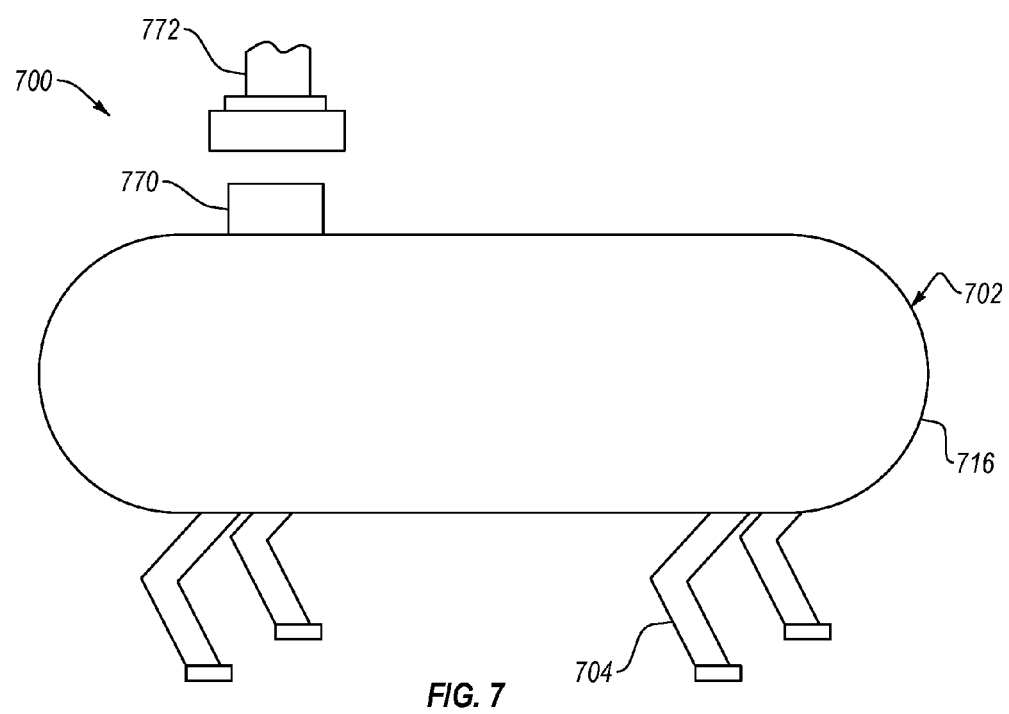
FIG. 7 is a schematic illustration of a robotic debridement apparatus that includes at least one extraction device, according to an embodiment.

FIG. 7 is a schematic illustration of a robotic debridement apparatus 700 that includes at least one extraction device 770, according to an embodiment. Except as otherwise described herein, the robotic debridement apparatus 700 shown in FIG. 7 and its materials, components, or elements can be similar to or the same as the robotic debridement apparatuses 100, 200a-g, 300a-o, 400a-j, 500a-b, 600 (FIGS. 1-6) and their respective materials, components, or elements. For example, the robotic debridement apparatus 700 shown in FIG. 7 can include one or more of at least one locomotive mechanism 704, at least one debriding tool (not shown) or at least one debris disposal device (not shown), and optionally, one or more sensors (not shown), a controller (not shown), or a power source (not shown). The extraction device 770 illustrated in FIG. 7 can be used in any of the robotic debridement apparatus embodiments disclosed herein.

In the illustrated embodiment, the robotic debridement apparatus 700 includes a housing 702. The robotic debridement apparatus 700 also includes at least one extraction device 770 positioned in or on the housing 702. The extraction device 770 can include any device configured to facilitate removal of the robotic debridement apparatus 700 to or from the body region. In an embodiment, the extraction device 770 is configured to facilitate removal of the robotic debridement apparatus 700 using at least one retrieval device 772 that is not positioned in or on the housing 702. For example, the extraction and retrieval devices 770, 772 are configured to be coupleable together.

In an embodiment, the extraction device 770 can include a magnet. In such an embodiment, the retrieval device 772 can include an oppositely poled magnet or a magnetically attractable material. As such, positioning the retrieval device 772 proximate to the extraction device 770 can cause the extraction device 770 to be coupled to the retrieval device 772. In an embodiment, the extraction device 770 can include a magnetically attractable material and the retrieval device 772 can include a magnet.

In an embodiment, the extraction device 770 can include at least one protruding element extending outwardly from an outer surface 716 of the housing 702. The protruding element can include a fin, a loop, a protruding element defining a hole therethrough, a protruding element having a notch formed therein, or any other suitable protruding element. In such an embodiment, the retrieval device 772 can include a device that can connect to, hook, grasp, or otherwise couple to the protruding element. For example, the retrieval device 772 can include forceps configured to grasp the protruding element, a hook configured to connect to the protruding element (e.g., a loop), a tether configured to be tied to or otherwise attached to the protruding element, or another suitable device. In an embodiment, the extraction device 770 can include an attachment location (not shown). The attachment location does not protrude from the outer surface 716 and is positioned on or integrally formed with a part of the housing 702 that can support the entire weight of the robotic debridement apparatus 700. For example, the attachment location can be on the outer surface 716 and exhibit at least one of a surface that can have an adhesive applied thereto, a recessed loop (e.g., configured to have a tether threaded therethrough), or a hole defined by the housing 702. In such an embodiment, the retrieval device 772 can include a tether (e.g., glued to the surface, threaded through the recessed loop, or extending through the hole), a hook (e.g., extending through the recessed loop or through the hole), or another suitable device.

In an embodiment, the retrieval device 772 can be integrally formed with or otherwise coupled to a device that is spaced or distinct from the robotic debridement apparatus 700. For example, the retrieval device 772 can be coupled to a dressing (e.g., dressing 2178 of FIG. 21). As such, removing or attaching the dressing from the body region can also dispose or remove the robotic debridement apparatus 700 to or from the body region, respectively. In an embodiment, the retrieval device 772 can be a tool (e.g., forceps) used by a user (e.g., the subject or a care provider).

In an embodiment, the retrieval device 772 does not prevent the robotic debridement apparatus 700 from including a freestanding housing 702. For example, the retrieval device 772 can be coupled to the robotic debridement apparatus 700 (e.g., using a tether), while the robotic debridement apparatus 700 is positioned within the body region. However, the retrieval device 772 does not actively support the robotic debridement apparatus 700 while the robotic debridement apparatus 700 operates in the body region.

K. Methods Employing a Robotic Debridement Apparatus

Figure 8:
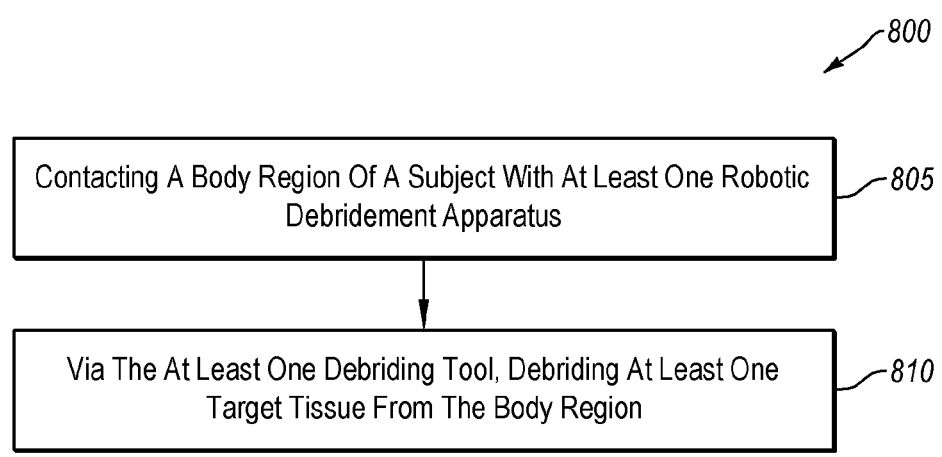
FIGS. 8 and 9 are flow diagrams of different methods of using any of the robotic debridement apparatuses disclosed herein, according to different embodiments.

FIG. 8 is a flow diagram of a method 800 of using any of the robotic debridement apparatuses disclosed herein, according to an embodiment. In an embodiment, some of the acts of the method 800 can be split into a plurality of acts, some of the acts can be combined into a single act, and some acts can be omitted. Also, it is understood that additional acts can be added to the method 800. Except as otherwise disclosed herein, the acts of method 800 can be used with any of the robotic debridement apparatuses 100, 200*a-g*, 300*a-0*, 400*a-j*, 500*a-b*, 600, 700, 1000 (FIGS. 1-7, 10) disclosed herein.

Act 805 includes contacting a body region of a subject with at least one robotic debridement apparatus. For example, the at least one robotic debridement apparatus can include a housing, at least one locomotive mechanism positioned in or on the housing, and at least one debriding tool associated with the housing. In an embodiment, the at least one robotic debridement apparatus can include at least one debris disposal device or at least one therapeutic device. In an embodiment, the at least one robotic debridement apparatus can include one or more sensors, a controller, a power source, at least one marking device, or at least one extraction device.

In an embodiment, contacting a body region of a subject with at least one robotic debridement apparatus can include manually placing, manually positioning, using at least one extraction device or retrieval device, or another suitable method of contacting the at least one robotic debridement apparatus over the body region. In an embodiment, as will be discussed in more detail later, contacting a body region of a subject with at least one robotic debridement apparatus reversibly attaching a (e.g., dressing 1178 of FIGS. 11A-11B) associated with the plurality of robotic debridement apparatuses to the body region.

Act 810 includes, via the at least one debriding tool, debriding at least one target tissue from the body region. For example, the at least one debriding tool can debride viable tissue or, more preferentially, nonviable tissue (e.g., with minimal debridement of healthy tissue). In an embodiment, the debriding tool can debride tissue using any of the methods disclosed herein. For example, the debriding tool can debride tissue from the body region as a housing of the robotic debridement apparatus travels relative to the body region. For example, the debriding tool can debride tissue by cutting, scraping, or abrading tissue using at least one blade (FIGS. 3A-3D). In an embodiment, the debriding tool can debride tissue from the body region by moving an abrasive material against the tissue (FIGS. 3E-3G). For example, the debriding tool can debride tissue from the body region by emitting energy (e.g., acoustic energy, electromagnetic energy) into the body region (FIG. 3H). For example, the debriding tool can debride tissue from the body region by dispensing one or more debriding agents or pressurized fluids into the body region (FIGS. 3I-3J). For example, the debriding tool can debride tissue from the body region using a body coupled to and distinct from the housing (FIGS. 3K-3L). The body can debride tissue from the body region by being dragged behind the housing or using at least one locomotive mechanism positioned in or on the body. For example, the debriding tool can debride tissue from the body region by moving relative to the housing (FIGS. 3M-3O).

In an embodiment, the at least one locomotive mechanism of the at least one robotic debridement apparatus can be activated to relocate the at least one robotic debridement apparatus relative to the body region. In an embodiment, robotic debridement apparatus can travel by means of the locomotive mechanism using any methods disclosed herein. For example, the locomotive mechanism can include at least one piezoelectric material, and activating the piezoelectric material can move its respective robotic debridement apparatus (FIGS. 2E-2F), allowing the robotic debridement apparatus to travel across the body region. In an embodiment, the locomotive mechanism can include at least one impelling mechanism, and moving the impelling mechanism can move its respective robotic debridement apparatus (FIGS. 1, 2C-2D), allowing the robotic debridement apparatus to travel across the body region. In an embodiment, the locomotive mechanism can include at least one shape memory alloy, and stimulating (e.g., heating) the shape memory alloy can induce movement in its respective robotic debridement apparatus, allowing the robotic debridement apparatus to travel across the body region. In an embodiment, the locomotive mechanism can include at least one bellows, and expanding the at least one bellows can induce movement in its respective robotic debridement apparatus, allowing the robotic debridement apparatus to travel across the body region (FIG. 2B). In an embodiment, activating the locomotive mechanism can cause at least one debriding tool coupled to debride tissue from the wound.

In an embodiment, the at least one robotic debridement apparatus can include the at least one debris disposal device that can capture at least one substance from the body region. In an embodiment, the debris disposal device can capture the at least one substance from the body region using any of the methods disclosed herein. For example, the debris disposal device can suction the at least one substance from the body region (FIG. 4C). For example, the debris disposal device can adhere or attach thereto the at least one substance from the body region (FIGS. 4A, 4D-4E, 4I-4J). For example, the debris disposal device can absorb or attach thereto the at least one substance from the body region (FIGS. 4A, 4F-4G, 4I-4J). For example, the debris disposal device can dispense one or more pressurized fluids (FIG. 4H) into or onto the body region.

In an embodiment, the at least one robotic debridement apparatus can include at least one therapeutic device that can provide a therapeutic effect to the body region. In an embodiment, the therapeutic device can provide the therapeutic effect to the body region using any of the methods disclosed herein. For example, the therapeutic device can dispense one or more therapeutic agents into or onto the body region (FIG. 5A). For example, the therapeutic device can emit energy (e.g., light, acoustic energy, electrical energy, or thermal energy) into or onto the body region (FIG. 5B).

In an embodiment, the at least one robotic debridement apparatus can include one or more sensors (e.g., sensors 108 of FIG. 1) that detect one or more characteristics of the body region. In an embodiment, the characteristics that the sensors detect can include a certain type of tissue (e.g., at least one target tissue). For example, the sensors can detect viable tissue, or nonviable tissue. For instance, the sensors can detect new healthy tissue, established healthy tissue, necrotic tissue, ischemic tissue, slough, fibrinous tissue, granulated tissue, or another type of tissue. In an embodiment, the characteristics that the sensors detect can include microbes, toxins, or inflammation. In an embodiment, the sensors can distinguish between two different types of tissue. For example, the sensors can distinguish between viable tissue and nonviable tissue, necrotic tissue and non-necrotic tissue, healthy tissue and inflamed tissue, etc. In an embodiment, the sensors can detect the presence of one or more agents. For example, the sensors can detect one or more debriding agents, one or more therapeutic agents, or one or more taggants. In an embodiment, the sensors can distinguish between the different agents. For example, the sensors can distinguish between a first taggant and a second taggant. In an embodiment, the sensors can detect at least one of the presence, identification, functionality, status, or condition of robotic debridement apparatus positioned in the body region. In an embodiment, the sensors can transmit one or more sensing signals responsive to detecting the one or more characteristics. For example, the sensors can transmit the sensing signals to a controller (e.g., controller 112 of FIG. 1). In an embodiment, the sensors can detect the characteristics of the body region or transmit the sensing signals responsive to direction from the controller.

Figure 11B:
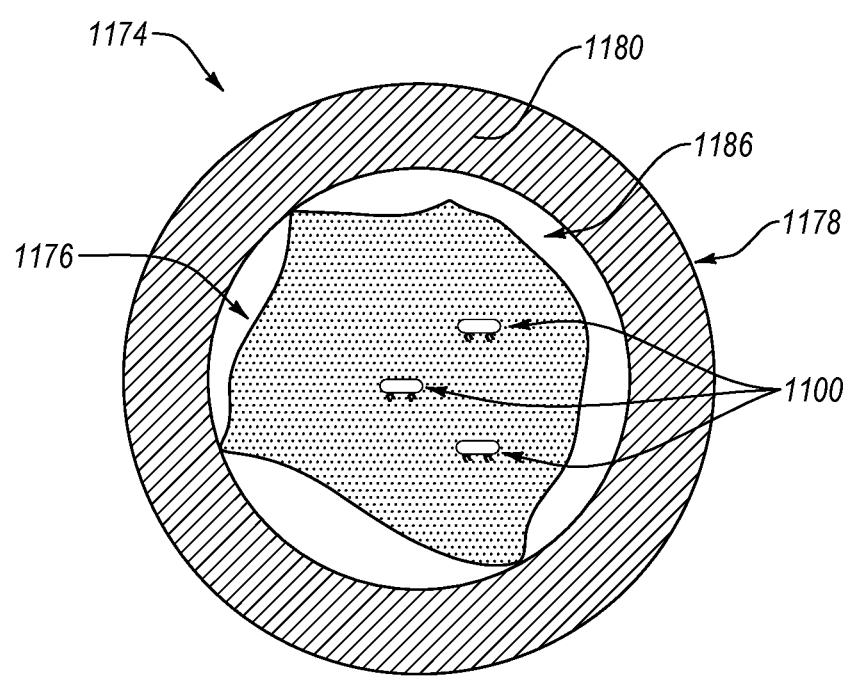

In an embodiment, one or more components of the at least one robotic debridement apparatus can operate under direction from a controller (e.g., controller 112 of FIG. 1, controller 1112 of FIGS. 11A-11B). For example, the locomotive mechanism can be controllably activated and controllably relocate the at least one robotic debridement apparatus, the debriding tool can controllably debride tissue, the debris disposal device can controllably capture the at least one substance, the therapeutic device can controllably provide the therapeutic effect to the body region, the power source can controllably supply power to one or more components of the at least one respective robotic debridement apparatus, or the marking device can controllably dispense one or more taggants into the body region responsive to direction from the controller. In an embodiment, the controller can control one or more components of at least one of the robotic debridement apparatuses responsive to one or more operational instructions stored on memory or received by a transceiver.

In an embodiment, the controller can control the operation of the one or more components of the at least one robotic debridement apparatus responsive to one or more sensing signals received from the sensors. For example, the controller can direct the locomotive mechanism to controllably relocate the at least one robotic debridement apparatus to a location having undebrided unhealthy tissue, a location having at least one substance to be disposed, or a portion of the body region requiring a therapeutic effect responsive to the sensing signals. In an embodiment, the controller can direct the locomotive mechanism to controllably relocate the at least one robotic debridement apparatus away from a location having healthy tissue, a location that was previously debrided, or another location where the robotic debridement apparatus is not needed. In an embodiment, the controller can direct the locomotive mechanism to controllably move the at least one robotic debridement apparatus to travel along a selected path. The selected path can be a path of least resistance, a path avoiding collisions with other robotic debridement apparatuses present in the body region, a path having tissue to be debrided, a path having substances to be disposed, a path having portions of the body region requiring a therapeutic effect, or any other selected path. In another example, the controller can direct the debriding tool to debride tissue when the sensors detect undebrided unhealthy tissue, the debris disposal device to capture at least one substance when the sensors detect the at least one substance, etc.

Figure 9:
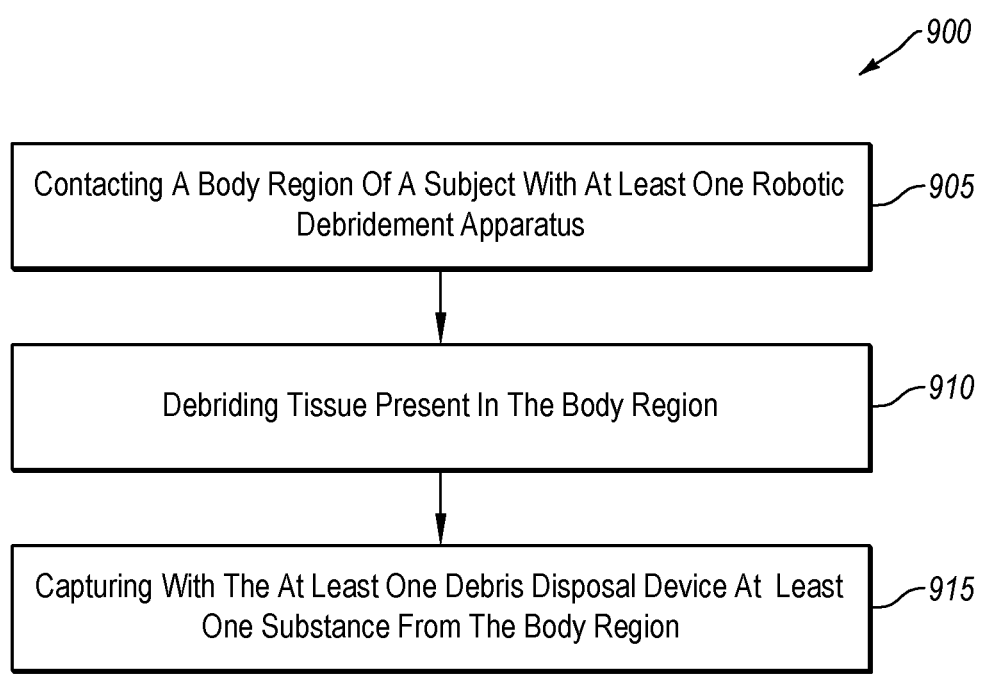

FIG. 9 is a flow diagram of a method 900 of using any of the robotic debridement apparatuses disclosed herein, according to an embodiment. In some embodiments, some of the acts of the method 900 can be split into a plurality of acts, some of the acts can be combined into a single act, and some acts can be omitted. Also, it is understood that additional acts can be added to the method 900. Except as otherwise disclosed herein, the acts of method 900 can be used with any of the robotic debridement apparatuses 100, 200a-g, 300a-o, 400a-j, 500a-b, 600, 700, 1000 (FIGS. 1-7, 10) disclosed herein.

The method 900 includes an act 905 of contacting a body region of a subject with at least one robotic debridement apparatus. For example, the at least one robotic debridement apparatus can include a housing, at least one locomotive mechanism positioned in or on the housing, and at least one debris disposal device in or on the housing. In an embodiment, the at least one robotic debridement apparatus can include at least one debriding tool or at least one therapeutic device. In an embodiment, the at least one robotic debridement apparatus positioned over the body region can include one or more sensors, a controller, a power source, at least one marking device, or at least one extraction device.

In an embodiment, contacting a body region of a subject with at least one robotic debridement apparatus can include manually placing, manually positioning, using at least one extraction device or retrieval device, or another suitable method of contacting the at least one robotic debridement apparatus over the body region. In an embodiment, as will be discussed in more detail later, contacting a body region of a subject with at least one robotic debridement apparatus can include reversibly attaching a dressing (e.g., dressing 1178 of FIGS. 11A-11B) associated with the plurality of robotic debridement apparatuses to the body region.

Act 910 includes debriding tissue (e.g., at least one target tissue) present in the body region. In an embodiment, the tissue is debrided in substantially the same manner as described in act 810 of method 800 (FIG. 8). For example, the at least one robotic debridement apparatus can include at least one debriding tool that debrides tissue from the body region. In an embodiment, the tissue can be debrided by a user (e.g., physician) using, for example, a curette, a scalpel, or another device. In an embodiment, the tissue can be debrided using one or more maggots applied to the body region.

Act 915 includes capturing with the at least one debris disposal device at least one substance from the body region. For example, the debris disposal device can capture debrided tissue that was debrided in act 910. In an embodiment, the debris disposal device can capture the at least one substance from the body region using any of the methods disclosed herein. For example, the debris disposal device can suction the at least one substance from the body region (FIG. 4C). For example, the debris disposal device can adhere or attach thereto the at least one substance from the body region (FIGS. 4A, 4D-4E, 4I-4J). For example, the debris disposal device can absorb or attach thereto the at least one substance from the body region (FIGS. 4A, 4F-4G, 4I-4J). For example, the debris disposal device can dispense one or more pressurized fluids (FIG. 4H) into or onto the body region.

The method 900 can include optional additional acts. For example, method 900 can include at least one of the optional additional acts disclosed in method 900.

L. Systems Including Robotic Debridement Apparatuses

Any of the robotic debridement apparatuses disclosed herein can be used in systems configured to debride tissue (e.g., at least one target tissue) from a body region. For example, the systems disclosed herein can include a plurality of robotic debridement apparatuses. In an embodiment, the systems disclosed herein can include a dressing associated with the robotic debridement apparatuses.

A. Systems Including a Plurality of Robotic Debridement Apparatuses

Figure 10:
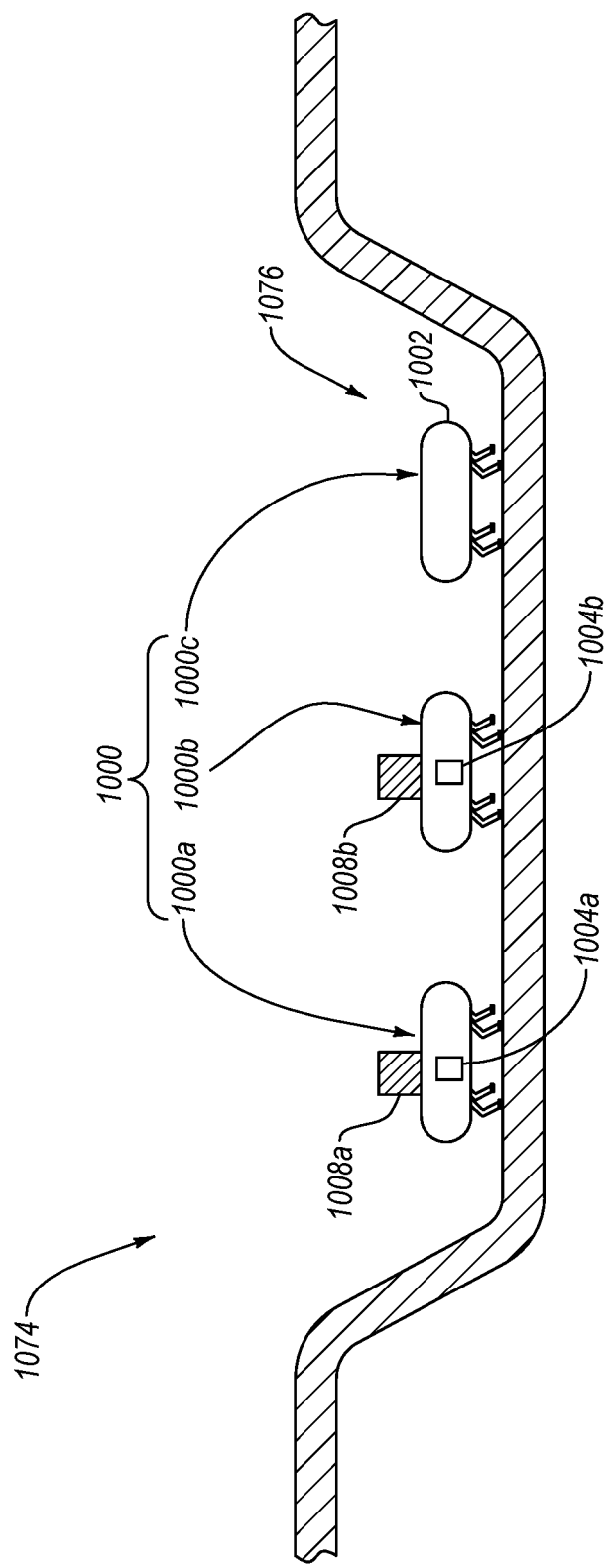
FIG. 10 is a schematic illustration of a system that includes a plurality of robotic debridement apparatuses, according to an embodiment.

FIG. 10 is a schematic illustration of a system 1074 that includes a plurality of robotic debridement apparatuses 1000, according to an embodiment. In the illustrated embodiment, the plurality of robotic debridement apparatuses 1000 include at least one first robotic debridement apparatus 1000a, at least one second robotic debridement apparatus 1000b, and at least one third robotic debridement apparatus 1000c. However, the system 1074 can include only two robotic debridement apparatuses or four or more robotic debridement apparatuses. Except as otherwise described herein, the first, second, and third robotic debridement apparatuses 1000a, 1000b, 1000c shown in FIG. 10 and their materials, components, or elements can be similar to or the same as one or more of the robotic debridement apparatuses 100, 200a-g, 300a-o, 400a-j, 500a-b, 600, 700, (FIGS. 1-7) and their respective materials, components, or elements. For example, the robotic debridement apparatuses 1000 shown in FIG. 10 can include a housing 1002, at least one locomotive mechanism (e.g., first or second locomotive mechanisms 1004a, 1004b), at least one debriding tool (e.g., any of the debriding tools 306a-o of FIGS. 3A-3O), at least one debris disposal device (e.g., any of the debris disposal devices 452a-j of FIGS. 4A-4J), at least one therapeutic device (e.g., any of the therapeutic debridement devices 652a-b of FIGS. 5A-5B), one or more sensors (not shown), a controller (not shown), or a power source (not shown).

In an embodiment, at least two (e.g., all) of the first, second, or third robotic debridement apparatuses 1000a, 1000b, 1000c can be substantially the same. In an embodiment, at least two (e.g., all) of the first, second, or third robotic debridement apparatuses 1000a, 1000b, 1000c can be different from each other. For example, at least one of the first, second, or third robotic debridement apparatuses 1000a, 1000b, 1000c can exhibit a functionality different from that of another at least one of the first, second, or third robotic debridement apparatuses 1000a, 1000b, 1000c. The different functionality can include at least one locomotive mechanism, at least one sensor, at least one controller, at least one different debriding tool; at least one different debris disposal device; at least one different therapeutic device; at least different marking device (e.g., different taggants); at least one different extraction device; at least one of the first, second, or third robotic debridement apparatuses 1000a, 1000b, 1000c having at least one of a debriding tool, a debris disposal device, a therapeutic device, a marking device, or an extraction device and another of the first, second, or third robotic debridement apparatuses 1000a, 1000b, 1000c does not have that respective device; or another suitable different functionality.

In an embodiment, at least one of the first, second, or third robotic debridement apparatuses 1000a, 1000b, 1000c can exhibit a different size or a different geometry than at least one other of the first, second, or third robotic debridement apparatuses 1000a, 1000b, 1000c. The different sizes of the robotic debridement apparatuses can include at least one of the first, second, or third robotic debridement apparatuses 1000a, 1000b, 1000c being larger than another of the first, second, or third robotic debridement apparatuses 1000a, 1000b, 1000c; or at least one of the first, second, or third robotic debridement apparatuses 1000a, 1000b, 1000c being smaller than another of the first, second, or third robotic debridement apparatuses different 1000a, 1000b, 1000c. The different sizes or geometries of the robotic debridement apparatuses can educate the choice of robotic debridement apparatuses having different components (e.g., functionality), for example for use with different sized body regions or different types of body regions, or for different needs or requirements (e.g., different wound debridement needs). The different sizes or geometries of the robotic debridement apparatuses can facilitate the use of robotic debridement apparatuses having different components (e.g., functionality), such as when using multiple robotic debridement apparatuses in or on the same body region. The different sizes or geometries of the robotic debridement apparatuses can also facilitate the use of robotic debridement apparatuses that are configured to debride different portions of a body region 1076 (e.g., a relatively smaller robotic debridement apparatus can facilitate debridement of tissue in a relatively narrow portion of the body region 1076). In an embodiment, the system 1074 can include at least one robotic debridement apparatus of a size and geometry able to be effectively used alone on a body region (e.g., in sequential use). In an embodiment, the system 1074 can include a plurality of robotic debridement apparatuses 1000 of one or more size and one or more geometry able to be effectively used substantially simultaneously on a body region (e.g., about 5 apparatuses, about 10 apparatuses, about 20 apparatuses, about 50 apparatuses, about 100 apparatuses, about 200 apparatuses, about 300 apparatuses, etc.)

In an embodiment, at least one of the first, second, or third robotic debridement apparatuses 1000a, 1000b, 1000c can include one or more first sensors 1008a and another of the first, second or third robotic debridement apparatuses 1000a, 1000b, 1000c can include one or more second sensors 1008b. The first sensors 1008a, and second sensors 1008b can be the same type of sensors. The first and second sensors 1008a, 1008b can be different sensors. For instance, the first sensors 1008a can include a first type of sensor (e.g., chemical sensor, thermal sensor, etc.) and the second sensors 1008b can include a second type of sensor different from the first sensors 1008a. In an embodiment, the first sensor 1008a can include a plurality of sensors and the second sensors 1008b can include a single sensor or a different number of sensors. In an embodiment, the first sensors 1008a can detect one or more first characteristics of the body region 1076, and the second sensor 1008b can detect one or more second characteristics of the body region 1076 that are different than the one or more first characteristics. In an embodiment, at least one of the first, second, or third robotic debridement apparatuses 1000a, 1000b, 1000b can include at least one sensor and another of the first, second or third robotic debridement apparatuses 1000a, 1000b, 1000c does not include a sensor. The first and second sensors 1008a, 1008b can be used, for example, when the robotic debridement apparatuses include a different functionality, when the robotic debridement apparatuses receive information about the body region 1076 from each other or an external source (e.g., the user, a dressing, another robotic debridement apparatus, or the external device 127 of FIG. 1), when the robotic debridement apparatuses facilitate debridement of different tissues, when the robotic debridement apparatuses are working in concert, when the robotic debridement apparatuses facilitate debridement of tissues in different portions of the body region 1076, etc.

In an embodiment, at least one of the first, second, or third robotic debridement apparatuses 1000a, 1000b, 1000c can include at least one first locomotive mechanism 1004a and another of the first, second, or third robotic debridement apparatuses 1000a, 1000b, 1000c can include at least one second locomotive mechanism 1004b. In an embodiment, the first locomotive mechanism 1004a and the second locomotive mechanism 1004b can be substantially the same. In an embodiment, the first locomotive mechanism 1004a and the second locomotive mechanism 1004b can be different. For example, the first and the second locomotive mechanisms 1004a, 1004b can include different types of locomotive mechanisms (e.g., piezoelectric materials, impelling mechanism, inchworm-like motive mechanism, etc.). In an embodiment, the first and second locomotive mechanisms 1004a, 1004b can include at least one similar locomotive mechanism and at least one different locomotive mechanism (e.g., the first locomotive mechanism 1004a includes a piezoelectric material and the second locomotive mechanism 1004b includes a piezoelectric material and an impelling mechanism). In another instance, the first and second locomotive mechanisms 1004a, 1004b can include a similar type of locomotive mechanism that operate differently (e.g., a piezoelectric unimorph and a piezoelectric bimorph).

In an embodiment, at least one of the first, second, or third robotic debridement apparatuses 1000a, 1000b, 1000c can receive power from an external power source (e.g., in the external device 127 of FIG. 1 or in the dressing 2078 of FIG. 20). In an embodiment, at least one of the first, second, or third robotic debridement apparatuses 1000a, 1000b, 1000c can receive one or more sensing signals or one or more operational instructions from the external source (e.g., external device 127 of FIG. 1, a different robotic debridement apparatus, or controller 1112 of the dressing 1178 of FIGS. 11A-11B).

In an embodiment, at least one of the first, second, or third robotic debridement apparatuses 1000a, 1000b, 1000c can include a first component (not shown), and another of the first, second, or third robotic debridement apparatuses 1000a, 1000b, 1000c can include a second component (not shown) that is different from the first component. For example, at least one of the first, second or third robotic debridement apparatuses 1000a, 1000b, 1000c can include a first power source (e.g., battery), and another of the first, second, or third robotic debridement apparatuses 1000a, 1000b, 1000c includes a second power source (e.g., capacitor) that is different than the first power source. In an embodiment, at least one of the first, second, or third robotic debridement apparatuses 1000a, 1000b, 1000c can include a first controller (e.g., having memory), and another of the first, second, or third robotic debridement apparatuses 1000a, 1000b, 1000c can include a second controller (e.g., having a transceiver) that is different than the first controller. In an embodiment, at least one of the first, second, or third robotic debridement apparatuses 1000a, 1000b, 1000c include a first component, and another of the first, second, or third robotic debridement apparatuses 1000a, 1000b, 1000c do not include the first component.

In an embodiment, two or more of the plurality of robotic debridement apparatuses 1000 can be attached together. For example, the attached robotic debridement apparatuses 1000 can be directly coupled (e.g., attached) together, indirectly coupled together (e.g., using a tether), permanently attached together, or temporarily attached together (e.g., reversibly attached together).

In an embodiment, two or more of the plurality of robotic debridement apparatuses 1000 can be configured to transmit information and otherwise communicate with each other. For example, the plurality of robotic debridement apparatuses 1000 can include at least one first robotic debridement apparatus 1000a and at least one second robotic debridement apparatus 1000b. Each of the first and second robotic debridement apparatuses 1000a, 1000b can include a transceiver (e.g., transceiver 124 of FIG. 1) that communicably couples the first and second robotic debridement apparatuses 1000a, 1000b together. For example, the first and second robotic debridement apparatuses 1000a, 1000b can be wiredly or wirelessly coupled together via the transceivers. In an embodiment, the transceivers allow the first robotic debridement apparatus 1000a to transmit information (e.g., information regarding one or more sensing signals, a location of the first robotic debridement apparatus 1000a or another robotic debridement apparatus, a portion of the body region that requires additional work, etc.) to the second robotic debridement apparatus 1000b, or vice versa.

In an embodiment, at least one of the first or second robotic debridement apparatuses 1000a, 1000b includes a controller (e.g., the controller 112 of FIG. 1). For example, when the first robotic debridement apparatus 1000a includes the controller, the controller of the first robotic debridement apparatus 1000a can at least partially control the operation of the first or second robotic debridement apparatuses 1000a, 1000b. For example, when each of the first and second robotic debridement apparatuses 1000a, 1000b includes the controller, the controller of the first robotic debridement apparatus 1000a or the controller of the second robotic debridement apparatus 1000b can at least partially control the operation of the first or second robotic debridement apparatuses 1000a, 1000b. For example, when each of the first and second robotic debridement apparatuses 1000a, 1000b include the controller, the controller of the first robotic debridement apparatus 1000a can at least partially inform the controller of the second robotic debridement apparatuses 1000b of an operation performed by the first robotic debridement apparatus 1000a.

In an embodiment, a first robotic debridement apparatus 1000a includes a controller (e.g., controller 112 of FIG. 1) configured to control the operation of at least one of the second or third robotic debridement apparatuses 1000b, 1000c. For example, the controller of the first robotic debridement apparatus 1000a can function as a commander or master of at least one of the second or third robotic debridement apparatuses 1000b, 1000c, thereby directing a coordinated effort. For instance, the first and second robotic debridement apparatuses 1000a, 1000b can each include at least one debriding tool and the controller controls (e.g., choreographs) the movement of the first and second robotic debridement apparatuses 1000a, 1000b to debride tissue in a body region in a coordinated fashion. For instance, the first robotic debridement apparatus 1000a can include a debriding tool having a blade, the second robotic debridement apparatus 1000b can include a debriding tool having pressurized fluid-dispenser, and the third robotic debridement apparatus 1000c can include at least one debris disposal device. As such, the controller of the first robotic debridement apparatus 1000a can coordinating the movements and functions of the first, second, and third debridement apparatuses 1000a, 1000b, 1000c to debride (e.g., by scraping, cutting, etc.) tissue (e.g., necrotic tissue) of a body region, flush the body region with a debriding or irrigation fluid, and capture debris (e.g., debrided tissue) from the body region.

In an embodiment, the first robotic debridement apparatus 1000a includes a controller and programming configured to control (e.g., in a coordinated manner) at least one of the second or third robotic debridement apparatuses 1000b, 1000c. In an embodiment, the controller of the first robotic debridement apparatus 1000a is programmable. For example, the controller of the first robotic debridement apparatus 1000a can be in communication with an external device (e.g., external device 127 of FIG. 1) having a user interface, and can be programmed through the user interface to control the movements and functions of itself and at least one of the second or third robotic debridement apparatuses 1000b, 1000c.

In an embodiment, the transceiver of at least one of the first, second, or third robotic debridement apparatuses 1000a, 1000b, 1000c is communicably coupled to a device remote and separate from the first, second, or third robotic debridement apparatuses 1000a, 1000b (e.g., external device 127 of FIG. 1, the dressing 1178 of FIGS. 11A-11B). The device can be configured to at least partially control the operation of the first, second, or third robotic debridement apparatuses 1000a, 1000b, 1000c.

In an embodiment, the plurality of robotic debridement apparatuses 1000 (e.g., the first, second, and third robotic debridement apparatuses 1000a, 1000b, 1000c) includes a selected variety of different robotic debridement apparatuses that are each different. The variety of different robotic debridement apparatuses can include, for example, any of the differences disclosed herein. The plurality of robotic debridement apparatuses 1000 can be selected from the variety of different robotic debridement apparatuses based on at least one of the type of tissue to be debrided, the shape and size of the body region 1076, the depth of the body region 1076, the type of dressing used with the body region 1076, the method used to debride tissue (e.g., using surgical tools or robotic debridement apparatuses), etc. For example, the first robotic debridement apparatus 1000a can be selected to preferentially debride a certain type of tissue (e.g., includes sensors configured to detect the certain type of tissue), the second robotic debridement apparatus 1000b can be selected to preferentially capture components of the debrided certain type of tissue, and the third robotic debridement apparatus 1000c can be selected to provide a selected therapeutic effect based on the certain type of tissue. For example, a first combination of robotic debridement apparatuses can be selected for a first debridement session of a body region, and a second, different combination of robotic debridement apparatuses can be chosen for a second debridement session of a body region. For instance, the first selected plurality of robotic debridement apparatuses can each include at least one debriding tool for dispensing one or more hydrogels including collagenase. The second selected plurality of robotic debridement apparatuses can include a combination of at least one first robotic debridement apparatus that includes at least one debriding tool for dispensing an analgesic, at least one second debridement apparatus that includes at least one debriding tool for scraping the dried hydrogel (e.g., a flat blade), and at least one third robotic debridement apparatus that includes at least one debris disposal device for capturing the scraped hydrogel and associated debris.

In an embodiment, the variety of robotic debridement apparatuses can be provided as part of a kit that facilitates debridement of the body region 1076. For example, the kit can include a variety of robotic debridement apparatuses that a user can select (e.g., select only a portion of or all of the variety of robotic debridement apparatuses), a dressing, surgical tools used to debride the tissue, maggots, one or more therapeutic agents to be applied by a user to the body region 1076, or any other device that can facilitate debridement of tissue from the body region 1076.

B. Systems Including a Dressing and a Plurality of Robotic Debridement Apparatuses FIGS. 11A and 11B are schematic cross-sectional side and top plan view illustrations, respectively, of a system 1174 that includes a dressing 1178 that is associated with a plurality of robotic debridement apparatuses 1100, according to an embodiment. The dressing 1178 can be associated with the plurality of robotic debridement apparatuses 1100 in a manner that facilitates debridement of a body region 1176. For example, as discussed in more detail hereafter, the dressing 1178 can facilitate operation of the robotic debridement apparatuses 1100. In an embodiment, the dressing 1178 can directly facilitate debridement of tissue (e.g., at least one target tissue). In an embodiment, the dressing 1178 can include at least one layer 1180. For example, the dressing 1178 can include a single layer. For example, the dressing 1178 can include a first layer and at least one second layer, which can be of the same or different composition as the first layer. For example, the dressing 1178 can include a plurality of layers. In an embodiment, the dressing 1178 at least partially (e.g., completely) encloses (e.g., encircles) the body region 1176 or at least one of the robotic debridement apparatuses 1100. As such, the dressing 1178 can at least partially confine the robotic debridement apparatuses 1100 within the body region 1176. Although FIGS. 11A-11B illustrates and describes the system 1174 as including a plurality of robotic debridement apparatuses 1100 associated with the dressing 1178, it is understood that the system 1174 can include a single robotic debridement apparatus associated with the dressing 1178.

The system 1174 can include the plurality of robotic debridement apparatuses 1100. Except as otherwise described herein, the robotic debridement apparatuses 1100 shown in FIGS. 11A-11B and their materials, components, or elements can be similar to or the same as the robotic debridement apparatus 100, 200a-g, 300a-o, 400a-j, 500a-b, 600, 700, 1000 (FIGS. 1-7, 10) and their respective materials, components, or elements. For example, each of the robotic debridement apparatuses 1100 shown in FIGS. 11-11B can include at least one of a housing, at least one locomotive mechanism, at least one debriding tool, at least one debris disposal device, at least one therapeutic device, one or more sensors, a controller, or a power source (not shown).

C. Components of the Dressing

The dressing 1178 can include one or more components positioned therein or thereon that facilitate functioning of the dressing 1178. The one or more components positioned in or on the dressing 1178 can be used in any of the dressings embodiments disclosed herein.

Referring to FIG. 11A, the dressing 1178 can include one or more sensors 1108 positioned in or on the dressing 1178. For example, the sensors 1108 can be positioned on an outer surface 1182 of the dressing 1178, can extend from the outer surface 1182 into the body region 1176, can be positioned on another surface of the dressing 1178, or can be positioned inside the dressing 1178 itself. The sensors 1108 can be configured to detect one or more characteristics of the body region 1176, the dressing 1178, or at least one of the robotic debridement apparatuses 1100.

In an embodiment, the sensors 1108 can be the same as or similar to the sensors 108 (FIG. 1). In an embodiment, the sensors 1108 can include sensors that are different from the sensors 108 (FIG. 1). For example, the sensors 1108 can include at least one chemical sensor, at least one thermal sensor, at least one moisture sensor, at least one electrical conductivity sensor, at least one optical sensor, at least one acoustic sensor, at least one electrical power sensor, or another sensor disclosed herein. For example, the sensors 1108 can be configured to detect tissue viability, tissue type, the presence of a microbe, components of wound exudate, moisture content of the body region 1176, temperature of the body region 1176, or another characteristic of the body region 1176. For example, the sensors 1108 can be configured to detect one or more agents released into or onto the body region 1176, the presence of the robotic debridement apparatuses 1100 (e.g., using unique identifier tags such as RFID tags), one or more characteristics of the dressing 1178 (e.g., moisture content, presence of a microbe, or an aspect of an electronic component such as a power level), etc.

The sensors 1108 can transmit one or more sensing signals. For example, the sensors 1108 can transmit one or more sensing signals responsive to detecting the one or more characteristics of the body region 1176, the dressing 1178, or at least one of the robotic debridement apparatuses 1100. The sensing signals can include data having information regarding the detected characteristics encoded therein. The sensors 1108 can transmit the sensing signals to one or more components of the system 1174 (e.g., one or more components of the dressing 1178, one or more components of at least one of the robotic debridement apparatuses 1100, or the external device 127 of FIG. 1). The sensors 1108 can be sense the characteristics or transmit the sensing signals responsive to direction from a controller 1112, controller 1112' (e.g., controller 112 of FIG. 1) coupled to at least one of the robotic debridement apparatuses 1100, or to one or more external devices (e.g., external device 127 of FIG. 1).

In an embodiment, the dressing 1178 includes a controller 1112 that is positioned in or on the dressing 1178. The controller 1112 can be the same as or similar to the controller 112 (FIG. 1). For example, the controller 1112 can include memory 1122, a transceiver 1124 (e.g., receiver or transmitter), or a processor 1126.

In an embodiment, the controller 1112 can be communicatively coupled (e.g., wiredly or wirelessly) to one or more components of the system 1174, such as one or more components of the dressing 1178 or one or more components of the robotic debridement apparatuses 1100. For example, the dressing 1178 can be communicably coupled to at least one of the robotic debridement apparatuses 1100 (e.g., the controller 1112 can transmit operational signals or informational signals to at least one of the robotic debridement apparatuses 1100). The controller 1112 can be configured to control at least one of the one or more components of the system 1174 that are communicably coupled to the controller 1112. For instance, the controller 1112 can control the operation of at least one of the robotic debridement apparatuses 1100 (e.g., instead of or in conjunction with the controller 1112'), the sensors 1108, etc. In an embodiment, the controller 1112 controls the operation of the one or more components of the system 1174 responsive to receiving the sensing signals transmitted from the sensors 1108 or sensors coupled to at least one of the robotic debridement apparatus (e.g., sensors 108 of FIG. 1). In an embodiment, the controller 1112' can at least partially control the operation of the dressing 1178 (e.g., the controller 1112).

In an embodiment, the system 1174 can include an external device (e.g., external device 127 of FIG. 1) that is communicably coupled (e.g., wiredly or wirelessly) to one or more components of the system 1174. For example, the controller 1112 can transmit or receive information (e.g., one or more command signals, one or more user directed commands, one or more programs, one or more sensing signals, one or more operational instructions, etc.) to or from the external device. In an embodiment, the external device can at least partially control the operation of the dressing 1178 or another component of the system 1174 (e.g., allow a user to remotely control, at least partially control the operation of at least one component of the system 1174 or program the controller 1112). In an embodiment, the controller 1112 can be incorporated with one or more devices remote from the dressing 1178.

The dressing 1178 can include a dressing power source 1110. The dressing power source 1110 can be is positioned in or on the dressing 1178 or external the dressing 1178. The dressing power source 1110 can be the same as or similar to the power source 110 (FIG. 1). For example, the dressing power source 1110 can include at least one battery or at least one capacitor. Additionally, the dressing power source 1110 can be electrically coupled to one or more components of the system 1174. For example, the dressing power source 1110 can be coupled to the sensors 1108, the controller 1112, or at least one of the robotic debridement apparatuses 1100. In an embodiment, the dressing power source 1110 can include any of the power-generating devices disclosed herein. In an embodiment, the dressing power source 1110 can be coupled to and configured to provide electrical power to at least one of the robotic debridement apparatuses 1100. For example, at least one of the robotic debridement apparatuses 1100 can be wiredly coupled or wireless coupled (e.g., via the magnetic field-generating device 2199 of FIG. 21). In an embodiment, the dressing power source 1110 can be coupled to a device (e.g., socket, battery) external to the dressing 1178 and configured to receive electrical power from the device. In an embodiment, the power source 1110 is omitted and the dressing 1178 receives electrical power (if needed) from a device external therefrom (e.g., the socket, the battery).

In an embodiment the dressing 1178 includes at least one electronic component that is a flexible electronic component or conformable electronic component. For example, the dressing 1178 can include one or more of serpentine circuitry, flexible circuitry, or electronic threads. In an embodiment, at least one component of the dressing 1178 can be manufactured using an additive manufacturing process.

D. Composition of the Dressing

In an embodiment, at least a portion of the dressing 1178 (e.g., the at least one layer 1180) is formed from a material that is at least semi-permeable (e.g., permeable) to a gas. As such, the dressing 1178 can permit a gas (e.g., air) from a region external to the dressing 1178 to flow therethrough into the body region 1176. Permitting a gas to flow through the dressing 1178 can improve the healing process of the body region due to the increased demand for oxygen during the healing process (e.g., cell proliferation, bacterial defense, angiogenesis, collagen synthesis, etc.). In an embodiment, at least a portion of the dressing 1178 can be substantially impermeable to gas. Such as dressing 1178 can maintain moist conditions within the body region 1176, which can facilitate fibrinolysis and angiogenesis. In an embodiment, at least a portion of the dressing 1178 can be formed from chiffon, rayon, nylon, gauze, hydrocolloid, hydrogel, alginate, collagen, hydrofiber dressing, polyvinyl film, polyurethane (e.g., Tegaderm), or another suitable material.

In an embodiment, the dressing 1178 includes a first layer and at least one second layer that is different from the first layer in composition or function. For example, the dressing 1178 can include a bandage having several layers of the same material. For example, the dressing 1178 can include a primary bandage (e.g., interfacing with a wound) and a secondary bandage (e.g., a polyurethane film bandage that adheres to skin adjacent the wound and holds the primary bandage in place). For example, the dressing 1178 can include a multi-layer dressing such as a composite dressing. The composite dressing can include a contact layer comprising a non-adherent material (e.g., rayon, nylon, or polyethylene), a middle layer comprising a material (e.g., hydrogel, semi-permeable foam, hydrocolloid, or alginate) able to absorb moisture and wick it away from a wound bed yet maintain a moist environment, and an outer layer comprising a semi-permeable film that serves as a protective barrier.

In an embodiment, the dressing 1178 can include an interfacial surface 1184 that is configured to contact and attach to the body region 1176 (e.g., a skin surface of the wound). For example, the interfacial surface 1184 can exhibit a shape that substantially conforms to a surface of the body region 1176, is malleable, is pliable, or is deformable. In an embodiment, the interfacial surface 1184 is configured to be reversibly attached to the body region 1176 or to a body part (e.g., a limb, or a torso) that includes the body region 1176. For example, at least a portion of the interfacial surface 1184 can include an adhesive or other attachment mechanism thereon. The adhesive or other attachment mechanism can be attached to the body region 1176 such that removing the dressing 1178 from the body region 1176 does not significantly damage healthy tissue. For example, at least a portion of the adhesive can attach to tissue adjacent a wound in the body region. For example, the dressing 1178 can be attached by wrapping the dressing 1178 around a body part (e.g., a leg, a foot, an ankle, an arm, a hand, a wrist, a torso, a head, etc.).

In an embodiment, the dressing 1178 can include a biodegradable material. In such an embodiment, the interfacial surface 1184 can include an adhesive or other attachment mechanism that is configure to reversibly or non-reversibly attach (e.g., substantially permanently attach) to the body region 1176. In an embodiment, the dressing 1178 can include at least one layer 1180 that defines the interfacial surface 1184. For example, the at least one layer 1180 can include a hydrocolloid layer, a hydrogel layer, hydrofiber dressing, etc. In an embodiment, the dressing 1178 can include an adhesive between the at least one layer 1180 and the body region.

The compositions and materials with regards to the dressing 1178 can be used in any of the dressing embodiments disclosed herein.

In an embodiment, the dressing 1178 comprises a sterile material. In an embodiment, the dressing 1178 or a component therein or thereon is sterilizable.

In an embodiment, the dressing 1178 includes at least one shape or at least one size that is appropriate to fit (e.g., at least partially cover) the body region 1176 or to facilitate functioning of one or more robotic debridement apparatuses 1100. In an embodiment, the dressing 1178 includes a first layer having a first shape and at least one second layer having at least one second shape that differs from the first shape. In an embodiment, the dressing 1178 includes a first layer having a first size and at least one second layer having at least one second size that differs from the first size. For example, the dressing 1178 can include at least one layer that is a rectangle, a triangle, a circle, or a ring. For example, the dressing 1178 can include as a first layer (e.g., a primary dressing) that is a small circle and a second layer (e.g., a cover layer) that is a rectangular film that holds the circle in place.

E. Types of Dressings

The dressings disclosed herein can include different types of dressings. In an embodiment, the dressings disclosed herein can include a confinement dressing that is configured to confine the plurality of robotic debridement apparatuses within the body region. The confinement dressing can be configured to have the robotic debridement apparatuses directly positioned in the body region. In an embodiment, the dressings disclosed herein can include a containment dressing that is configured to contain the robotic debridement apparatuses therein. As such, a containment dressing is configured to have the robotic debridement apparatuses indirectly positioned in the body region.

Referring to FIG. 11B, the dressing 1178 is an example of a confinement dressing. The dressing 1178 includes a ring dressing that at least partially (e.g., completely) extends laterally about (e.g., encircles) the body region 1176. For example, the at least one layer 1180 of the dressing 1178 can be reversibly attached or otherwise attached to a skin surface that extends laterally about or forms part of a wound on the body region 1176 (e.g., so that the dressing 1178 encircles the wound). The at least one layer 1180 can also extend generally upwardly from the skin surface for a selected distance.

In an embodiment, the dressing 1178 can be configured to prevent at least one of the robotic debridement apparatuses 1100 from leaving the body region 1176. For example, the at least one layer 1180 of the dressing 1178 can include a material, shape, color, design, or other feature that can be detected by sensors 1108' (e.g., sensors 108 of FIG. 1) coupled to at least one robotic debridement apparatus 1100. The at least one robotic debridement apparatus 1100 can include operational instructions that prevent the at least one robotic debridement apparatus 1100 from crossing the dressing 1178 after the dressing 1178 is detected.

In an embodiment, the at least one layer 1180 of the dressing 1178 can include a material that exhibits a low coefficient of friction against a portion of the at least one robotic debridement apparatus 1100 that contacts the at least one layer 1180. The low coefficient of friction can prevent the at least one robotic debridement apparatus 1100 from crossing or climbing on the at least one layer 1180 of the dressing 1178.

In an embodiment, the selected distance that the at least one layer 1180 of the dressing 1178 extends above the skin surface can be sufficient to prevent the at least one robotic debridement apparatus 1100 from crossing the at least one layer 1180. For instance, the selected distance can be at least 20% (e.g., at least 50%, at least 100%) of the total height of the at least one robotic debridement apparatus 1100, the maximum height the locomotive mechanism 1104 vertically moves the at least one robotic debridement apparatus 1100, or the vertical height of an impelling mechanism (e.g., impelling mechanism 105, 205c, 205d, 205f of FIGS. 1, 2C, 2D, 2F).

In the illustrated embodiment, the dressing 1178 forms an open air system 1174 since the dressing 1178 is a ring dressing. In other words, the dressing 1178 does not completely cover the body region 1176 or the robotic debridement apparatuses 1100. For example, the at least one layer 1180 defines at least one opening 1186. As such, the body region 1176 is exposed to air (e.g., oxygen) regardless of the materials that are used to form the dressing 1178. Additionally, the at least one opening 1186 can enable a user to position or remove at least one robotic debridement apparatus 1100 in or from the body region 1176 after the dressing 1178 is attached to the body region 1176. In an embodiment, the dressing 1178 can include at least one additional layer (not shown) that covers the opening 1186 (e.g., a flap). The at least one additional layer can protect the body region 1176, be reversibly attached to the at least one layer 1180, be at least semi-permeable to gas, or at least partially transparent.

FIG. 12 is a schematic view of a system 1274 that includes a dressing 1278 and at least one robotic debridement apparatus 1200 (e.g., a plurality of robotic debridement apparatuses 1200) positioned in a body region 1276, according to an embodiment. The dressing 1278 is another example of a confinement dressing 1278. The dressing 1278 includes at least one layer 1280 that at least partially (e.g., completely) encloses or covers the body region 1276 or the robotic debridement apparatuses 1200. For example, the at least one layer 1280 can exhibit a generally sheet-like or generally planar shape that exhibits a size and shape that covers at least a portion of the body region 1276. The at least one layer 1280 can also include an interfacial surface 1284 that attaches to a portion of the body region 1276 (e.g., attaches to a skin surface that extends about a wound in the body region). The dressing 1278 can define at least one aperture (not shown).

In the illustrated embodiment, the system 1274 includes the at least one robotic debridement apparatus 1200 positioned directly into the body region 1276. As such, the robotic debridement apparatus 1200 is positioned between the dressing 1278 (e.g., the at least one layer 1280) and the body region 1276.

In an embodiment, the system 1274 be configured such that the dressing 1278 (e.g., the at least one layer 1280) is positioned between the robotic debridement apparatus 1200 and the body region 1276. In an embodiment the dressing 1278 can be configured to enable the robotic debridement apparatus 1200 positioned above the dressing 1278 to be in fluid communication with the body region 1276. For example, the dressing 1278 can define at least one aperture (e.g., aperture 1387 of FIG. 13) having sufficient size to allow the robotic debridement apparatus 1200 positioned above the dressing 1278 to have access to the body region 1276, while preventing the robotic debridement apparatus 1200 from passing therethrough.

FIG. 13 is a schematic view of a system 1374 that includes a dressing 1378 and at least one robotic debridement apparatus 1300 (e.g., a plurality of robotic debridement apparatuses 1300) positioned in a body region 1376, according to an embodiment. The dressing 1378 is an example of a containment dressing. In particular, the dressing 1378 includes the robotic debridement apparatus 1300 positioned therein. For example, the dressing 1378 can define at least one containment region 1388 that includes the robotic debridement apparatus 1300 therein. The containment region 1388 can be substantially enclosed by the dressing 1378 or merely partially enclosed by the dressing 1378 (e.g., permitting the robotic debridement apparatuses 1300 to be removed therefrom or added thereto).

In the illustrated embodiment, the dressing 1378 includes a first layer 1380 and a second layer 1390 positioned above the first layer 1380. The first layer 1380 and the second layer 1390 can be distinct layers attached together or can be integrally formed together. In an embodiment, at least one of the first or second layers 1380, 1390 can exhibit a generally sheet-like or generally planar shape that substantially covers the body region 1376 and is attached to the body region 1376 (e.g., attached to a skin surface that extends about a wound of the body region 1376). In an embodiment, the first and second layers 1380, 1390 do not cover the body region 1376. In such an embodiment, the first or second layers 1380, 1390 can be attached to another layer (not shown) that substantially covers the body region 1376 (e.g., wrapping around a body part that includes the body region 1376), or the first and second layers 1380, 1390 can be attached to a portion of the body region 1376.

The first and second layers 1380, 1390 can be formed (e.g., attached) together in any manner that forms the containment region 1388 therebetween. For example, the first and second layers 1380, 1390 can be attached around a periphery thereof using at least one of an adhesive, a thread, etc. In an embodiment, at least one of the first layer 1380, the second layer 1390, or an interface therebetween can define a passageway (not shown) that allows the at least one robotic debridement apparatus 1300 positioned in the containment region 1388 to pass therethrough. For example, the passageway can include a slit formed within the first or second layers 1380, 1390, a reversible closure between the first and second layers 1380, 1390, or another suitable passageway. As such, the passageway can allow the robotic debridement apparatus 1300 to be removed from or added to the containment region 1388. In an embodiment, the first and second layers 1380, 1390 completely enclosed the containment region 1388.

In an embodiment, the first layer 1380 can include a plurality of apertures 1386 formed therein that permit the robotic debridement apparatus 1300 to be in fluid communication with the body region 1376. For example, at least one of the apertures 1386 can exhibit a size and geometry that permits fluid, debrided tissue, at least one substance, or other tissue to enter the containment region 1388. In an embodiment, at least one of the apertures 1386 can exhibit a size and geometry that permits a portion of the robotic debridement apparatus 1300 to extend therethrough. In an embodiment, at least one of the apertures 1386 can exhibit a size that permits a fluid-dispensed by the robotic debridement apparatus 1300 to pass therethrough. In an embodiment, each of the plurality of apertures 1386 can exhibit a size and geometry that prevents the at least one robotic debridement apparatuses 1300 present in the containment region 1388 from passing therethrough.

In an embodiment, the at least one robotic debridement apparatus 1300 can be positioned within one or more layers of the dressing 1378 instead of in the containment region 1388. For example, the robotic debridement apparatus 1300 can be positioned within the first layer 1380 or the second layer 1390. In an embodiment, the containment region 1388 may be omitted.

In an embodiment, the dressing 1378 can be configured as both a containment dressing and a confinement dressing. For example, the system 1374 can include at least one robotic debridement apparatus 1300 positioned in the body region 1376 (e.g., directly positioned in the body region 1376) and at least one of the robotic debridement apparatuses 1300 can be positioned in the containment region 1388.

F. Association of the Dressing with the Plurality of Robotic Debridement Apparatuses As previously discussed, any of the dressings disclosed herein can be configured to be associated with at least one of a plurality of robotic debridement apparatuses positioned in the body region. FIGS. 11A-11B, and 14-22 are schematic illustrations of different systems that include a dressing having different associations with a plurality of robotic debridement apparatuses, according to different embodiments. The dressings illustrated in FIGS. 11A-11B, and 14-22 are associated with at least one of the plurality of robotic debridement apparatuses when the dressing is coupled (e.g., directly attached, indirectly attached, reversibly attached, permanently attached, electrically coupled, etc.) to at least one of the robotic debridement apparatuses, facilitates operation of at least one of the robotic debridement apparatuses, or directly facilitates debridement of tissue from the body region along with the robotic debridement apparatuses. Although FIGS. 11A-11B, and 14-22 illustrate and describe systems that include a plurality of robotic debridement apparatuses associated with the dressing, it is understood that the systems can include a single robotic debridement apparatus associated with the dressing.

Except as otherwise described herein, the dressings shown in FIGS. 11A-11B and 14-22 and their materials, components, or elements can be similar to or the same as the dressings 1178, 1278, 1378 (FIGS. 11A-13) and their respective materials, components, or elements. For example, the dressings illustrated in 11A-11B, and 14-22 can be configured as a confinement dressing (e.g., dressing 1178, 1278 of FIGS. 11A-12) or as a containment dressing (e.g., dressing 1378 of FIG. 13). Any of the associations between the dressings and the plurality of robotic debridement apparatuses disclosed in FIGS. 11A-11B and 14-22 can be used in any of the dressing embodiments disclosed herein.

Additionally, except as otherwise described herein, the plurality of robotic debridement apparatuses shown in FIGS. 11A-11B and 14-22 and their materials, components, or elements can be similar to or the same as the robotic debridement apparatuses 100, 200a-g, 300a-o, 400a-j, 500a-b, 600, 700, 1000 (FIGS. 1-7, 10) and their respective materials, components, or elements. For example, the robotic debridement apparatuses shown in FIGS. 11A-11B and 14-22 can include at least some of a housing, at least one locomotive mechanism, at least one debriding tool, at least one debris disposal device, at least one therapeutic device, one or more sensors, a controller, or a power source.

Referring to FIG. 11A, as previously discussed, the dressing 1178 can include one or more sensors 1108 positioned in or on the dressing 1178. The sensors 1108 can be configured to detect one or more characteristics of the body region 1176. The sensors 1108 can be configured to transmit one or more sensing signals to one or more components of the system 1174. For example, the sensors 1108 can transmit the sensing signals to at least one robotic debridement apparatus 1100 that does not include sensors coupled thereto or does not include sensors configured to detect at least one characteristic encoded in the sensing signals. In an embodiment, the robotic debridement apparatuses 1100 that receive the sensing signals can operate responsive to receiving the sensing signals. For example, the robotic debridement apparatuses 1100 that receive the sensing signals can include a controller 1112' that directs at least one locomotive mechanism 1104 (e.g., locomotive mechanism 104 of FIG. 1) to move its respective robotic debridement apparatuses 1100 to a location of the body region 1176 having un-debrided tissue or away from a location having healthy tissue. The robotic debridement apparatuses 1100 that receives the sensing signals can receive the sensing signals using a transceiver 1124' (e.g., transceiver 124 of FIG. 1). The sensors 1108 can transmit the sensing signals using, for example, a transceiver 1191 positioned therein or thereon or the transceiver 1124.

As previously discussed, the dressing 1178 can include a controller 1112 positioned therein or thereon. The controller 1112 can include control electrical circuitry (e.g., memory 1122, transceiver 1124, or processor 1126) that is configured to control the operation of one or more components of the system 1174 (e.g., one or more components of at least one of the robotic debridement apparatuses 1100). For example, the controller 1112 can transmit (e.g., wirelessly or wiredly) one or more operational instructions therefrom to at least one of the robotic debridement apparatuses 1100 using the transceiver 1124. The at least one robotic debridement apparatus 1100 that receives the operational instructions from the controller 1112 can at least one of move, debride tissue, dispose of substances in the body region 1176, provide a therapeutic effect to the body region 1176, or otherwise operate responsive to the operational instructions. In an embodiment, the controller 1112 can receive (at the transceiver 1124) one or more operational instructions from at least one of the robotic debridement apparatuses 1100 (e.g., from controller 1112'). The operational instructions received from the at least one of the robotic debridement apparatuses 1100 can at least partially control the operation of the dressing 1178 or can be at least partially transmitted by the transceiver 1124 to another of the robotic debridement apparatuses 1100 to at least partially control the operation of the another of the robotic debridement apparatuses 1100.

Referring to FIG. 14, an embodiment of a system 1474 includes a dressing 1478 that is associated with a plurality of robotic debridement apparatuses 1400 in which the dressing 1478 is configured to dispense one or more fluids, one or more gels, or one or more hydrogels into a body region 1476. In the illustrated embodiment, the dressing 1478 includes one or more regions 1492 with the fluids, gels, or hydrogels (collectively illustrated with the reference number 1433) therein. The regions 1492 can be positioned in or on the dressing 1478.

The regions 1492 can be configured to passively provide the fluids, gels, or hydrogels 1433 to the body region 1476. For example, the regions 1492 can include an absorbent material (e.g., absorbent material 458 of FIGS. 4G-4H), at least one reservoir (e.g., reservoir 335i, 335j, 441, 535 of FIG. 3I, 3J, 4H, or 5) that is or is not fluidly coupled to a dispense element, or another device configured to passively dispense the fluids, gels, or hydrogels 1433. A device passively provides the fluids, gels, or hydrogels 1433 when the device does not include electronic or mechanical devices coupled thereto that is configured to dispense the fluids into or onto the body region 1476. For example, the regions 1492 can use gravity, capillary action, or pressure from the dressing 1478 pressing against the body region 1476 to dispense the fluids, gels, or hydrogels 1433 into or onto the body region 1476.

In an embodiment, the regions 1492 can be configured to store any of the fluids, gels, or hydrogels 1433 disclosed herein. For example, the regions 1492 can be configured to store one or more biocompatible fluids, one or more debriding agents, one or more degrading agents, one or more therapeutic agents, or another fluid-disclosed herein. In an embodiment, the regions 1492 can store the fluids in a sterile environment. In an embodiment, the regions 1492 can accept fluids from a user after the dressing 1478 is positioned over the body region 1476. For example, regions 1492 can an inlet (not shown) that can receive one or more fluids from a user.

Referring to FIG. 15, an embodiment of a system 1574 includes a dressing 1578 that is associated with a plurality of robotic debridement apparatuses 1500 in which the dressing 1578 is configured to dispense one or more fluids, one or more gels, or one or more hydrogels at a body region 1576. In the illustrated embodiment, the dressing 1578 includes one or more devices that are configured to actively dispense the fluids, gels, or hydrogels (collectively illustrated with the reference number 1533) into the body region 1576. The fluids, gels, or hydrogels 1533 can include the same fluids, gels, or hydrogels 1533 dispensed from the plurality of regions 1492 (FIG. 14).

In the illustrated embodiment, the dressing 1578 includes at least one fluid reservoir 1535 positioned in or on the dressing 1578. The fluid reservoir 1535 can be the same as or substantially similar to any of the reservoirs or regions disclosed herein. The fluid reservoir 1535 can be fluidly coupled to at least one fluid-dispense element 1536 positioned in or on the dressing 1578. The fluid-dispense element 1536 can be the same as or substantially similar to any of the dispense elements disclosed herein. The fluid-dispense element 1536 can include at least one fluid-dispense aperture 1540 that is configured to dispense the fluids, gels, or hydrogels 1533 into or onto the body region 1576. The at least one fluid-dispense aperture 1540 can form part of a sprayer, a slit nozzle, etc. The dressing 1578 can include one or more actuators 1550 positioned therein or thereon. The actuators 1550 can be operably coupled to at least one of the fluid reservoir 1535 or the fluid-dispense element 1536. For example, the actuators 1550 can be distinct from or integrally formed with the fluid reservoir 1535 or the fluid-dispense element 1536. During operation, the actuators 1550 can apply a pressure to or otherwise actuate the fluid reservoir 1535 or the fluid-dispense element 1536, thereby causing the fluids, gels, or hydrogels 1533 to be dispensed into or onto the body region 1576. The actuators 1550 can include a piezoelectric material, a clamp, a pump, a compressor, or another actuator disclosed herein. In an embodiment, the actuators 1550 can move the fluid-dispense element 1536 relative to the dressing 1578 such that the fluid-dispense element 1536 controllably dispenses the fluids, gels, or hydrogels 1533 towards different selected portions of the body region 1576.

In an embodiment, the dressing 1578 can include a controller 1512 positioned therein or thereon. The controller 1512 can be communicably coupled to the actuators 1550, the fluid reservoir 1535, or the fluid-dispense element 1536. The controller 1512 can direct the actuators 1550, the fluid reservoir 1535, or the fluid-dispense element 1536 to controllably dispense the fluids, gels, or hydrogels 1533 into or onto the body region 1576. In another example, at least one of the robotic debridement apparatuses 1500 can include a controller 1512' and the controller 1512' can direct the actuators 1550, the fluid reservoir 1535, or the fluid-dispense element 1536 to controllably dispense the fluids, gels, or hydrogels 1533 into or onto the body region 1576.

Figure 16:
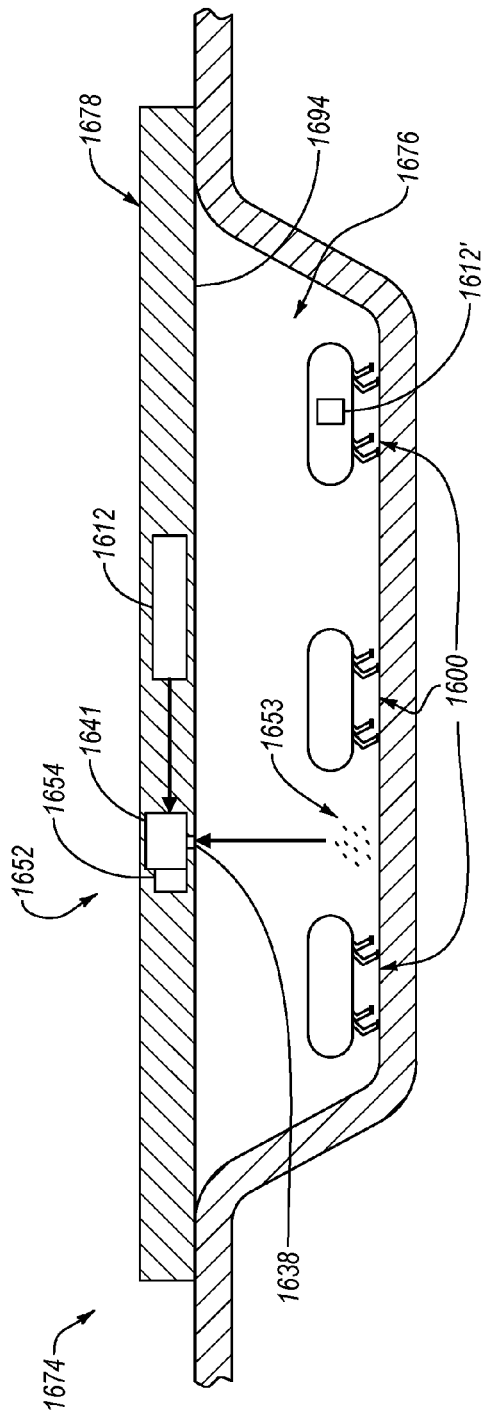

Referring to FIG. 16, an embodiment of a system 1674 includes a dressing 1678 that is associated with a plurality of robotic debridement apparatuses 1600 in which the dressing 1678 includes at least one dressing disposal device 1652 positioned therein or thereon. The dressing debris disposal device 1652 is configured to capture (e.g., remove or sequester) at least one substance 1653 (e.g., debrided tissue, foreign matter, or fluids) from the body region 1676. In the illustrated embodiment, the dressing debris disposal device 1652 includes at least one suction device 1654 that is positioned in or on the dressing 1678. In an embodiment, the suction device 1654 can be the same as or substantially similar to the suction device 454 (FIG. 4C). In an embodiment, the suction device 1654 can be different (e.g., larger) that the suction device 454. The suction device 1654 can be fluidly coupled to the body region 1676, for example, via a conduit 1638. In an embodiment, the conduit 1638 can extend from a bottommost surface 1694 of the dressing 1678 into the body region 1676. The suction device 1654 can be fluidly coupled to at least one debris reservoir 1641 positioned in or on the dressing 1678. The debris reservoir 1641 can be configured to store the at least one substance 1653 that is removed from the body region 1676 using the suction device 1654. The debris reservoir 1641 can include, for example, a chamber, a chamber having a negative pressure relative to the body region 1676, or an absorbent material. In an embodiment, the dressing 1678 can include one or more actuators (not shown) configured to move the conduit 1638 relative to the dressing 1678 such that the conduit 1638 removes at least one substance 1653 from different selected portions of the body region 1676.

In an embodiment, the dressing 1678 includes a controller 1612 positioned therein or thereon. The controller 1612 can be communicably coupled to at least one of the suction device 1654 or the debris reservoir 1641. The controller 1612 can direct the suction device 1654 or the debris reservoir 1641 to controllably remove at least one substance 1653 from the body region. In an embodiment, at least one of the plurality of robotic debridement apparatuses 1600 can include a controller 1612' that is communicably coupled to and configured to direct the operation of the suction device 1654 or the debris reservoir 1641.

Figure 17:
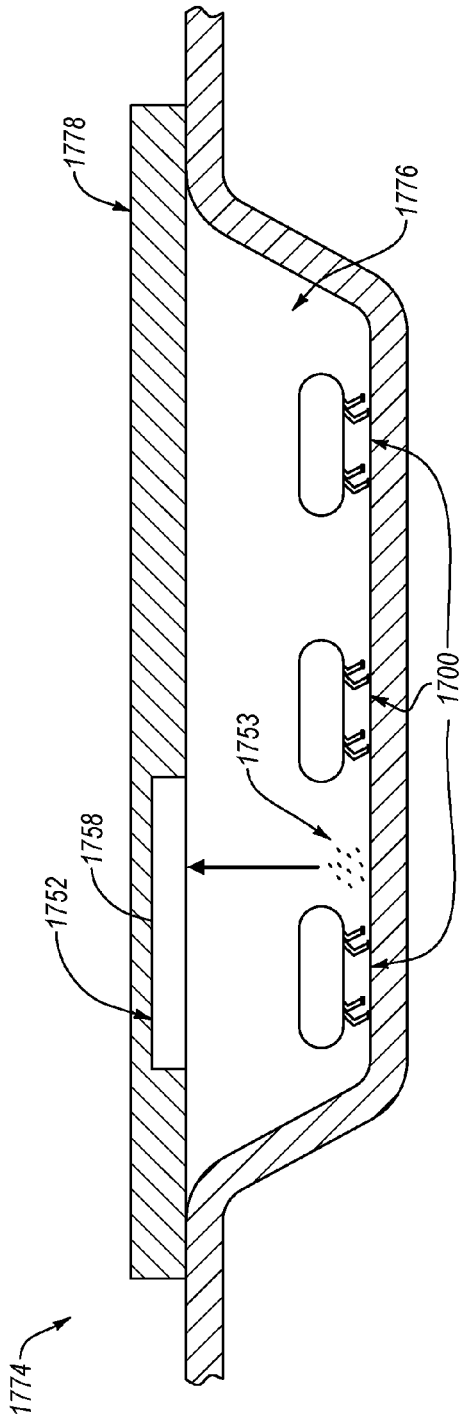

Referring to FIG. 17, an embodiment of a system 1774 includes a dressing 1778 associated with a plurality of robotic debridement apparatuses 1700 in which the dressing 1778 includes at least one dressing debris disposal device 1752 positioned therein or thereon. For example, the dressing debris disposal device 1752 is configured to capture (e.g., remove, absorb, or attach thereto) at least one substance 1753 from a body region 1776. In the illustrated embodiment, the dressing debris disposal device 1752 includes an absorbent material 1758 positioned therein or thereon. The absorbent material 1758 can be the same as or similar to the absorbent material 458 (FIG. 4F-4G). For example, the absorbent material 1758 can include a porous material, a wicking material, a woven material, or any other suitable material. In an embodiment, the dressing 1778 can include a suction device (e.g., suction device 1654 of FIG. 16) coupled to the absorbent material 1758 that is configured to increase a rate and an amount of the at least one substance 1753 removed, absorbed, or attached to the absorbent material 1758. In an embodiment, the absorbent material 1758 can be replaced or used in conjunction with an adhesive material (e.g., adhesive material 456 of FIG. 4D-4E). In an embodiment, substantially the entire dressing 1778 can be formed from the absorbent material 1758. In an embodiment at least one layer (e.g., 1080, 1180, or 1280) of the dressing 1778 can be formed from the absorbent material 1758 or the adhesive material.

Referring to FIG. 18, an embodiment of a system 1874 includes a dressing 1878 associated with a plurality of robotic debridement apparatuses 1800 in which the dressing 1878 is configured to disinfect, sterilize, facilitate healing, or otherwise provide a therapeutic effect to at least a portion of the body region 1876. For example, the dressing 1878 can be configured to disinfect or sterilize unhealthy tissue, healthy tissue, damaged tissue (e.g., damaged during the debriding process), tissue uncovered after tissue was debrided, or at least one robotic debridement apparatus 1800 present in the body region 1876, etc.

In an embodiment, the dressing 1878 can include at least one energy-emitting device 1864 positioned in or on the dressing 1878. The energy-emitting device 1864 can be substantially similar to the energy-emitting device 564 (FIG. 5B). For example, the energy-emitting device 1864 can emit an energy 1833 towards at least a portion of the body region thereby disinfecting, sterilizing, facilitate healing, or otherwise providing a therapeutic effect to a portion of the body region 1876. For example, the energy 1833 can include light, acoustic energy, electric energy, or thermal energy.

In an embodiment, at least one of the energy-emitting device 1864 is coupled to one or more actuators (not shown) that are positioned in or on the dressing 1878. The actuators can be configured to controllably move (e.g., change the direction the energy-emitting device 1864 emits the energy 1833, move the energy-emitting device 1864 relative to the dressing 1878, etc.) the energy-emitting device 1864 such that at least one of the energy-emitting device 1864 controllably disinfects, sterilizes, facilitates healing or otherwise provides a therapeutic effect to different selected portions of the body region 1876. In an embodiment, the energy-emitting device 1864 or the actuators operate responsive to directions from a controller (e.g., controller 112 of FIG. 1, controller 1112 of FIG. 11A).

Referring to FIG. 19, an embodiment of a system 1974 includes a dressing 1978 associated with a plurality of robotic debridement apparatuses 1900 in which the dressing 1978 is configured to provide electrical power to at least one of the robotic debridement apparatuses 1900. For example, as previously discussed, the dressing 1978 can include a dressing power source 1910 positioned in or on the dressing 1978. The dressing power source 1910 can be coupled to (e.g., electrically coupled to) one or more components of the system 1974, such as one or more components of at least one of the robotic debridement apparatuses 1900.

In an embodiment, the dressing power source 1910 can provide the electrical power to at least one of the robotic debridement apparatuses 1900 using wires extending from the dressing 1978 to the at least one robotic debridement apparatus 1900. In an embodiment, the dressing power source 1910 can provide the electrical power to at least one of the robotic debridement apparatuses 1900 wirelessly. For example, the dressing power source 1910 can include at least one power storage device 1996 that is configured to store electrical power. For example, the power storage device 1996 can include a battery or a capacitor. The dressing power source 1910 can include at least one wireless power transmitter 1997. The wireless power transmitter 1997 can be electrically coupled to the power storage device 1996. The wireless power transmitter 1997 can be configured to receive electrical power from the power storage device 1996 and convert the electrical power into an energy source that can be transmitted wirelessly from the wireless power transmitter 1997 to at least one of the robotic debridement apparatuses 1900.

Each of the robotic debridement apparatuses 1900 configured to receive wireless power from the dressing power source 1910 can include at least one power receiver 1998. The power receiver 1998 can be positioned in or on the housing 1902 of its respective robotic debridement apparatus 1900. The power receiver 1998 is configured to convert the energy transmitted wirelessly from the wireless power transmitter 1997 into electrical power.

In an embodiment, the wireless power transmitter 1997 can include at least one optical energy-emitting device. The optical energy-emitting device can include a light-emitting diode, a laser, or another light emitting source that can convert electrical power to optical energy. In such an embodiment, the power receiver 1998 can include a device configured to convert the optical energy into electrical energy (e.g., one or more photodiodes).

In an embodiment, the wireless power transmitter 1997 can include at least one thermal energy-emitting device. The thermal energy-emitting device can include an infrared emitting device, an electrical resistive heater, or another thermal energy-emitting source that can convert electrical power to thermal energy. In such an embodiment, the power receiver 1998 can include one or more devices configured to convert the thermal energy into electrical power (e.g., one or more Peltier cells, one or more thermoelectric materials). In an embodiment, the thermal energy-emitting device can be configured to emit the thermal energy at an intensity low enough to not significantly damage healthy tissue in the body region 1976. In an embodiment, the thermal energy-emitting device is configured to emit the thermal energy at a location that does not include healthy tissue, such as directly at a robotic debridement apparatus 1900.

In an embodiment, the wireless power transmitter 1997 can include a magnetic energy-emitting device. The magnetic energy-emitting device can include at least one device configured to convert electrical power to magnetic energy (e.g., electromagnet). In such an embodiment, the power receiver 1998 can include a magnetic-electrical converter (e.g., induction coil) configured to convert the magnetic energy to electrical power. For example, the power receiver 1998 can include an RFID tag.

In an embodiment, the wireless power transmitter 1997 can include any other device configured to convert electrical power into an energy source that can be transmitted wirelessly. For example, the wireless power transmitter 1997 can include at least one acoustic energy-emitting device (e.g., ultrasonic energy-emitting device, radio-wave energy-emitting device), at least one resonant inductive coupling device, or at least one capacitive coupling device. As such, the power receiver 1998 can include a piezoelectric material, coiled wires, an electrode, or another device configured to convert the energy transmitted from the wireless power transmitter 1997 into electrical power.

In an embodiment, the dressing 1978 includes a controller 1912 that is coupled to the dressing power source 1910. For example, the dressing power source 1910 can provide electrical power to the controller 1912 and the controller 1912 can control the operation of the wireless power transmitter 1997. In an embodiment, the wireless power transmitter can operate responsive to directions from a controller 1912.

In an embodiment, the wireless power transmitter 1997 can transmit the wireless energy substantially simultaneously to a relatively large area of the body region 1976. As such, the wireless power transmitter 1997 can provide power to any robotic debridement apparatus 1900 positioned within the relatively large area. In an embodiment, the wireless power transmitter 1997 is configured to transmit the wireless energy to a relatively small selected area of the body region 1976 (e.g., beam). For example, the dressing 1978 can include one or more sensors 1908 configured to detect the position of at least one robotic debridement apparatus 1900 relative to the wireless power transmitter 1997. The wireless power transmitter 1997 or the controller 1912 can be used to detect the position of the robotic debridement apparatus 1900 to transmit the wireless energy directly to the robotic debridement apparatus 1900. For example, at least one actuator (not shown) coupled to the wireless power transmitter 1997 can move the wireless power transmitter 1997 relative to the dressing 1978 such that the wireless power transmitter 1997 transmits the energy directly the robotic debridement apparatus 1900. As another example, the wireless power transmitter 1997 can employ suitable beam steering techniques to direct the wireless energy thereof to the robotic debridement apparatus 1900. As such, substantially only the robotic debridement apparatus 1900 receives the wireless energy from the wireless power transmitter 1997 which allows the wireless power transmitter 1997 to transmit the energy at higher intensities and with greater efficiencies.

Referring to FIG. 20, an embodiment of a system 2074 includes a dressing 2078 associated with a plurality of robotic debridement apparatuses 2000 in which the dressing 2078 is configured to move at least one of the robotic debridement apparatuses 2000 relative to the body region 2076. For example, the dressing 2078 includes at least one magnetic field-generating device 2099. The magnetic field generating device 2099 can include at least one electromagnet (e.g., electromagnetic coils) or another suitable magnet. The magnetic field-generating device 2099 can generate rotating magnetic fields, time-varying magnetic fields or another suitable magnetic field.

In the illustrated embodiment, at least one of the robotic debridement apparatuses 2000 includes at least one locomotive mechanism 2004 that includes at least one magnet (e.g., neodymium-iron-boron magnet, temporary magnet, electromagnet, etc.). For example, the at least one magnetic can be part of or attached to a housing of the robotic debridement apparatuses 2000. The magnetic field generated by the magnetic field-generating device can be configured to move the magnet, thereby moving the at least one robotic debridement apparatus 2000 relative to the body region 2076.

In the illustrated embodiment, the dressing 2078 includes a controller 2012 that is communicably coupled to the magnetic field-generating device 2099. The controller 2012 can direct the magnetic field-generating device 2099 to controllably generate a magnetic field, thereby controllably moving the at least one robotic debridement apparatus 2000. In an embodiment, the at least one robotic debridement apparatus 2000 can include a controller 2012' that can direct the magnetic field generating device 2099 to controllably generate a magnetic field.

In an embodiment, the dressing 2078 can be configured to further control the movement of at least one of the robotic debridement apparatuses 2000 by including an anchor (not shown) that controllably maintains the robotic debridement apparatuses 2000 in substantially the same location for a selected period of time. For example, the anchor can include a suction device that controllably suctions at least one of the robotic debridement apparatuses 2000 to the dressing 2078.

Referring to FIG. 21, an embodiment of a system 2174 includes a dressing 2178 associated with a plurality of robotic debridement apparatuses 2100 in which the dressing 2178 is configured to at least one of position or remove at least one of the robotic debridement apparatuses 2100 from the body region 2176. For example, at least one of the robotic debridement apparatuses 2100 can include at least one extraction device 2170. The extraction device 2170 can be the same as or substantially similar to the extraction device 770 (FIG. 7). Additionally, the dressing 2178 can include at least one retrieval device 2172. The retrieval device 2172 can be the same as or substantially similar to the retrieval device 772 (FIG. 7). In an embodiment, the extraction device 2170 and the retrieval device 2172 are configured so as not to inhibit the housings 2102 of the robotic debridement apparatuses 2100 from being freestanding. In an embodiment, at least one of the robotic debridement apparatuses 2100 can be permanently coupled to the dressing 2178 via at least one of the retrieval device 2172 or the extraction device 2170.

In an embodiment, the extraction and retrieval devices 2170, 2172 are configured to position at least one of the robotic debridement apparatuses 2100 within the body region 2176 when the dressing 2178 is attached to the body region 2176. In an embodiment, the extraction and retrieval devices 2170, 2172 stop interacting with each other (e.g., are decoupled from each other) during operation of the robotic debridement apparatuses 2100. For example, an electromagnet that forms the extraction or retrieval device 2170, 2172 can be turned off. In an embodiment, the extraction and retrieval devices 2170, 2172 can continue to interact with each other (e.g., remain coupled together) during operation of the plurality of robotic debridement apparatuses 2100. In an embodiment, the extraction and retrieval devices 2170, 2172 are configured to remove at least one of the robotic debridement apparatuses 200 from the body region 2176 when the dressing 2178 is attached to the body region 2176. In an embodiment, the extraction or retrieval device 2170, 2172 can be configured to controllably maintain at least one of the robotic debridement apparatuses 2100 in substantially the same location for a selected period of time, for example, when debriding tissue. In such an embodiment, the extraction or retrieval device 2170, 2172 can also controllably allow the at least one robotic debridement apparatus 2100 free movement of the body region 2176.

Referring to FIG. 22, an embodiment of a system 2274 includes a dressing 2278 associated with a plurality of robotic debridement apparatuses 2200 in which at least one robotic debridement apparatus 2200 is directly coupled (e.g., attached) to the dressing 2278. For example, each of the robotic debridement apparatuses 2200 that are directly coupled to the dressing 2278 can be directly attached to a bottommost surface 2294 of the dressing 2278. Each of the robotic debridement apparatuses 2200 that are directly coupled to the dressing 2278 can be directly coupled to the dressing 2278 using an adhesive, a mechanical fastener (e.g., a screw, a bolt, etc.), a hook-and-eye fastener, a thread, a tether, or another attachment mechanism. The robotic debridement apparatuses 2200 that are directly coupled to the dressing 2278 can still facilitate debridement of the body region 2276. For example, the robotic debridement apparatuses 2200 can extend from the dressing 2278 sufficiently to debride tissue from the body region 2276, can dispense fluids (e.g., debriding, degrading, or therapeutic agents) into the body region 2276, can travel relative to the body region 2276, etc. For example, the robotic debridement apparatuses 2200 can extend (e.g., connected by a tether) a distance from the dressing 2278 that is sufficient to allow the robotic debridement apparatuses 2200 to travel throughout the body region 2276, debride tissue from the body region 2276, deliver an agent into or onto the body region 2276, capture a substance from the body region 2276, etc.

In an embodiment, at least one of the robotic debridement apparatuses 2200 that is directly coupled to the dressing 2278 can be reversibly coupled to the dressing 2278. For example, the robotic debridement apparatus 2200 is reversibly coupled when the robotic debridement apparatus 2200 can be attached to the dressing 2278 and detached from the dressing 2278 without damaging the robotic debridement apparatus 2200 and, optionally, without damaging the dressing 2278. Examples of reversibly coupling the robotic debridement apparatus 2200 to the dressing 2278 include hook-and-eye attachment, some adhesives, some tapes, magnets, etc. In an embodiment, the robotic debridement apparatus 2200 can be reversibly coupled to the dressing 2278 when the robotic debridement apparatus 2200 is reusable.

Referring back to FIG. 10, in an embodiment, at least one of the first, second, or third robotic debridement apparatuses 1000a, 1000b, 1000c can include a first association with a dressing (e.g., any of dressings 1178, 1278, 1378, 1478, 1578, 1678, 1778, 1878, 1978, 2078, 2178, 2278 of FIGS. 11-22), while another of the first, second, or third robotic debridement apparatuses 1000a, 1000b, 1000c include a second association with the dressing. For example, at least one of the first, second, or third robotic debridement apparatuses 1000a, 1000b, 1000c can be directly coupled (e.g., attached) to the dressing (FIG. 22), while another of the first, second, or third robotic debridement apparatuses 1000a, 1000b, 1000c can be indirectly coupled (e.g., via a tether) to the dressing (FIG. 21). In an embodiment, at least one of the first, second, or third robotic debridement apparatuses 1000a, 1000b, 1000c can be reversibly attached to the dressing (FIG. 21), while another of the first, second, or third robotic debridement apparatuses 1000a, 1000b, 1000c is substantially permanently attached to the dressing (FIG. 22). In an embodiment, at least one of the first, second, or third robotic debridement apparatuses 1000a, 1000b, 1000c can be positioned between the body region 1076 and the dressing (FIG. 12). In an embodiment, at least a portion of the dressing (e.g., a layer) can be positioned between at least one of the first, second, or third robotic debridement apparatuses 1000a, 1000b, 1000c and the body region 1076 (FIG. 13). In an embodiment, at least one of the first, second, or third robotic debridement apparatuses 1000a, 1000b, 1000c can be positioned between the body region 1076 and the dressing, while the dressing can be positioned between another of the first, second, or third robotic debridement apparatuses 1000a, 1000b, 1000c and the body region 1076. In another instance, at least one of the first, second, or third robotic debridement apparatuses 1000a, 1000b, 1000c can be communicably coupled to the dressing (via transceiver 1124' of FIG. 11A), while another of the first, second, or third robotic debridement apparatuses 1000a, 1000b, 1000c is not coupled to the dressing.

G. Methods of Using the Robotic Debridement Systems

Figure 23:
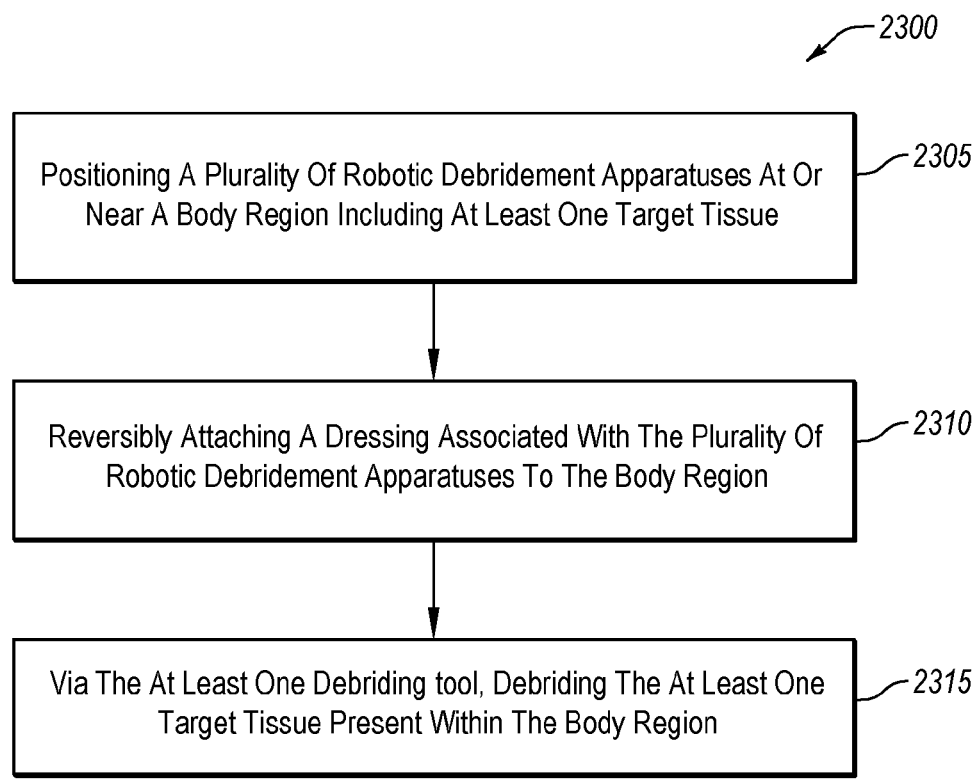
FIG. 23 is a flow diagram of a method of using any of the systems disclosed herein that include a dressing associated with a plurality of robotic debridement apparatuses, according to an embodiment.

FIG. 23 is a flow diagram of a method 2300 of using any of the systems disclosed herein according to an embodiment. In an embodiment, some of the acts of the method 2300 can be split into a plurality of acts, some of the acts can be combined into a single act, and some acts can be omitted. Also, it is understood that additional acts can be added to the method 2300.

Act 2305 includes positioning a plurality of robotic debridement apparatuses at or near a body region including at least one target tissue. The plurality of robotic debridement apparatuses, except as otherwise described herein, can be similar to or the same as the robotic debridement apparatuses 100, 200a-g, 300a-o, 400a-j, 500a-b, 600, 700, 1000 (FIGS. 1-7 and 10) and their respective materials, components, or elements. For example, the plurality of robotic debridement apparatuses can include a housing, at least one locomotive mechanism positioned in or on the housing, and at least one of at least one debriding tool or at least one debris disposal device. In an embodiment, at least one of the plurality of robotic debridement apparatuses positioned over the body region can include at least one of a sensor, a controller, a power source, a therapeutic device, a marking device, or an extraction device.

In an embodiment, disposing plurality of robotic debridement apparatuses at or near a wound region including a wound can include using an extraction device or retrieval device to position at least one of the plurality of robotic debridement apparatuses. For example, disposing plurality of robotic debridement apparatuses at or near a wound region including a wound can include placing at least one of the plurality of robotic debridement apparatuses over, into, or onto the body region using a extraction device or retrieval device to position. In an embodiment, disposing plurality of robotic debridement apparatuses at or near a wound region including a wound can include another method of disposing at least one of the plurality of robotic debridement apparatuses over the body region.

Act 2310 includes reversibly attaching a dressing associated with the plurality of robotic debridement apparatuses to the body region. Except as otherwise described herein, the dressing can be similar to or the same as the dressings 1178, 1278, 1378, 1478, 1578, 1678, 1778, 1878, 1978, 2078, 2178, 2278 (FIGS. 11A-22) and their respective materials, components, or elements. For example, the dressing can include at least one layer that at least partially encloses the body region or at least one of the robotic debridement apparatuses. In an embodiment, the dressing can be configured to be a confinement dressing or a containment dressing.

In an embodiment, act 2305 is performed before act 2310. For example, the plurality of robotic debridement apparatuses are disposed directly in the body region before the dressing is reversibly attached to the body region (e.g., the plurality of robotic debridement apparatuses are positioned between the wound and the dressing). In an embodiment, act 2310 is performed before act 2305. For example, the dressing is reversibly attached to the body region and the plurality of robotic debridement apparatuses are then positioned over the dressing (e.g., the dressing is positioned between the wound and the plurality of robotic debridement apparatuses). In an embodiment, the act 2305 and act 2310 are performed substantially simultaneously. For example, the plurality of robotic debridement apparatuses are positioned in or on the dressing (e.g., in a containment region) before the dressing is reversibly attached to the body region. Therefore, reversibly attaching the dressing to the body region also disposes the plurality of robotic debridement apparatuses at the body region. In an embodiment, the robotic debridement apparatuses are coupled to the dressing such that reversibly attaching the dressing to the body region also positions the robotic debridement apparatuses in the body region. In an embodiment, the act 2305 is performed substantially simultaneously with and at least one of before or after act 2310. For example, at least one of the plurality of robotic debridement apparatuses is positioned in or on the dressing. Therefore, reversibly attaching the dressing to the body region also disposes the at least one of the plurality of robotic debridement apparatuses at the body region. However, the remaining robotic debridement apparatuses are disposed at or near the body region before (e.g., directly into the body region) or after (e.g., on the dressing) the dressing is reversibly attached to the body region.

Act 2315 includes, via the at least one debriding tool, debriding the at least one target tissue present within the body region. In an embodiment, the tissue present in the body region is debrided in substantially the same manner as described in act 810 of method 800 (FIG. 8). For example, at least one of the plurality of robotic debridement apparatuses can include at least one debriding tool that debrides tissue from the body region. In an embodiment, the tissue is debrided using the dressing. For example, the dressing can be configured to dispense one or more debriding agents into the body region. In an embodiment, the tissue can be debrided by a user (e.g., physician) using, for example, a curette, a scalpel, or another device. For example, the tissue can first be debrided by a user and at least one of robotic debridement apparatuses includes a debris disposal device that captures debris from the body region. The user can insert the device through an opening (e.g., opening 1186 of FIGS. 11A-11B) defined by the dressing. In an embodiment, the tissue can be debrided using one or more maggots applied to the body region. For example, tissue in the body region can be debrided by at least one robotic debridement apparatus having a debriding tool, and one or more maggots can subsequently be applied to the body region for a specific (e.g., longer) time period to consume debrided tissue and debris.

In an embodiment, the method 2300 can include selecting the plurality of robotic debridement apparatuses from a variety of robotic debridement apparatuses. For example, the variety of robotic debridement apparatuses can include at least two different types of robotic debridement apparatuses (e.g., different functionality, size, etc.). The plurality of robotic debridement apparatuses can be selected based on the size of the body region, the tissue to be debrided, the type of dressing used, etc.

In an embodiment, the method 2300 can include coupling at least one of the plurality of robotic debridement apparatuses to the dressing. In an embodiment, at least one of the plurality of robotic debriding apparatuses include at least one extraction device (e.g., extraction device 2170 of FIG. 21), and the dressing includes at least one retrieval device (e.g., retrieval device 2172 of FIG. 21). The extraction and retrieval device can be coupled together. In an embodiment, at least one of the plurality of robotic debridement apparatuses is directly coupled (e.g., attached) to the dressing using an adhesive, a mechanical fastener, or another attachment mechanism.

In an embodiment, the method 2200 can include the dressing dispensing one or more fluids into the body region. In an embodiment, the dressing is configured to dispense the fluids using a passive fluid delivery system. The passive fluid delivery system can include plurality of regions (e.g., regions 1492 of FIG. 14) that include the fluids therein. The regions can dispense the fluids using gravity, pressure between the dressing and the body region, etc. In an embodiment, the dressing is configured to dispense the fluids using an active fluid delivery system. The active fluid delivery system can deliver the fluids by actuating a plurality of actuators that are operably coupled to a fluid source (e.g., at least one of the fluid reservoir 1535 or fluid-dispense element 1536 of FIG. 15). The fluids dispensed from the dressing can include one or more debriding agents, one or more therapeutic agents, one or more taggants, or another fluid-disclosed herein. In some embodiments, the dressing can dispense the fluids into the body region responsive to direction from a controller (e.g., controller 112 of FIG. 1, controller 1112 of FIG. 11A).

In an embodiment, the method 2300 can include the dressing disposing of at least one substance (e.g., debriding tissue, foreign matter, or fluids) present in the body region. For example, the dressing can dispense one or more debriding agents into the body region. In an embodiment, the dressing removes the at least one substance from the body region. For example, the dressing can suction the at least one substance from the body region (e.g., using the suction device 1654 of FIG. 16) and store the removed substances in a debris reservoir. In an embodiment, the dressing can attach thereto (e.g., absorb, wick, adhere) the at least one substance from the body region. For instance, the dressing can attach the at least one substance from the body region thereto using an absorbent material (e.g., using absorbent material 1758 of FIG. 17) positioned therein or thereon. The dressing can controllably capture the at least one substance in the body region responsive to direction from a controller (e.g., controller 112 of FIG. 1, controller 1112 of FIG. 11A).

In an embodiment, the method 2300 can include the dressing providing a therapeutic effect to the body region. For example, the dressing can dispense one or more therapeutic agents into the body region. In another example, the dressing can stimulate at least a portion of the body region using light, acoustic energy, electrical energy, or thermal energy (e.g., using the energy-emitting device 1864 of FIG. 18), thereby at least one of disinfecting, sterilizing, facilitating healing of, or otherwise providing a therapeutic effect to the body region. The dressing can controllably provide a therapeutic effect to the body region using a controller (e.g., controller 112 of FIG. 1, controller 1112 of FIG. 11A).

In an embodiment, the method 2300 can include the dressing sensing one or more characteristics of the body region using one or more sensors positioned therein or thereon (e.g., sensors 1108 of FIG. 11A). For example, the sensors can detect the presence, location, quantity, etc. of viable tissue or nonviable tissue. The sensors can transmit one or more sensing signals that include the detected characteristics encoded therein to one or more components of the system. The dressing can sense one or more characteristics of the body region and transmit the sensing signals responsive to direction from a controller (e.g., controller 112 of FIG. 1, controller 1112 of FIG. 11A).

In an embodiment, the method 2300 can include controlling the operation of one or more components of the system using a controller positioned in or on the dressing (e.g., controller 1112 of FIG. 11A). For example, the controller can control the operation of the one or more components of the system responsive to receiving the sensing signals from the sensors. In an embodiment, the controller can control the operation of one or more components of the dressing. For example, the dressing can dispense one or more fluids, capture at least one substance present in the body region, provide a therapeutic effect to the body region, or otherwise operate responsive to direction from the controller. In another example, at least one of the robotic debridement apparatuses can at least one of travel relative to the body region, debride tissue, capture at least one substance in the body region, provide a therapeutic effect to the body region, or otherwise operate responsive to direction from the controller.

In an embodiment, the method 2300 can include providing power from the dressing to at least one of the robotic debridement apparatuses. In an embodiment, the dressing can wiredly provide electrical power to any robotic debridement apparatus. In an embodiment, the dressing can wirelessly provide electrical power to at least one of the robotic debridement apparatus. For example, the dressing can include a dressing power source (e.g., dressing power source 1910 of FIG. 19) that includes a power storage device (e.g., power storage device 1996 of FIG. 19) and a wireless power transmitter (e.g., wireless power transmitter 1997 of FIG. 19). In such an example, the wireless power transmitter can receive electrical power stored in the power storage device and convert the electrical power into an energy that can be transmitted wirelessly. The wireless power transmitter can then wirelessly transmit the energy to at least one robotic debridement apparatus that includes a power receiver (e.g., power receiver 1998 of FIG. 19). The power receiver can then convert the received energy into electrical power. The dressing can controllably provide power to at least one of the robotic debridement apparatuses responsive to direction from a controller (e.g., controller 112 of FIG. 1, controller 1112 of FIG. 11A).

In an embodiment, the method 2300 can include the dressing removing at least one of the robotic debridement apparatuses from the body region when the dressing is removed from the body region. In an embodiment, at least one of robotic debridement apparatuses can be directly coupled to the dressing. In an embodiment, at least one of the robotic debridement apparatuses are coupled to the dressing using an extraction device and a retrieval device. For example, the extraction and retrieval devices can be coupled together responsive to direction from a controller (e.g., controller 112 of FIG. 1, controller 1112 of FIG. 11A). In an embodiment, at least one of the robotic debridement apparatuses can be removed manually (e.g., by a user) from the body region.

In an embodiment, the method 2300 can include the dressing moving at least one of the robotic debridement apparatuses within the body region. For example, the dressing can include a magnetic field generating device (e.g., magnetic field generating device 2099 of FIG. 20) and at least one of the robotic debridement apparatuses includes at least one locomotive mechanism comprising a magnet (e.g., locomotive mechanism 2004 of FIG. 20). The magnetic field generating device can controllably generate a magnetic field that is configured to controllably move the at least one robotic debridement apparatus within the body region. For instance, the magnetic field generating device can controllably generate a magnetic field responsive to direction from a controller (e.g., controller 112 of FIG. 1, controller 1112 of FIG. 11A)

In an embodiment, the method 2300 can include any of the optional additional acts disclosed in methods 800 and 900 (FIGS. 8-9).

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications can be made to the embodiments without departing from the scope of the present disclosure. For example, various operational steps, as well as components for carrying out operational steps, can be implemented in alternate ways depending upon the particular application or in consideration of any number of cost functions associated with the operation of the system; e.g., one or more of the steps can be deleted, modified, or combined with other steps.

Additionally, as will be appreciated by one of ordinary skill in the art, principles of the present disclosure, including components, can be reflected in a computer program product on a computer-readable storage medium having computer-readable program code means embodied in the storage medium. Any tangible, non-transitory computer-readable storage medium can be utilized, including magnetic storage devices (hard disks, floppy disks, and the like), optical storage devices (CD-ROMs, DVDs, Blu-ray discs, and the like), flash memory, and/or the like. These computer program instructions can be loaded onto a general purpose computer, special purpose computer, or other programmable data processing apparatus to produce a machine, such that the instructions that execute on the computer or other programmable data processing apparatus create a means for implementing the functions specified. These computer program instructions can also be stored in a computer-readable memory that can direct a computer or other programmable data processing apparatus to function in a particular manner, such that the instructions stored in the computer-readable memory produce an article of manufacture, including implementing means that implement the function specified. The computer program instructions can also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the robotic debriding apparatuses or related systems disclosed herein can be integrated in such a manner that the robotic debriding apparatuses or related systems operate as a unique system configured specifically for function of facilitating debridement of tissue from a body region and any associated computing devices of the robotic debriding apparatuses or related systems operate as specific use computers for purposes of the claimed system, and not general use computers. In an embodiment, at least one associated computing device of the robotic debriding apparatuses or related systems operate as specific use computers for purposes of the claimed system, and not general use computers. In an embodiment, at least one of the associated computing devices of the robotic debriding apparatuses or related systems are hardwired with a specific ROM to instruct the at least one computing device. In an embodiment, one of skill in the art recognizes that the robotic debriding apparatuses or related systems effects an improvement at least in the technological field of facilitating debridement of tissue from a wound region.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A robotic debridement apparatus, comprising:
   a housing including a bottom;
   at least one locomotive mechanism positioned in or on the housing, the at least one locomotive mechanism configured to generate a self-propelling locomotive force; and
   at least one debriding tool associated with the housing, the at least one debriding tool positioned on the housing to debride tissue of a wound region on an exterior of an individual that is adjacent to or below the bottom of the housing.

2. The robotic debridement apparatus of claim 1, wherein the at least one locomotive mechanism includes a piezoelectric material.

3. The robotic debridement apparatus of claim 2, wherein the piezoelectric material includes at least one of a piezoelectric inchworm motor, a piezoelectric bending actuator, a piezoelectric unimorph, a piezoelectric bimorph, a piezoelectric motor, or a piezoelectric transducer.

4. The robotic debridement apparatus of claim 1, wherein the at least one locomotive mechanism includes a vibratory mechanism.

5. The robotic debridement apparatus of claim 1, wherein the at least one locomotive mechanism includes at least one impelling mechanism.

6. The robotic debridement apparatus of claim 5, wherein the at least one impelling mechanism includes at least one of appendages, legs, or wheels at least partially extending from the housing.

7. The robotic debridement apparatus of claim 1, wherein the at least one locomotive mechanism includes one or more actuators operably coupled to one or more portions of the housing, the one or more actuators configured to drive the one or more portions of the robotic debridement apparatus.

8. The robotic debridement apparatus of claim 1, wherein the at least one debriding tool includes one or more sharp cutting tools, one or more scraping tools, or one or more protrusions.

9. The robotic debridement apparatus of claim 1, wherein the at least one debriding tool includes at least one abrasive material positioned on at least a portion of an outer surface of the housing or a portion of the at least one debriding tool.

10. The robotic debridement apparatus of claim 1, wherein a portion of the at least one debriding tool is spaced from and coupled to the housing.

11. The robotic debridement apparatus of claim 1, wherein the at least one debriding tool is moveable relative to the housing.

12. The robotic debridement apparatus of claim 1, wherein the at least one debriding tool includes an energy-emitting device configured to emit at least one of acoustic energy or electromagnetic energy.

13. The robotic debridement apparatus of claim 1, wherein the at least one debriding tool includes at least one debriding agent reservoir positioned in or on the housing; and at least one debriding-dispense element operably coupled to the at least one debriding agent reservoir, the at least one debriding-dispense element including at least one debriding-dispense aperture.

14. The robotic debridement apparatus of claim 13, wherein the at least one debriding tool is configured to dispense one or more pressurized fluids from the at least one debriding-dispense aperture with sufficient force to separate target tissue from other tissue.

15. The robotic debridement apparatus of claim 13, wherein the at least one debriding agent reservoir is configured to store one or more debriding agents therein.

16. The robotic debridement apparatus of claim 15, wherein the one or more debriding agents include at least one of one or more lytic compounds or one or more enzymatic agents.

17. The robotic debridement apparatus of claim 15, wherein the one or more debriding agents include at least one of an abrasive compound, a reactive chemical, or an irrigation fluid.

18. The robotic debridement apparatus of claim 15, wherein the one or more debriding agents include at least one of a gel, a hydrogel, a colloid, or a hydrocolloid.

19. The robotic debridement apparatus of claim 1, wherein the at least one debriding tool is configured to debride a target tissue.

20. The robotic debridement apparatus of claim 1, further including at least one three-dimensional micropillar coupled to one or more components of the robotic debridement apparatus.

21. The robotic debridement apparatus of claim 1, further including at least one extraction device positioned in or on the housing.

22. The robotic debridement apparatus of claim 21, wherein the at least one extraction device includes at least one of a magnet, a magnetically attractable material, or a protruding element extending from an outer surface of the housing.

23. The robotic debridement apparatus of claim 1, further including at least one debris disposal device positioned in or on the housing, the at least one debris disposal device configured to capture at least one substance from a body region.

24. The robotic debridement apparatus of claim 23, wherein the at least one substance includes at least one of debrided tissue, foreign matter, one or more fluids, or at least one infectious material.

25. The robotic debridement apparatus of claim 23, wherein the at least one debris disposal device includes at least one of an adhesive material;
an absorbent material;
a suction device; or
a debris reservoir.

26. The robotic debridement apparatus of claim 1, further including at least one therapeutic device positioned in or on the housing.

27. The robotic debridement apparatus of claim 26, wherein the at least one therapeutic device includes a therapeutic agent-dispensing device including at least one therapeutic agent reservoir positioned in or on the housing; and
at least one therapeutic-dispense element operably coupled to the therapeutic agent reservoir, the at least one therapeutic-dispense element including at least one therapeutic-dispense aperture.

28. The robotic debridement apparatus of claim 27, wherein the therapeutic agent reservoir includes one or more therapeutic agents stored therein, the one or more therapeutic agents including at least one of one or more medicaments, one or more anaesthetics, one or more antibiotics, one or more antimicrobials, one or more antiseptics, or one or more antimicrobial peptides.

29. The robotic debridement apparatus of claim 27, wherein the therapeutic agent reservoir includes one or more therapeutic agents stored therein, the one or more therapeutic agents including at least one of one or more cytokines, one or more growth factors, one or more vitamins, one or more minerals, one or more cells, one or more hydrogels, one or more hydrocolloids, synthetic dermis, or a liquid bandage.

30. The robotic debridement apparatus of claim 27, wherein the therapeutic agent reservoir includes one or more therapeutic agents stored therein, the one or more therapeutic agents including at least one of collagen, allantoin, urea, phenylacetic acid, phenylacetaldehyde, or calcium carbonate.

31. The robotic debridement apparatus of claim 26, wherein the at least one therapeutic device includes at least one energy-emitting device.

32. The robotic debridement apparatus of claim 1, further including a controller operably coupled to one or more components of the robotic debridement apparatus.

33. The robotic debridement apparatus of claim 32, wherein the controller includes at least one of non-transitory memory configured to store one or more operational instructions thereon or a transceiver; and
a processor operably coupled to the non-transitory memory or the transceiver.

34. The robotic debridement apparatus of claim 1, further including an external device, the external device coupled to one or more components of the robotic debridement apparatus.

35. The robotic debridement apparatus of claim 1, further including one or more sensors positioned in or on the housing.

36. The robotic debridement apparatus of claim 35, wherein the one or more sensors include one or more of at least one chemical sensor, at least one thermal sensor, at least one moisture sensor, at least one electrical conductivity sensor, at least one optical sensor, or at least one acoustic sensor.

37. The robotic debridement apparatus of claim 35, wherein the one or more sensors are configured to detect at least one of necrotic tissue, viable tissue, nonviable tissue, slough, ischemic tissue, fibrinous tissue, connective tissue, epithelial tissue, endothelial tissue, granulation tissue, inflammation, a microbe, or a toxin.

38. The robotic debridement apparatus of claim 1, further including, at least one taggant reservoir positioned in or on the housing, the at least one taggant reservoir configured to store one or more taggants; and at least one taggant-dispense element operably coupled to the at least one taggant reservoir, the at least one taggant-dispense element including at least one taggant-dispense aperture.

39. The robotic debridement apparatus of claim 38, wherein the one or more taggants are selected to indicate at least one of a path of the robotic debridement apparatus, a location where the at least one debriding tool was used, one or more types of tissue, one or more cell types, one or more microbes, or one or more types of debris.

40. The robotic debridement apparatus of claim 38, wherein the one or more taggants include at least one recognition element.

41. The robotic debridement apparatus of claim 1, wherein the housing exhibits a length that is about 1 micrometer to about 10 centimeters.

42. The robotic debridement apparatus of claim 1, wherein the housing includes a freestanding housing.

43. A robotic debridement system, comprising:
a plurality of robotic debridement apparatuses, at least one of the plurality of robotic debridement apparatuses including
a housing;
at least one locomotive mechanism positioned in or on the housing, the at least one locomotive mechanism configured to generate a self-propelling locomotive force; and
at least one debriding tool associated with the housing; and
a dressing including at least one layer, the dressing having sufficient size to at least partially enclose one or more of the plurality of debridement apparatuses.

44. The robotic debridement system of claim 43, wherein the at least one debriding tool includes at least one of
at least one blade, the at least one blade include one or more sharp cutting tools or one or more scraping tools;
one or more protrusions; or
an abrasive material positioned on at least a portion of an outer surface of the housing or a portion of the at least one debriding tool.

45. The robotic debridement system of claim 43, wherein the at least one debriding tool includes an energy-emitting device configured to emit at least one of electromagnetic energy, acoustic energy, electrical energy, or thermal energy.

46. The robotic debridement system of claim 43, wherein one or more of the plurality of robotic debridement apparatuses includes at least one therapeutic device, the at least one therapeutic device including at least one of
a therapeutic agent-dispensing device including,
a therapeutic agent reservoir positioned in or on the housing; and
at least one therapeutic-dispense element operably coupled to the therapeutic agent reservoir, the at least one therapeutic-dispense element including at least one therapeutic-dispense aperture; or
an energy-emitting device.

47. The robotic debridement system of claim 43, wherein at least one of the plurality of robotic debridement apparatuses includes at least one extraction device positioned in or on to the housing.

48. The robotic debridement system of claim 47, wherein the at least one extraction device includes at least one of a magnet, a magnetically attractable material, a protruding element extending outwardly from the housing, or an attachment location.

49. The robotic debridement system of claim 47, further including at least one retrieval device coupleable to the at least one extraction device, the at least one retrieval device including at least one of a magnet, a magnetically attractable material, a forceps, a hook, or a tether.

50. The robotic debridement system of claim 43, wherein one or more of the plurality of robotic debridement apparatuses includes a controller, the controller operably coupled to one or more components of the one or more of the plurality of robotic debridement apparatuses.

51. The robotic debridement system of claim 50, wherein the controller is configured to control at least one of the one or more component of the one or more of the plurality of robotic debridement apparatuses.

52. The robotic debridement system of claim 50, wherein at least one of the plurality of robotic debridement apparatuses includes one or more sensors operably coupled to the controller.

53. The robotic debridement system of claim 43, wherein the plurality of robotic debridement apparatuses includes
at least one first robotic debridement apparatus including a first controller, the first controller including a first transceiver; and
at least one second robotic debridement apparatus including a second transceiver communicably coupled to the first transceiver;
wherein the first controller is configured to at least partially control the operation of one or more components of the at least one first robotic debridement apparatus and the at least one second robotic debridement apparatus.

54. The robotic debridement system of claim 53, wherein the at least one second robotic debridement apparatus includes a second controller, the second controller including the second transceiver; wherein the second controller is configured to at least partially control the operation of one or more components of the at least one first robotic debridement apparatus and the at least one second robotic debridement apparatus.

55. The robotic debridement system of claim 53, wherein the at least one first robotic debridement apparatus includes one or more sensors operably coupled thereto and operably coupled to the first controller, wherein the first controller at least partially controls the operation of the one or more components of the at least one first robotic debridement apparatus and the at least one second robotic debridement apparatus responsive to receiving one or more sensing signals from the one or more sensors.

56. The robotic debridement system of claim 53, wherein the at least one second robotic debridement apparatus includes one or more sensors operably coupled to the first controller via the first and second transceivers, wherein the first controller at least partially controls the operation of one or more components of the at least one first robotic debridement apparatus or the at least one second robotic debridement apparatus responsive to receiving one or more sensing signals from the one or more sensors.

* * * * *